United States Patent
Errico et al.

(10) Patent No.: US 12,172,016 B2
(45) Date of Patent: Dec. 24, 2024

(54) SYSTEMS AND METHODS FOR INITIAL PROVISIONING AND REFILLING OF MEDICAL DEVICES

(71) Applicant: ElectroCore, Inc., Rockaway, NJ (US)

(72) Inventors: Joseph P. Errico, Palm Beach Gardens, FL (US); Arthur F. Ross, Fernandina Beach, FL (US); Muhammad Basit Qari, Somerset, NJ (US)

(73) Assignee: ElectroCore, Inc., Rockaway, NJ (US)

( * ) Notice: Subject to any disclaimer, the term of this patent is extended or adjusted under 35 U.S.C. 154(b) by 0 days.

(21) Appl. No.: 18/196,491

(22) Filed: May 12, 2023

(65) Prior Publication Data

US 2023/0277844 A1 Sep. 7, 2023

Related U.S. Application Data

(63) Continuation of application No. 17/002,347, filed on Aug. 25, 2020, now Pat. No. 11,684,778, which is a
(Continued)

(51) Int. Cl.
*A61N 1/36* (2006.01)
*A61N 1/02* (2006.01)
(Continued)

(52) U.S. Cl.
CPC ......... *A61N 1/36034* (2017.08); *A61N 1/025* (2013.01); *A61N 1/0456* (2013.01); *G06K 7/10366* (2013.01); *G06K 7/1413* (2013.01); *G06K 7/1417* (2013.01); *G16H 10/65* (2018.01); *G16H 20/10* (2018.01); *G16H 20/30* (2018.01); *G16H 40/40* (2018.01); *G16H 40/63* (2018.01)

(58) Field of Classification Search
CPC .. A61N 1/36034; A61N 1/025; A61N 1/0456; A61N 1/3603; G06K 7/10366; G06K 7/1413; G06K 7/1417; G16H 10/65; G16H 20/10; G16H 20/30; G16H 40/40; G16H 40/63
USPC .......................................................... 607/59
See application file for complete search history.

(56) References Cited

U.S. PATENT DOCUMENTS

2014/0257438 A1* 9/2014 Simon ...................... A61N 2/02
607/150
2014/0324118 A1* 10/2014 Simon .................. A61B 5/7267
607/46

(Continued)

OTHER PUBLICATIONS

FDA, De Novo Classification Request For gammaCore Non-Invasive Vagus Nerve Stimulator, Oct. 15, 2015, pp. 1-22, https://www.accessdata.fda.gov/cdrh_docs/reviews/DEN150048.pdf (Year: 2015).*

*Primary Examiner* — Joy Chng
(74) *Attorney, Agent, or Firm* — Farber LLC

(57) ABSTRACT

A system is provided that includes a medical device comprising a power supply, a signal generator and an electrode. The signal generator is configured to apply one or more electrical impulses to the electrode for a period of time defined as a single dose. The system further comprises a processor coupled to the medical device. The processor is configured to switch the medical device from an activated mode to a deactivated mode after a specific number of single doses have been applied by the signal generator.

17 Claims, 37 Drawing Sheets

Related U.S. Application Data continuation-in-part of application No. 16/229,299, filed on Dec. 21, 2018, now Pat. No. 11,581,090.

(60) Provisional application No. 62/609,807, filed on Dec. 22, 2017.

(51) Int. Cl.
| | |
|---|---|
| *A61N 1/04* | (2006.01) |
| *G06K 7/10* | (2006.01) |
| *G06K 7/14* | (2006.01) |
| *G16H 10/65* | (2018.01) |
| *G16H 20/10* | (2018.01) |
| *G16H 20/30* | (2018.01) |
| *G16H 40/40* | (2018.01) |
| *G16H 40/63* | (2018.01) |

(56) References Cited

U.S. PATENT DOCUMENTS

2015/0230760 A1* 8/2015 Schneider ............. A61M 5/172
  600/300
2015/0339460 A1* 11/2015 Marsico ................ G16H 20/10
  705/2

* cited by examiner

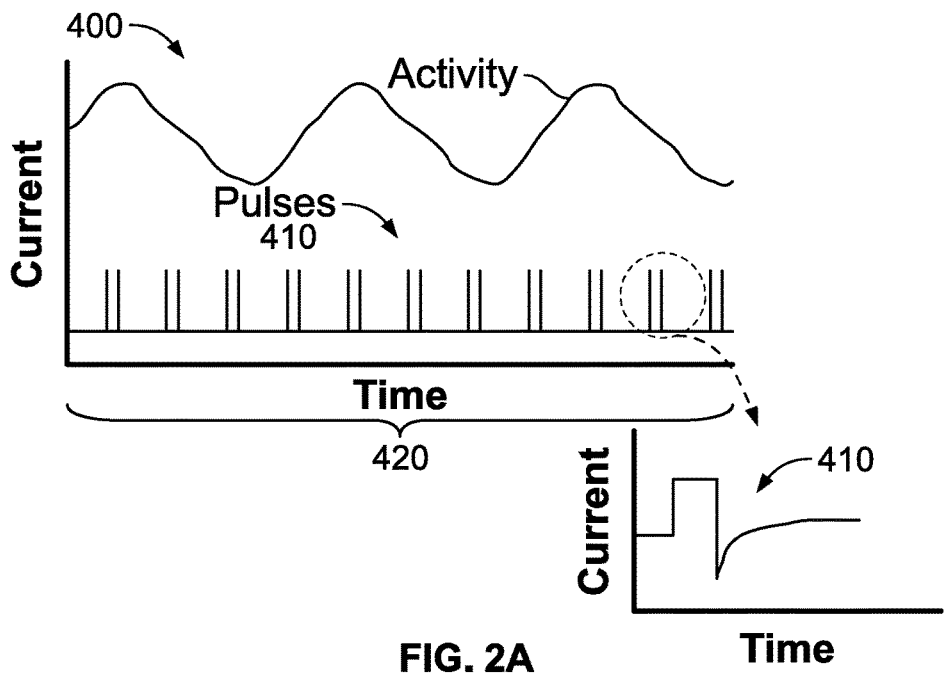
FIG. 2A
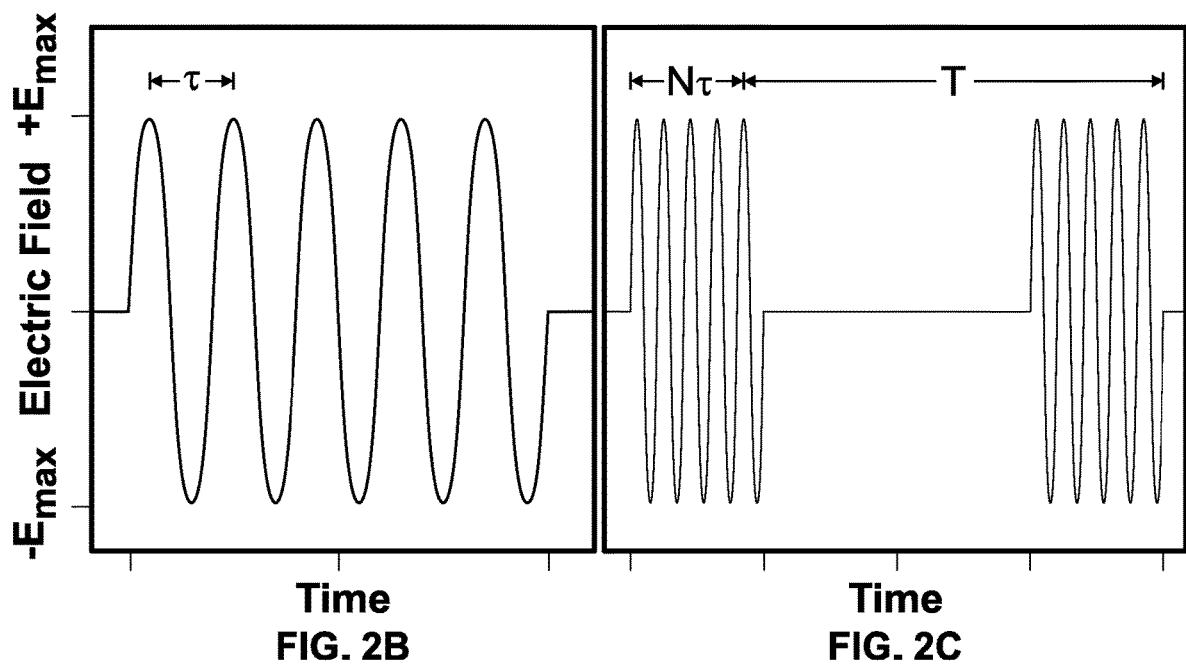
FIG. 2B
FIG. 2C

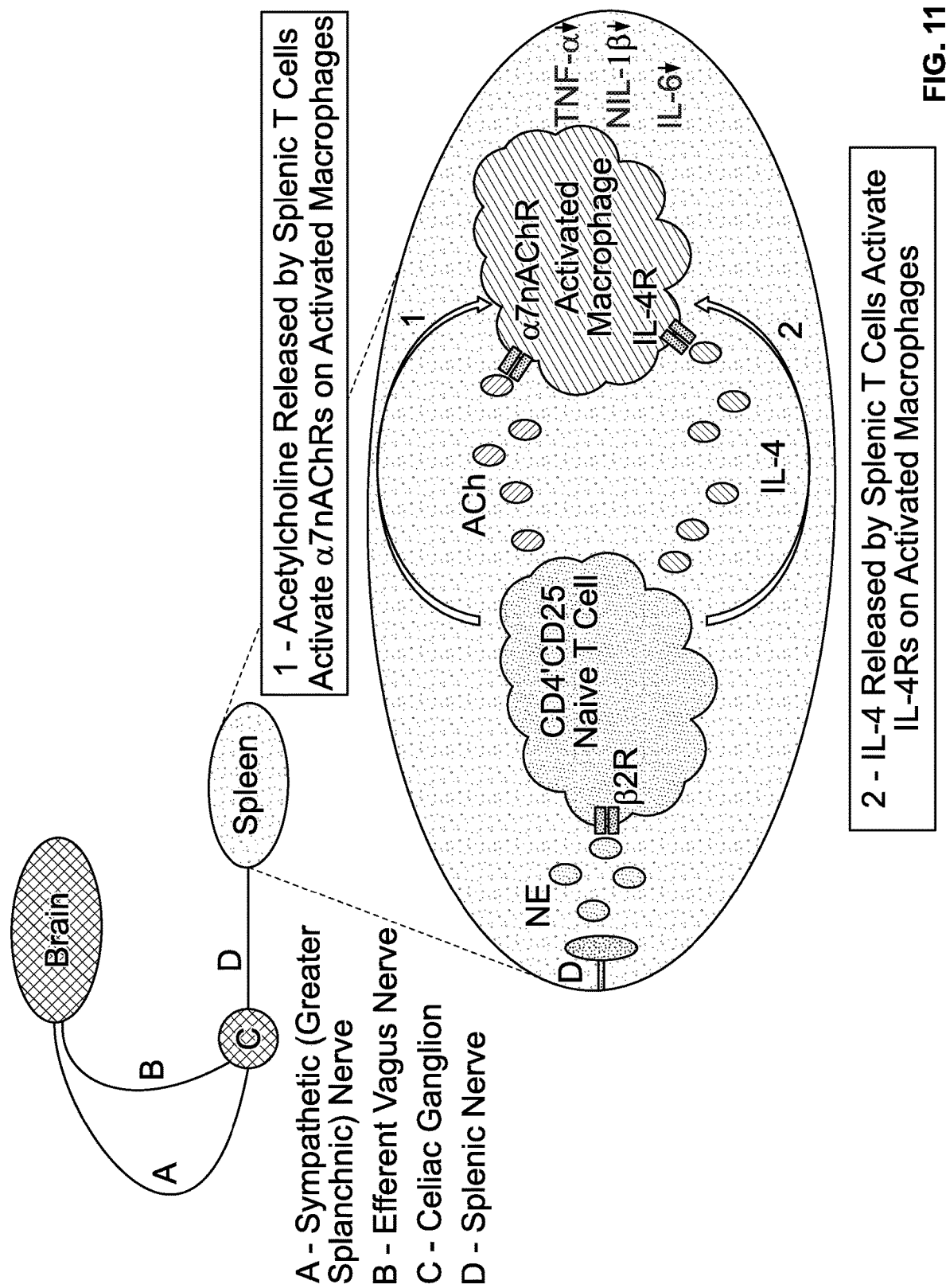

FIG. 19B

Logged in *****

Prescription Info

ASPN ID [839736]  Look UP  OR  Scan ASPN ID

Doses/Days [7]   Days of Therapy [33]

Fill Date [N/A]  Refills Remaining [3]

Fill Number [2]  Device ID [N/A]

Next

| | | |
|---|---|---|
| Treatments Remaining |  | 6 Treatments Remaining Within a 24 Hour Period |
| Stimulation Intensity |  | Stimulation Intensity at 23, symbol Indicates a Signal at Stimulation Surfaces. Stimulation Intensity can Range from 1 - 40. |
| Days Remaining |  | 30 Days Remaining Until Device Expires and will not Deliver Treatments |
| Stimulation Intensity at Last Use |  | Last Stimulation Intensity |
| Battery |  | Battery Charge Indicator |
| Reload |  | Refill Card is Being Read |

FIG. 20B

| | | | |
|---|---|---|---|
| Start Up / Ready for Use | Days Remaining Doses Remaining<br>30 ⇄ 06<br>2 Seconds | 1 Short Beep After Power ON | Follow "How to Use" Instructions |
| Device in Use | Stimulation Intensity (Min 1 - Max 40)<br>23 | Short Beep Each Time Intensity is Increased/ Decreased | Follow "How to Use" Instructions |
| Dose Complete | 1. Number of Days Remaining<br>30<br>2. Number of Doses Remaining<br>06<br>3. Last Stimulation Level<br>23 | 2 Short Beeps | NONE: Device Turns Off Automatically |
| Error | E1 | Repeated Long Beeps | Device Turns Off Automatically After 10 Seconds<br>Restart Device (Turn Off and On Again)* |
| No Doses Remaining | 00 | Repeated Long Beeps | Device Turns Off Automatically<br>Maximum Number of Treatments Reached Within 24 Hours. Wait Until Next 24-hour Period |
| Expired/No Days Left | 00 | Repeated Long Beeps | Device Turns Off Automatically<br>Replace Device* |

FIG. 20C

| | | |
|---|---|---|
| Low Battery | [icon] | Repeated Long Beeps | Place in Charging Station |
| Dead Battery | None | None | Place in Charging Station |
| Charging | [icon] Battery Charge Indicator Bars Flash and Increases | None | Allow Device to Fully Charge |
| Charging Complete | [icon] | None | Remove Device from Charging Station<br>Device is Ready to Use |
| Device Not Aligned in Charging Station | [icon] | None | Ensure Device is Fully Seated in Charging Station |
| Charging Error | [icon] | Repeated Long Beeps | Remove Device From Charging Station and Place Back In*<br>Unplug Charging Base Power Adapter from the Outlet and Plug in Again* |
| Reloading Error | [icon] | None | Restart Device<br>(Turn Off and On Again)* |
| Card Error | [icon] | None | Wait 24 Hours and Restart Device<br>(Turn Off and On Again)* |

*If Error is not Resolved Contact Customer Service

FIG. 20D

| Power Button | Increase Intensity | Decrease Intensity |
|---|---|---|
| | | |
| Press the Power Button to Turn Device ON<br><br>Hold the Power Button to Turn the Device OFF | Press the Upper Area of the Control Button | Press the Lower Area of the Control Button |

FIG. 20G

SYSTEMS AND METHODS FOR INITIAL PROVISIONING AND REFILLING OF MEDICAL DEVICES

CROSS REFERENCE TO RELATED APPLICATIONS

This patent application is a Continuation of U.S. Nonprovisional application Ser. No. 17/002,347, filed Aug. 25, 2020, which is a Continuation-in-Part of U.S. Nonprovisional application Ser. No. 16/229,299 filed 21 Dec. 2018; which claims the benefit of U.S. Provisional Application No. 62/609,807 filed 22 Dec. 2017; all of which are hereby incorporated by reference for all purposes as if copied and pasted herein.

BACKGROUND

There is a desire in the industry for a technology that enables an initial provisioning and a refilling of a medical device, such as non-invasive electrical stimulation devices. However, such technology does not exist. Therefore, this description enables such technology.

SUMMARY

In one aspect, a system comprises a medical device that includes a reader and a processor, and a storage medium comprising a content. The reader is configured to read the content from the storage medium such that the processor switches the medical device from a first mode to a second mode based on the content.

In some embodiments, the first mode of the medical device is a deactivated mode and the second mode is an activated mode. The activated mode is configured for a defined time period and/or a defined number of doses such that the medical device will stop working after a defined time period or a defined number of doses. This allows the device to be used, for example, by patients after having been prescribed a medical treatment by a physician or other caregiver. The physician may prescribe a defined number of doses and/or a defined period of time for the patient to use the medical device and receive treatment. When that time period and/or number of doses has been completed, the device is switched back to the deactivated mode so that the patient will no longer receive treatment from the device.

In this manner, the storage medium may "fill" the medical device with an initial number of doses or an active time period for a patient. The medical device will automatically become deactivated when the patient has completed the prescribed number of doses or time period. In some embodiments, the medical device can be capable of being "refilled" with an additional number of doses and or an additional amount of active time by switching the device back to the first or activated mode. This allows the physician or caregiver to control the level of treatment that a patient receives with the medical device.

In some embodiments, the content from the storage medium is deleted, or otherwise scrambled, after the content has been read by the reader and transferred to the processor or after the medical device has been switched to the second mode. The storage medium may no longer be used to switch the medical device to the second mode after the content has been erased or scrambled. In this manner, the storage medium may be used with any number of medical devices (i.e., a particular medical device does not have to be linked or associated in any way to a unique storage medium or vice versa). Once the content in the storage medium is erased or scrambled, it is no longer usable by the medical device (or any other medical devices) until additional content has been loaded or programmed into the storage medium. Alternatively, the medical device is disposable and no longer usable after the content has been deleted or scrambled.

In some embodiments, the storage medium is card-shaped and the reader is configured to read the content from the storage medium via an RFID technique. In other embodiments, the reader is configured to read the content from the storage medium optically. The content may be a barcode, a QR code or the like and the reader may be configured to read the content from the storage medium electromagnetically.

In some embodiments, the storage medium includes a first content and a second content. The reader is configured to read the first content, the second content or both the first and second contents. In an exemplary embodiment, the processor switches the medical device to the activated mode based on the first content. The first content is then erased or scrambled, but the second content is not erased or scrambled. Alternatively, the processor may be configured to save an identification of the storage medium, such as a UID, such that the first content cannot be used again (i.e., without deleting the first content). In another embodiment, the reader is configured to read both the first and second contents, which are then both deleted or scrambled from the storage medium.

In certain embodiments, the first content may include one or more doses that can be used as, for example, sample doses to be provided to the patient by the physician or caregiver. This configuration allows, for example, the physician or other caregiver to demonstrate use of the device to the patient without erasing or scrambling the second content, which contains the prescribed number of doses and/or time period for the initial therapy. In addition, this configuration may allow the caregiver or patient to sample the device without starting the clock on the time period of the second content (in those embodiments wherein the content includes a time period for the activated mode).

In some embodiments, the system further includes a visual display and user input(s), which may reside on the medical device or on a separate display coupled to the medical device. The visual display may include a time feature, and the processor may be configured to synchronize a time set on the visual display with a desired time (i.e., the patient's local time, or a 24 hour time period that begins at a desired time). In this manner, the caregiver or patient may set the time feature on the medical device to correspond with a time period in the content of the storage medium.

In some embodiments, the reader and/or the processor are configured to transfer data, information or a set of instructions to the storage medium. The storage medium may include a visual display that presents the data or information to a user. For example, the data may include a unique device identification, such as a Bluetooth address for the medical device, that can be transferred to the storage medium and displayed to the user. This allows a user to quickly and easily determine the unique device identification of a medical device by placing the storage medium near or within reading distance of the medical device.

In some embodiments, the content on the storage medium includes a set of instructions, algorithms or programs for the processor and/or the medical device. The reader is configured to read the set of instructions and transfer the instructions to the processor and/or the medical device. The set of instructions may include, for example, instructions to display certain information or data on the visual display of the medical device or a separate visual display. The data may include, for example, the total number of doses administered by the medical device, the number of doses administered over a particular period of time, the average number of doses administered over a time period, the actual time each dose has been administered or other parameters, such as amplitude, voltage or current settings. This configuration allows the patient or a caregiver to monitor use of the device to determine if the patient has complied with a given therapy prescribed by the caregiver.

In some embodiments, the system further includes a software application that can be downloaded onto the processor, the medical device or a separate device, such as a mobile phone, computer, server or the like. The storage medium may include a set of instructions for transferring or downloading data or information from the processor or medical device to the software application. The data or information may be similar to the data provided to the user display or it may include other information stored within the processor, such as the number of doses administered over a time period, the amplitude of each dose, etc. This embodiment allows a user to automatically download dosing or other information from the medical device to, for example, a healthcare application on a mobile phone, simply by reading a set of instructions from the storage medium.

In some embodiments, the storage medium may include data, information or a set of instructions to revise, reset and/or test certain settings, signal parameters, variables, memory, data or information, or to run system diagnostics within, the medical device and/or the processor. The storage medium may include the set of instructions in addition to any of the content described above, or the set of instructions may be the only content on the storage medium. The reader is configured to read and transfer the set of instructions to the processor and/or the medical device. In one exemplary embodiment, the set of instructions may be used to revise or reset desired default settings on the medical device. In another exemplary embodiment, the set of instructions may be used to instruct the medical device and/or processor to run various self-test routines to diagnose internal software and/or hardware or to run system diagnostics during, for example, quality assurance or returns analysis procedures.

In some embodiments, the medical device comprises a nerve stimulation device for modulating one or more nerves within a patient's body to treat a disease, disorder or condition, or the symptoms of a disease, disorder or condition. In these embodiments, the medical device comprises a housing having a contact surface and an electrode coupled to the pulse generator within the housing. The device can also include a power supply that may be located within the housing, or coupled to the power supply through wire or wireless connections. The pulse generator can be configured to transmit the electrical impulse from the electrode(s) through the contact surface transcutaneously and non-invasively through an outer skin surface of a patient such that the electrical impulse is sufficient to modulate a nerve, such as the vagus nerve, within the patient. The electrical impulse is sufficient to cause the vagus nerve to generate an action potential sufficient to treat a medical condition, disease or disorder within the patient.

In another aspect, a method comprises providing a storage medium with a content, causing, via a processor, a reader to read the content and causing, via the processor, a medical device to switch from a first mode to a second mode based on the content.

In some embodiments, the method further includes deleting or scrambling the content from the storage medium after the content has been read or the medical device has been switched to the second mode. Thus, the storage medium may no longer be used to switch the medical device to the second mode after the content has been deleted or scrambled.

In some embodiments, the first mode of the medical device is a deactivated mode and the second mode is an activated mode. The activated mode is configured for a defined time period and/or a defined number of doses such that the medical device will stop working after a defined time period and/or a defined number of doses.

In some embodiments, the storage medium is card-shaped and the method includes reading the content from the storage medium via an RFID technique. In other embodiments, the method includes reading the content from the storage medium optically. The content may be a barcode, a QR code or the like and the reader may be configured to read the content from the storage medium electromagnetically.

In some embodiments, the storage medium includes a first content and a second content. The method further includes reading the first content and causing the medical device to switch from the first mode to the second mode based on the first content. In certain embodiments, the first content is then erased or scrambled, but the second content is not erased or scrambled. Alternatively, an identification of the storage medium, such as a UID, is read into the processor such that the first content cannot be used again (i.e., without deleting the first content). In another embodiment, the method includes reading both the first and second contents, and then erasing or scrambling both the first and second contents from the storage medium.

In some embodiments, a method for treating a disease or disorder in a patient comprises applying energy transcutaneously through an outer skin surface of the patient to generate an electrical impulse at or near a selected nerve, such as the vagus nerve, within the patient. The electrical impulse is sufficient to treat the disorder or at least treat some of the symptoms of such disorder. A reader coupled to the medical device reads a content from a storage medium and causes the medical device to switch from a first mode to a second mode based on the content. In this manner, the medical device may be "filled" with an initial number of doses or an active time period for a patient. The medical device will automatically become deactivated when the patient has completed the prescribed number of doses or time period.

In some embodiments, the method further includes positioning a contact surface of a housing on a handheld device in contact with or near an outer skin surface of a neck of the patient and transmitting an electric current transcutaneously and non-invasively through the outer skin surface of the neck of the patient to generate an electrical impulse at or near the vagus nerve. The housing comprises an energy source for generating the electric current. However, the energy source may be located remotely to the housing in certain embodiments.

Various technologies for preventing, diagnosing, monitoring, ameliorating, or treating medical conditions, diseases, or disorders, are more completely described in the following detailed description, with reference to the drawings provided herewith, and in claims appended hereto. Other aspects, features, advantages, etc. will become apparent to one skilled in the art when the description is taken in conjunction with the accompanying drawings.

INCORPORATION BY REFERENCE

Hereby, all issued patents, published patent applications, and non-patent publications that are mentioned in this specification are herein incorporated by reference in their entirety for all purposes as if copied and pasted herein, to the same extent as if each individual issued patent, published patent application, or non-patent publication were specifically and individually indicated to be incorporated by reference and copied and pasted into this disclosure.

DESCRIPTION OF DRAWINGS

FIG. 2A shows an embodiment of an electrical voltage/current profile for stimulating and/or modulating impulses that are applied to a nerve according to this disclosure.

FIG. 2B illustrates an embodiment of an bursting electrical waveform for stimulating and/or modulating a nerve according to this disclosure.

FIG. 2C illustrates an embodiment of two successive bursts of the waveform of FIG. 2B according to this disclosure.

FIG. 11 illustrates an embodiment of another mechanism of action of a medical device in which sympathetic fibers release norepinephrine into a spleen in close proximity to a specialized group of immune cells that release acetylcholine, or ACh according to this disclosure.

FIGS. 19A-19G show an embodiment of a process of pairing a patient/card and a medical device thereby establishing a master patient/card to device mapping according to this disclosure.

FIGS. 20A-20J show an embodiment of a neurostimulator according to this disclosure.

DETAILED DESCRIPTION

Figure 1A:
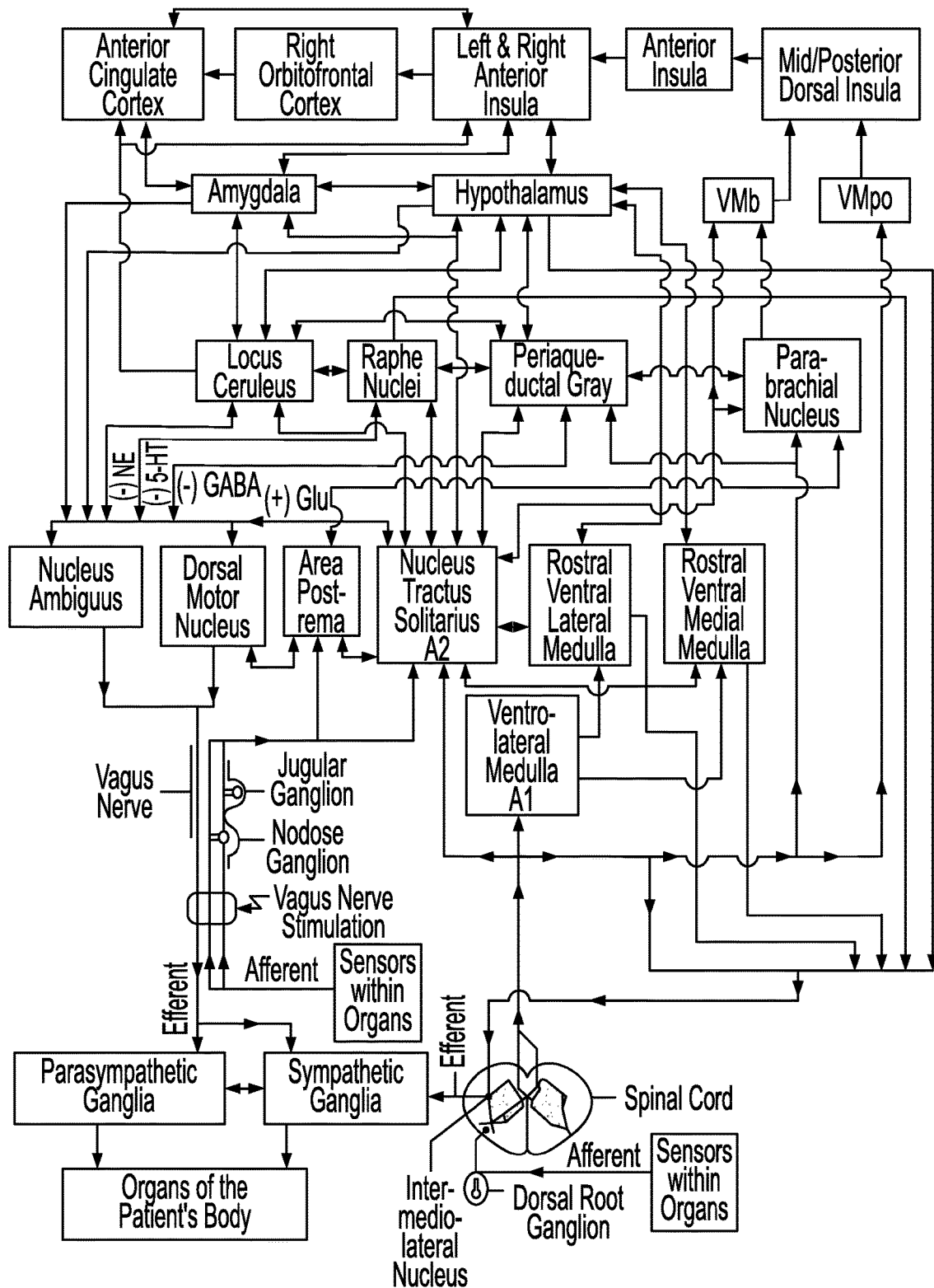
FIG. 1A shows structures within a patient's nervous system that may be modulated by electrical stimulation of a vagus nerve according to this disclosure.

Generally, this disclosure describes a system that includes a medical device, such as a neurostimulator, and a storage medium, such as a RFID card or the like, that includes a content. The medical device includes a processor and a reader that is configured to read the content from a storage medium, and then enable the medical device to be switched from a first mode, such as a deactivated mode, to a second mode, such as an activated mode, based on the content. Note though that this disclosure is now described more fully with reference to the set of accompanying illustrative drawings, in which example embodiments of this disclosure are shown. This disclosure can be embodied in many different forms and should not be construed as necessarily being limited to the example embodiments disclosed herein. Rather, the example embodiments are provided so that this disclosure is thorough and complete, and fully conveys various concepts of this disclosure to those skilled in a relevant art.

For example, this disclose can relate to delivery of energy impulses (and/or fields) to bodily tissues for therapeutic purposes. Some embodiments can relate to devices and methods for treating medical conditions, such as primary headache, autoimmune diseases and disorders and others, where the patient uses the devices and methods as self-treatment, without the direct assistance of a healthcare professional. The energy impulses (and/or fields) that are used to treat those conditions comprise electrical and/or electromagnetic energy, can be delivered invasively or non-invasively to the patient, particularly to a vagus nerve of the patient.

Some limited use of electrical stimulation for treatment of medical conditions may have occurred. One successful application of modern understanding of the electrophysiological relationship between muscle and nerves is a cardiac pacemaker. Although origins of the cardiac pacemaker extend back into the 1800's, it was not until 1950 that the first practical, albeit external and bulky, pacemaker was developed. The first truly functional, wearable pacemaker appeared in 1957, and in 1960, the first fully implantable pacemaker was developed.

Around this time, it was also found that electrical leads could be connected to the heart through veins, which eliminated the need to open the chest cavity and attach the lead to the heart wall. In 1975, the introduction of the lithium-iodide battery prolonged the battery life of a pacemaker from a few months to more than a decade. The modern pacemaker can treat a variety of different signaling pathologies in the cardiac muscle, and can serve as a defibrillator as well (see U.S. Pat. No. 6,738,667 to DENO, et al., the disclosure of which is incorporated herein by reference for all purposes as if copied and pasted herein). Because the leads are implanted within the patient, the pacemaker is an example of an implantable medical device.

Another such example is electrical stimulation of the brain with implanted electrodes (e.g. deep brain stimulation), which has been approved for use in the treatment of various conditions, including pain and movement disorders such as essential tremor and Parkinson's disease [Joel S. PERLMUTTER and Jonathan W. Mink. Deep brain stimulation. Annu. Rev. Neurosci 29 (2006):229-257 the disclosure of which is incorporated herein by reference for all purposes as if copied and pasted herein)].

Another application of electrical stimulation of nerves is the treatment of radiating pain in the lower extremities by stimulating the sacral nerve roots at the bottom of the spinal cord [Paul F. WHITE, Shitong Li and Jen W. Chiu. Electroanalgesia: Its Role in Acute and Chronic Pain Management. Anesth Analg 92(2001):505-513; patent U.S. Pat. No. 6,871,099, entitled Fully implantable microstimulator for spinal cord stimulation as a therapy for chronic pain, to WHITEHURST, et al, the disclosure of which is incorporated herein by reference for all purposes as if copied and pasted herein)].

A form of electrical (or mechanical, thermal, acoustical, photonic, vibratory) stimulation that may be relevant to this disclosure can include invasive or non-invasive nerve stimulation, such as vagus nerve stimulation (VNS, also known as vagal nerve stimulation). It was developed initially for the treatment of partial onset epilepsy and was subsequently developed for the treatment of depression and other disorders. The left vagus nerve is ordinarily stimulated at a location within the neck by first surgically implanting an electrode there and then connecting the electrode to an electrical stimulator [U.S. Pat. No. 4,702,254 entitled Neurocybernetic prosthesis, to ZABARA the disclosure of which is incorporated herein by reference for all purposes as if copied and pasted herein; U.S. Pat. No. 6,341,236 entitled Vagal nerve stimulation techniques for treatment of epileptic seizures, to OSORIO et al, the disclosure of which is incorporated herein by reference for all purposes as if copied and pasted herein; U.S. Pat. No. 5,299,569 entitled Treatment of neuropsychiatric disorders by nerve stimulation, to WERNICKE et al, the disclosure of which is incorporated herein by reference for all purposes as if copied and pasted herein; G. C. ALBERT, C. M. Cook, F. S. Prato, A. W. Thomas. Deep brain stimulation, vagal nerve stimulation and transcranial stimulation: An overview of stimulation parameters and neurotransmitter release. Neuroscience and Biobehavioral Reviews 33 (2009):1042-1060, the disclosure of which is incorporated herein by reference for all purposes as if copied and pasted herein; GROVES D A, Brown V J. Vagal nerve stimulation: a review of its applications and potential mechanisms that mediate its clinical effects. Neurosci Biobehav Rev 29(2005):493-500, the disclosure of which is incorporated herein by reference for all purposes as if copied and pasted herein; Reese TERRY, Jr. Vagus nerve stimulation: a proven therapy for treatment of epilepsy strives to improve efficacy and expand applications. Conf Proc IEEE Eng Med Biol Soc. 2009, 2009:4631-4634, the disclosure of which is incorporated herein by reference for all purposes as if copied and pasted herein; Timothy B. MAPSTONE. Vagus nerve stimulation: current concepts. Neurosurg Focus 25 (3,2008):E9, pp. 1-4, the disclosure of which is incorporated herein by reference for all purposes as if copied and pasted herein; ANDREWS, R. J. Neuromodulation. I. Techniques-deep brain stimulation, vagus nerve stimulation, and transcranial magnetic stimulation. Ann. N. Y. Acad. Sci. 993(2003):1-13, the disclosure of which is incorporated herein by reference for all purposes as if copied and pasted herein; LABINER, D. M., Ahern, G. L. Vagus nerve stimulation therapy in depression and epilepsy: therapeutic parameter settings. Acta. Neurol. Scand. 115(2007): 23-33, the disclosure of which is incorporated herein by reference for all purposes as if copied and pasted herein].

In some embodiments, many such therapeutic applications of electrical stimulation involve the surgical implantation of electrodes within a patient. In contrast, some devices used for the procedures that are disclosed herein do not involve surgery, i.e., they are not implantable medical devices. Instead, some of the present devices and methods stimulate nerves by transmitting energy to nerves and tissue non-invasively. A medical procedure can be understood as being non-invasive when no break in the skin (or other surface of the body, such as a wound bed) is created through use of the method, and when there is no contact with an internal body cavity beyond a body orifice (e.g., beyond the mouth or beyond the external auditory meatus of the ear). In some ways, such non-invasive procedures can be distinguished from some invasive procedures (including minimally invasive procedures) in that the invasive procedures insert a substance or device into or through the skin (or other surface of the body, such as a wound bed) or into an internal body cavity beyond a body orifice.

For example, transcutaneous electrical stimulation of a nerve can be non-invasive because it involves attaching electrodes to the skin, or otherwise stimulating at or beyond the surface of the skin or using a form-fitting conductive garment, without breaking the skin [Thierry KELLER and Andreas Kuhn. Electrodes for transcutaneous (surface) electrical stimulation. Journal of Automatic Control, University of Belgrade 18(2,2008):35-45, the disclosure of which is incorporated herein by reference for all purposes as if copied and pasted herein; Mark R. PRAUSNITZ. The effects of electric current applied to skin: A review for transdermal drug delivery. Advanced Drug Delivery Reviews 18 (1996) 395-425, the disclosure of which is incorporated herein by reference for all purposes as if copied and pasted herein]. In contrast, percutaneous electrical stimulation of a nerve can be minimally invasive because it involves the introduction of an electrode under the skin, via needle-puncture of the skin.

Another form of non-invasive electrical stimulation is magnetic stimulation. It involves the induction, by a time-varying magnetic field, of electrical fields and current within tissue, in accordance with Faraday's law of induction. Magnetic stimulation can be non-invasive because the magnetic field is produced by passing a time-varying current through a coil positioned outside the body. An electric field is induced at a distance, causing electric current to flow within electrically conducting bodily tissue. The electrical circuits for magnetic stimulators can be generally complex and expensive and use a high current impulse generator that may produce discharge currents of 5,000 amps or more, which is passed through the stimulator coil to produce a magnetic pulse. Some principles of electrical nerve stimulation using a magnetic stimulator, along with descriptions of medical applications of magnetic stimulation, are reviewed in: Chris HOVEY and Reza Jalinous, The Guide to Magnetic Stimulation, The Magstim Company Ltd, Spring Gardens, Whitland, Carmarthenshire, SA34 0 HR, United Kingdom, 2006, the disclosure of which is incorporated herein by reference for all purposes as if copied and pasted herein. In contrast, the magnetic stimulators that are disclosed herein are relatively simpler devices that can use considerably smaller currents within the stimulator coils. Accordingly, they are intended to satisfy a need for simple-to-use and less expensive non-invasive magnetic stimulation devices.

Some advantages of some of such non-invasive medical methods and devices relative to comparable invasive procedures are as follows. The patient may be more psychologically prepared to experience a procedure that is non-invasive and may therefore be more cooperative, resulting in a better outcome. Non-invasive procedures may avoid damage of biological tissues, such as that due to bleeding, infection, skin or internal organ injury, blood vessel injury, and vein or lung blood clotting. Non-invasive procedures can be generally measurably painless and may be performed without some of the dangers and costs of surgery. They are ordinarily performed even without the need for local anesthesia. Less training may be required for use of non-invasive procedures by medical professionals. In view of the reduced risk ordinarily associated with non-invasive procedures, some such procedures may be suitable for use by the patient or family members at home or by first-responders at home or at a workplace. Furthermore, the cost of non-invasive procedures may be significantly reduced relative to comparable invasive procedures.

In co-pending, commonly assigned patent applications, the Applicant disclosed some noninvasive electrical vagus nerve stimulation devices, which are adapted, and for certain applications improved, in the present disclosure: application Ser. No. 12/859,568, filed Aug. 19, 2010 (now U.S. Pat. No. 9,037,247); application Ser. No. 12/964,050, filed Dec. 9, 2010 (now U.S. Pat. No. 8,972,004); application Ser. No. 13/004,005, filed Jan. 12, 2011 (now U.S. Pat. No. 8,868, 177), application Ser. No. 13/075,746, filed Mar. 30, 2011 (now U.S. Pat. No. 8,874,205); application Ser. No. 13/183, 721, filed Jul. 15, 2011 (now U.S. Pat. No. 8,676,324); application Ser. No. 13/222,087, filed Aug. 31, 2011 (now U.S. Pat. No. 9,174,066); application Ser. No. 14/286,412, filed May 23, 2014 (now U.S. Pat. No. 9,566,426); application Ser. No. 13/603,781, filed Sep. 5, 2012 (now U.S. Pat. No. 8,983,628) application Ser. No. 13/858,114, filed Apr. 8, 2013 (now U.S. Pat. No. 9,248,286); and application Ser. No. 14/292,491, filed May 30, 2014 (now U.S. Pat. No. 9,375,571), the disclosures of all of which are incorporated herein by reference for all purposes as if copied and pasted herein; and other co-pending commonly assigned applications that are cited therein, the disclosure of which is incorporated herein by reference for all purposes as if copied and pasted herein.

At least some of the present disclosure elaborates on the electrical stimulation device, rather than the magnetic stimulation device that has similar functionality, with the understanding that unless it is otherwise indicated, the elaboration could apply to either the electrical or the magnetic nerve stimulation device. Because some properties of some of the earlier devices have already been disclosed, the present disclosure focuses on what is new with respect to the earlier disclosures.

The patient can apply the stimulator without the benefit of having a trained healthcare provider nearby. An advantage of the self-stimulation therapy is that it can be administered more or less immediately when symptoms occur, rather than having to visit the healthcare provider at a clinic or emergency room. A need for such a visit would only compound the aggravation that the patient is already experiencing. Another advantage of the self-stimulation therapy is the convenience of providing the therapy in the patient's home or workplace, which eliminates scheduling difficulties, for example, when the nerve stimulation is being administered for prophylactic reasons at odd hours of the day. Furthermore, the cost of the treatment may be reduced by not requiring the involvement of a trained healthcare provider.

The present disclosure discloses methods and devices for the non-invasive treatment of diseases and disorders, utilizing an energy source that transmits energy non-invasively to nervous tissue. In particular, the devices can transmit energy to, or in close proximity to, a nerve of the patient, such as the vagus nerve, in order to temporarily stimulate, block and/or modulate electrophysiological signals in that nerve. In some embodiments, some electrodes applied to the skin of the patient generate currents within the tissue of the patient. This may enable production and application of the electrical impulses so as to interact with the signals of one or more nerves, in order to achieve the therapeutic result. Some of the disclosure is directed specifically to treatment of a patient by stimulation in or around a vagus nerve, with devices positioned non-invasively on or near a patient's neck. However, other medical devices, techniques, and modalities of prevention, diagnosis, monitoring, amelioration, or treatment of various medical conditions, disorders, or diseases are disclosed herein as well.

FIG. 1A shows an embodiment of a location of a stimulation as "Vagus Nerve Stimulation," relative to its connections with other anatomical structures that are potentially affected by the stimulation. In some embodiments, various brain and brainstem structures are modulated by the stimulation. These structures are described in sections of the disclosure that follow, along with some rationale for modulating their activity as a prevention, prophylaxis, diagnosis, monitoring, amelioration, or treatment of various medical conditions, diseases or disorders.

For example, some systems and methods can be configured to prevent, diagnose, monitor, ameliorate, or treat a neurological condition, such as epilepsy, headache/migraine, whether primary or secondary, whether cluster or tension, neuralgia, seizures, vertigo, dizziness, concussion, aneurysm, palsy, Parkinson's disease, Alzheimer's disease, or others, as understood to skilled artisans and which are only omitted here for brevity. For example, some systems and methods can be configured to prevent, diagnose, monitor, ameliorate, or treat a neurodegenerative disease, such as Alzheimer's disease, Parkinson's disease, multiple sclerosis, postoperative cognitive dysfunction, and postoperative delirium, or others, as understood to skilled artisans and which are only omitted here for brevity. For example, some systems and methods can be configured to prevent, diagnose, monitor, ameliorate, or treat an inflammatory disease or disorder, such as Alzheimer's disease, ankylosing spondylitis, arthritis (osteoarthritis, rheumatoid arthritis (RA), Sjôgren's syndrome, temporal arteritis, Type 2 diabetes, psoriatic arthritis, asthma, atherosclerosis, Crohn's disease, colitis, dermatitis, diverticulitis, fibromyalgia, hepatitis, irritable bowel syndrome (IBS), systemic lupus erythematous (SLE), nephritis, fibromyalgia, Celiac disease, Parkinson's disease, ulcerative colitis, chronic peptic ulcer, tuberculosis, periodontitis, sinusitis, hepatitis, Graves disease, psoriasis, pernicious anemia (PA), peripheral neuropathy, lupus or others, as understood to skilled artisans and which are only omitted here for brevity. For example, some systems and methods can be configured to prevent, diagnose, monitor, ameliorate, or treat a gastrointestinal condition, such as ileus, irritable bowel syndrome, Crohn's disease, ulcerative colitis, diverticulitis, gastroesophageal reflux disease, or others, as understood to skilled artisans and which are only omitted here for brevity. For example, some systems and methods can be configured to prevent, diagnose, monitor, ameliorate, or treat a bronchial disorder, such as asthma, bronchitis, pneumonia, or others, as understood to skilled artisans and which are only omitted here for brevity. For example, some systems and methods can be configured to prevent, diagnose, monitor, ameliorate, or treat a coronary artery disease, heart attack, arrhythmia, cardiomyopathy, or others, as understood to skilled artisans and which are only omitted here for brevity. For example, some systems and methods can be configured to prevent, diagnose, monitor, ameliorate, or treat a urinary disorder, such as urinary incontinence, urinalysis, overactive bladder, or others, as understood to skilled artisans and which are only omitted here for brevity. For example, some systems and methods can be configured to prevent, diagnose, monitor, ameliorate, or treat eat a cancer, such as bladder cancer, breast cancer, prostate cancer, lung cancer, colon or rectal cancer, skin cancer, thyroid cancer, brain cancer, leukemia, liver cancer, lymphoma, pancreatic cancer, or others, as understood to skilled artisans and which are only omitted here for brevity. For example, some systems and methods can be configured to prevent, diagnose, monitor, ameliorate, or treat a metabolic disorder, such as diabetes (type 1, type 2, or gestational), Gaucher's disease, sick cell anemia, cystic fibrosis, hemochromatosis, or others, as understood to skilled artisans and which are only omitted here for brevity.

In some embodiments, various brain and brainstem structures are preferentially modulated by the stimulation. Some of these structures are described in sections of the disclosure that follow, along with the rationale for modulating their activity as a prophylaxis or treatment of autoimmune diseases, such as Alzheimer's disease, Parkinson's disease, multiple sclerosis, Rheumatoid arthritis, Sjôgren's syndrome, temporal arteritis, Type 2 diabetes, Addison's disease, amyloidosis, Celiac disease, fibromyalgia, Graves disease, psoriasis, pernicious anemia (PA), peripheral neuropathy, lupus, Crohn's disease and the like.

As a preliminary matter, we first describe the vagus nerve itself and its most proximal connections, which are relevant to the disclosure below of the electrical waveforms that may be used to perform some of the stimulation. A fact that electrical stimulation of a vagus nerve can be used to treat many disorders may be understood as follows. The vagus nerve is composed of motor and sensory fibers. The vagus nerve leaves the cranium, passes down the neck within the carotid sheath to the root of the neck, then passes to the chest and abdomen, where it contributes to the innervation of the viscera. A human vagus nerve (tenth cranial nerve, paired left and right) comprises of over 100,000 nerve fibers (axons), mostly organized into groups. The groups are contained within fascicles of varying sizes, which branch and converge along the nerve. Under normal physiological conditions, each fiber conducts electrical impulses only in one direction, which is defined to be the orthodromic direction, and which is opposite the antidromic direction. However, external electrical stimulation of the nerve may produce action potentials that propagate in orthodromic and antidromic directions. Besides efferent output fibers that convey signals to the various organs in the body from the central nervous system, the vagus nerve conveys sensory (afferent) information about the state of the body's organs back to the central nervous system. Some 80-90% of the nerve fibers in the vagus nerve are afferent (sensory) nerves, communicating the state of the viscera to the central nervous system.

The largest nerve fibers within a left or right vagus nerve are approximately 20 μm in diameter and are heavily myelinated, whereas only the smallest nerve fibers of less than about 1 μm in diameter are completely unmyelinated. When the distal part of a nerve is electrically stimulated, a compound action potential may be recorded by an electrode located more proximally. A compound action potential contains several peaks or waves of activity that represent the summated response of multiple fibers having similar conduction velocities. The waves in a compound action potential represent different types of nerve fibers that are classified into corresponding functional categories, with approximate diameters as follows: A-alpha fibers (afferent or efferent fibers, 12-20 μm diameter), A-beta fibers (afferent or efferent fibers, 5-12 μm), A-gamma fibers (efferent fibers, 3-7 μm), A-delta fibers (afferent fibers, 2-5 μm), B fibers (1-3 μm) and C fibers (unmyelinated, 0.4-1.2 μm). The diameters of group A and group B fibers include the thickness of the myelin sheaths.

The vagus (or vagal) afferent nerve fibers arise from cell bodies located in the vagal sensory ganglia, which take the form of swellings near the base of the skull. Vagal afferents traverse the brainstem in the solitary tract, with some eighty percent of the terminating synapses being located in the nucleus of the tractus solitarius (or nucleus tractus solitarii, nucleus tractus solitarius, or NTS). The NTS projects to a wide variety of structures in the central nervous system, such as the amygdala, raphe nuclei, periaqueductal gray, nucleus paragigantocellurlais, olfactory tubercule, locus ceruleus, nucleus ambiguus and the hypothalamus. The NTS also projects to the parabrachial nucleus, which in turn projects to the hypothalamus, the thalamus, the amygdala, the anterior insula, and infralimbic cortex, lateral prefrontal cortex, and other cortical regions [JEAN A. The nucleus tractus solitarius: neuroanatomic, neurochemical and functional aspects. Arch Int Physiol Biochim Biophys 99(5,1991):A3-A52 the disclosure of which is incorporated herein by reference for all purposes as if copied and pasted herein]. Thus, stimulation of vagal afferents can modulate the activity of many structures of the brain and brainstem through these projections.

With regard to vagal efferent nerve fibers, two vagal components have evolved in the brainstem to regulate peripheral parasympathetic functions. The dorsal vagal complex, consisting of the dorsal motor nucleus and its connections controls parasympathetic function primarily below the level of the diaphragm, while the ventral vagal complex, comprised of nucleus ambiguus and nucleus retrofacial, controls functions primarily above the diaphragm in organs such as the heart, thymus and lungs, as well as other glands and tissues of the neck and upper chest, and specialized muscles such as those of the esophageal complex. For example, the cell bodies for the preganglionic parasympathetic vagal neurons that innervate the heart reside in the nucleus ambiguus, which is relevant to potential cardiovascular side effects that may be produced by vagus nerve stimulation.

The vagus efferent fibers innervate parasympathetic ganglionic neurons that are located in or adjacent to each target organ. The vagal parasympathetic tone resulting from the activity of these fibers is balanced reflexively in part by sympathetic innervations. Consequently, electrical stimulation of a vagus nerve may result not only in modulation of parasympathetic activity in postganglionic nerve fibers, but also a reflex modulation of sympathetic activity. The ability of a vagus nerve to bring about widespread changes in autonomic activity, either directly through modulation of vagal efferent nerves, or indirectly via activation of brainstem and brain functions that are brought about by electrical stimulation of vagal afferent nerves, accounts for the fact that vagus nerve stimulation can treat many different medical conditions in many end organs. Selective treatment of particular conditions is possible because the parameters of the electrical stimulation (e.g. frequency, amplitude, pulse width, etc.) may selectively activate or modulate the activity of particular afferent or efferent A, B, and/or C fibers that result in a particular physiological response in each individual.

The electrodes used to stimulate a vagus nerve can be implanted about the nerve during open neck surgery. For many patients, this may be done with an objective of implanting permanent electrodes to treat epilepsy, depression, or other conditions [Arun Paul AMAR, Michael L. Levy, Charles Y. Liu and Michael L. J. Apuzzo. Chapter 50. Vagus nerve stimulation. pp. 625-638, the disclosure of which is incorporated herein by reference for all purposes as if copied and pasted herein. In: Elliot S. Krames, P. Hunber Peckham, Ali R. Rezai, eds. Neuromodulation. London: Academic Press, 2009, the disclosure of which is incorporated herein by reference for all purposes as if copied and pasted herein; KIRSE D J, Werle A H, Murphy J V, Eyen T P, Bruegger D E, Hornig G W, Torkelson R D. Vagus nerve stimulator implantation in children. Arch Otolaryngol Head Neck Surg 128(11,2002):1263-1268, the disclosure of which is incorporated herein by reference for all purposes as if copied and pasted herein]. In that case, the electrode can be a spiral electrode, although other designs may be used as well [U.S. Pat. No. 4,979,511, entitled Strain relief tether for implantable electrode, to TERRY, Jr., the disclosure of which is incorporated herein by reference for all purposes as if copied and pasted herein; U.S. Pat. No. 5,095,905, entitled Implantable neural electrode, to KLEPINSKI, the disclosure of which is incorporated herein by reference for all purposes as if copied and pasted herein]. In other patients, a vagus nerve can be electrically stimulated during an open-neck thyroid surgery in order to confirm that the nerve has not been accidentally damaged during the surgery. In that case, a vagus nerve in the neck is surgically exposed, and a temporary stimulation electrode is clipped about the nerve [SCHNEIDER R, Randolph G W, Sekulla C, Phelan E, Thanh P N, Bucher M, Machens A, Dralle H, Lorenz K. Continuous intraoperative vagus nerve stimulation for identification of imminent recurrent laryngeal nerve injury. Head Neck. 2012 Nov. 20. doi: 10.1002/hed.23187 (Epub ahead of print, pp. 1-8), the disclosure of which is incorporated herein by reference for all purposes as if copied and pasted herein].

It is also possible to electrically stimulate a vagus nerve using a minimally invasive surgical approach, namely percutaneous nerve stimulation. In that procedure, a pair of electrodes (an active and a return electrode) are introduced through the skin of a patient's neck to the vicinity of a vagus nerve, and wires connected to the electrodes extend out of the patient's skin to a pulse generator [Publication number US20100241188, entitled Percutaneous electrical treatment of tissue, to J. P. ERRICO et al., the disclosure of which is incorporated herein by reference for all purposes as if copied and pasted herein; SEPULVEDA P, Bohill G, Hoffmann T J. Treatment of asthmatic bronchoconstriction by percutaneous low voltage vagal nerve stimulation: case report. Internet J Asthma Allergy Immunol 7(2009):e1 (pp 1-6), the disclosure of which is incorporated herein by reference for all purposes as if copied and pasted herein; MINER, J. R., Lewis, L. M., Mosnaim, G. S., Varon, J., Theodoro, D. Hoffman, T. J. Feasibility of percutaneous vagus nerve stimulation for the treatment of acute asthma exacerbations. Acad Emerg Med 2012; 19: 421-429, the disclosure of which is incorporated herein by reference for all purposes as if copied and pasted herein].

Percutaneous nerve stimulation procedures has been somewhat described primarily for the treatment of pain, but not for a vagus nerve, which is ordinarily not considered to produce pain and which presents special challenges [HUNTOON M A, Hoelzer B C, Burgher A H, Hurdle M F, Huntoon E A. Feasibility of ultrasound-guided percutaneous placement of peripheral nerve stimulation electrodes and anchoring during simulated movement: part two, upper extremity. Reg Anesth Pain Med 33(6,2008):558-565, the disclosure of which is incorporated herein by reference for all purposes as if copied and pasted herein; CHAN I, Brown A R, Park K, Winfree C J. Ultrasound-guided, percutaneous peripheral nerve stimulation: technical note. Neurosurgery 67(3 Suppl Operative,2010):ons136-139, the disclosure of which is incorporated herein by reference for all purposes as if copied and pasted herein; MONTI E. Peripheral nerve stimulation: a percutaneous minimally invasive approach. Neuromodulation 7(3,2004):193-196, the disclosure of which is incorporated herein by reference for all purposes as if copied and pasted herein; Konstantin V SLAVIN. Peripheral nerve stimulation for neuropathic pain. US Neurology 7(2,2011):144-148, the disclosure of which is incorporated herein by reference for all purposes as if copied and pasted herein].

In some embodiments, a stimulation device is introduced through a percutaneous penetration in the patient to a target location within, adjacent to, or in close proximity with, the carotid sheath that contains the vagus nerve. Once in position, electrical impulses are applied through the electrodes of the stimulation device to one or more selected nerves (e.g., vagus nerve or one of its branches) to stimulate, block or otherwise modulate the nerve(s) and treat the patient's condition or a symptom of that condition. For some conditions, the treatment may be acute, meaning that the electrical impulse immediately begins to interact with one or more nerves to produce a response in the patient. In some cases, the electrical impulse will produce a response in the nerve(s) to improve the patient's condition or symptom in less than 3 hours, preferably less than 1 hour and more preferably less than 15 minutes. For other conditions, intermittently scheduled or as-needed stimulation of the nerve may produce improvements in the patient over the course of several hours, days, weeks, months or years. A more complete description of a suitable percutaneous procedure for vagal nerve stimulation can be found in commonly assigned, co-pending U.S. patent application titled "Percutaneous Electrical Treatment of Tissue", filed Apr. 13, 2009 (Ser. No. 12/422,483), the disclosure of which is incorporated herein by reference for all purposes as if copied and pasted herein.

In some embodiments, a time-varying magnetic field, originating and confined to the outside of a patient, generates an electromagnetic field and/or induces eddy currents within tissue of the patient. In some embodiments, electrodes applied to the skin of the patient generate currents within the tissue of the patient. In some embodiments, an objective may include an ability to produce and apply the electrical impulses so as to interact with the signals of one or more nerves, in order to prevent or avert a stroke and/or transient ischemic attack, to ameliorate or limit the effects of an acute stroke or transient ischemic attack, and/or to rehabilitate a stroke patient.

Some of the disclosure is directed specifically to treatment of a patient by electromagnetic stimulation in or around a vagus nerve, with devices positioned non-invasively on or near a patient's neck. However, it will also be appreciated that some the devices and methods can be applied to other tissues and nerves of the body, including but not limited to other parasympathetic nerves, sympathetic nerves, spinal or cranial nerves. As recognized by those having skill in the art, the methods should be carefully evaluated prior to use in patients known to have preexisting cardiac issues. In addition, it will be recognized that some of the treatment paradigms can be used with a variety of different vagal nerve stimulators, including implantable and/or percutaneous stimulation devices, such as the ones described herein.

In some embodiments, broadly speaking, the Applicant has determined that there are several, such as three, components to the effects of nVNS on the brain. For example, the strongest effect occurs during the two minute stimulation and results in significant changes in brain function that can be clearly seen as acute changes in autonomic function (e.g. measured using pupillometry, heart rate variability, galvanic skin response, or evoked potential) and activation and inhibition of various brain regions as shown in fMRI imaging studies. For example, the second effect, of moderate intensity, lasts for 15 to 180 minutes after stimulation. Animal studies have shown changes in neurotransmitter levels in various parts of the brain that persist for several hours. For example, the third effect, of mild intensity, lasts up to 8 hours and is responsible for the long lasting alleviation of symptoms seen clinically and, for example, in animal models of migraine headache and autoimmune diseases, such as Sjôgren's syndrome and Rheumatoid arthritis or RA.

Thus, depending on the medical indication, whether it is a chronic or acute usage, such as treatment, and the natural history of the disease, different usage, such as treatment, protocols may be used. In particular, the Applicant has discovered that it is not necessary to "continuously stimulate" the vagus nerve (or to in order to provide clinically efficacious benefits to patients with certain disorders. In some embodiments, a term "continuously stimulate" can be understood to mean stimulation that follows a certain On/Off pattern continuously 24 hours/day. For example, some implantable vagal nerve stimulators "continuously stimulate" the vagus nerve with a pattern of 30 seconds ON/5 minutes OFF (or the like) for 24 hours/day and seven days/week. The Applicant has determined that this continuous stimulation is not necessary to provide the desired clinical benefit for many disorders. For example, in the treatment of acute migraine attacks, the treatment paradigm may comprise two minutes of stimulation at the onset of pain, followed by another two-minute stimulation 15 minutes later. For epilepsy, three 2-minute stimulations three times per day appear to be optimal. Sometimes, multiple consecutive, two minute stimulations are required. Thus, the initial treatment protocol corresponds to what may be optimum for the population of patients at large for a given condition. However, the treatment may then be modified on an individualized basis, depending on the response of each particular patient.

In some embodiments, there may be several interventions. For example, there may be three types of interventions involving stimulation of a vagus nerve: prophylactic, acute and compensatory (rehabilitative). Among these, the acute treatment involves the fewest administrations of vagus nerve stimulations, which begin upon the appearance of symptoms. It is intended primarily to enlist and engage the autonomic nervous system to inhibit excitatory neurotransmissions that accompany the symptoms. The prophylactic treatment resembles the acute treatment in the sense that it is administered as though acute symptoms had just occurred (even though they have not) and is repeated at regular intervals, as though the symptoms were reoccurring (even though they are not). The rehabilitative or compensatory treatments, on the other hand, seek to promote long-term adjustments in the central nervous system, compensating for deficiencies that arose as the result of the patient's disease by making new neural circuits.

In some embodiments, a vagus nerve stimulation treatment is conducted for continuous period of thirty seconds to five minutes, such about 90 seconds to about three minutes or about two minutes (each defined as a single dose) or others, each individually inclusive between thirty seconds to five minutes. After a dose has been completed, the therapy is stopped for a period of time (depending on the treatment as described below). For prophylactic treatments, such as a treatment to reduce systemic inflammation in Sjôgren's syndrome or treatments to reduce inflammation in certain locations of the body, such as the joints in Rheumatoid Arthritis, the therapy can comprise multiple doses/day over a period of time that may last from one week to a number of years. In some embodiments, a treatment comprises multiple doses at predetermined times during the day and/or at predetermined intervals throughout the day. In some embodiments, a treatment comprises least one of the following: (1) 3 doses/day at predetermined intervals or times; (2) two doses, either consecutively, or separated by 5 min at predetermined intervals or times, preferably two or three times/day; (3) 3 doses, either consecutively or separated by 5 min again at predetermined intervals or times, such as 2 or 3 times/day; or (4) 1-3 doses, either consecutively or separated by 5 min, 4-6 times per day. Initiation of a treatment may begin, for example, when pain or loss of mobility from inflammation occurs, or in a risk factor reduction program it may be performed throughout the day beginning after the patient arises in the morning.

In some embodiments, each treatment session comprises 1-3 doses administered to the patient either consecutively or separated by 5 minutes. The treatment sessions are administered every 15, 30, 60 or 120 minutes during the day such that the patient could receive 2 doses every hour throughout a 24-hour day.

In some embodiments, for some disorders, the time of day can be more important than the time interval between treatments. For example, the locus coeruleus has periods of time during a 24-hour day wherein it has inactive periods and active periods. Typically, the inactive periods can occur in the late afternoon or in the middle of the night when the patient is asleep. It is during the inactive periods that the levels of inhibitory neurotransmitters in the brain that are generated by the locus coeruleus are reduced. This may have an impact on certain disorders. For example, patients suffering from migraines or cluster headaches often receive these headaches after an inactive period of the locus coeruleus. For these types of disorders, the prophylactic treatment is optimal during the inactive periods such that the amounts of inhibitory neurotransmitters in the brain can remain at a higher enough level to mitigate or abort an acute attack of the disorder.

In these embodiments, the prophylactic treatment may comprise multiple doses/day timed for periods of inactivity of the locus coeruleus. In some embodiments, a treatment comprises one or more doses administered 2-3 times per day or 2-3 "treatment sessions" per day. The treatment sessions preferably occur during the late afternoon or late evening, in the middle of the night and again in the morning when the patient wakes up. In some embodiments, each treatment session comprises 1-4 doses, preferably 2-3 doses, with each dose lasting for about 90 seconds to about three minutes.

For other or some disorders, the intervals between treatment sessions may be the most important as the Applicant has determined that stimulation of the vagus nerve can have a prolonged effect on the inhibitor neurotransmitters levels in the brain, e.g., at least one hour, up to 3 hours and sometimes up to 8 hours. In some embodiments, a treatment comprises one or more doses (i.e., treatment sessions) administered at intervals during a 24-hour period. In some embodiments, there are 1-5 such treatment sessions, preferably 2-4 treatment sessions. Each treatment session preferably comprises 1-3 doses, each lasting between about 60 seconds to about three minutes, preferably about 90 seconds to about 150 seconds, more preferably about 2 minutes.

For an acute treatment, such as treatment of acute pain associated with an autoimmune disorder, a therapy may comprise at least one of: (1) 1 dose at the onset of symptoms; (2) 1 dose at the onset of symptoms, followed by another dose at 5-15 min; or (3) 1 dose every 15 minutes to 1 hour at the onset of symptoms until the acute attack has been mitigated or aborted. In these embodiments, each dose can last between about 60 seconds to about three minutes, preferably about 90 seconds to about 150 seconds, more preferably about 2 minutes.

For long term treatment of an acute insult such as one that occurs during the treatment of systemic autoimmune diseases, a therapy may include at least one of: (1) 3 treatments/day; (2) 2 treatments, either consecutively or separated by 5 min, 3×/day; (3) 3 treatments, either consecutively or separated by 5 min, 2×/day; (4) 2 or 3 treatments, either consecutively or separated by 5 min, up to 10×/day; or (5) 1, 2 or 3 treatments, either consecutively or separated by 5 min, every 15, 30, 60 or 120 min.

For some, many, most, or all of the treatments listed above, one may alternate treatment between left and right sides, or in the case of autoimmune diseases that occur in particular brain hemispheres, one may treat ipsilateral or contralateral to the stroke-hemisphere or headache side, respectively. Or for a single treatment, one may treat one minute on one side followed by one minute on the opposite side. Variations of these treatment paradigms may be chosen on a patient-by-patient basis. However, it is understood that parameters of the stimulation protocol may be varied in response to heterogeneity in the symptoms of patients. Different stimulation parameters may also be selected as the course of the patient's condition changes. In some embodiments, some methods and devices do not produce clinically significant side effects, such as agitation or anxiety, or changes in heart rate or blood pressure.

In some embodiments, some of the prophylactic treatments may be most effective when the patient is in a prodromal, high-risk bistable state. In that state, the patient is simultaneously able to remain normal or exhibit symptoms, and the selection between normal and symptomatic states depends on the amplification of fluctuations by physiological feedback networks. For example, a thrombus may exist in either a gel or fluid phase, with the feedback amplification of fluctuations driving the change of phase and/or the volume of the gel phase. Thus, a thrombus may form or not, depending on the nonlinear dynamics exhibited by the network of enzymes involved in clot formation, as influenced by blood flow and inflammation that may be modulated by vagus nerve stimulation [PANTELEEV M A, Balandina A N, Lipets E N, Ovanesov M V, Ataullakhanov F I. Task-oriented modular decomposition of biological networks: trigger mechanism in blood coagulation. Biophys J 98(9,2010):1751-1761, the disclosure of which is incorporated herein by reference for all purposes as if copied and pasted herein; Alexey M SHIBEKO, Ekaterina S Lobanova, Mikhail A Panteleev and Fazoil I Ataullakhanov. Blood flow controls coagulation onset via the positive feedback of factor VII activation by factor Xa. BMC Syst Biol 2010; 4(2010): 5, pp. 1-12, the disclosure of which is incorporated herein by reference for all purposes as if copied and pasted herein]. Consequently, some of the mechanisms of vagus nerve stimulation treatment during prophylaxis for a stroke are generally different than what occurs during an acute treatment, when the stimulation inhibits excitatory neurotransmission that follows the onset of ischemia that is already caused by the thrombus. Nevertheless, the prophylactic treatment may also inhibit excitatory neurotransmission so as to limit the excitation that would eventually occur upon formation of a thrombus, and the acute treatment may prevent the formation of another thrombus.

Some of the circuits involved in such inhibition are illustrated in FIG. 1A. Excitatory nerves within the dorsal vagal complex generally use glutamate as their neurotransmitter. To inhibit neurotransmission within the dorsal vagal complex, this disclosure makes use of the bidirectional connections that the nucleus of the solitary tract (NTS) has with structures that produce inhibitory neurotransmitters, or it makes use of connections that the NTS has with the hypothalamus, which in turn projects to structures that produce inhibitory neurotransmitters. The inhibition is produced as the result of the stimulation waveforms that are described below. Thus, acting in opposition to glutamate-mediated activation by the NTS of the area postrema and dorsal motor nucleus are: GABA, and/or serotonin, and/or norepinephrine from the periaqueductal gray, raphe nuclei, and locus coeruleus, respectively. FIG. 1A shows how those excitatory and inhibitory influences combine to modulate the output of the dorsal motor nucleus. Similar influences combine within the NTS itself, and the combined inhibitory influences on the NTS and dorsal motor nucleus produce a general inhibitory effect.

The activation of inhibitory circuits in the periaqueductal gray, raphe nuclei, and locus coeruleus by the hypothalamus or NTS may also cause circuits connecting each of these structures to modulate one another. Thus, the periaqueductal gray communicates with the raphe nuclei and with the locus coeruleus, and the locus coeruleus communicates with the raphe nuclei, as shown in FIG. 1A [PUDOVKINA O L, Cremers T I, Westerink B H. The interaction between the locus coeruleus and dorsal raphe nucleus studied with dual-probe microdialysis. Eur J Pharmacol 7(2002), 445(1-2):37-42, the disclosure of which is incorporated herein by reference for all purposes as if copied and pasted herein; REICHLING D B, Basbaum A I. Collateralization of periaqueductal gray neurons to forebrain or diencephalon and to the medullary nucleus raphe magnus in the rat. Neuroscience 42(1,1991):183-200, the disclosure of which is incorporated herein by reference for all purposes as if copied and pasted herein; BEHBEHANI M M. The role of acetylcholine in the function of the nucleus raphe magnus and in the interaction of this nucleus with the periaqueductal gray. Brain Res 252(2,1982):299-307, the disclosure of which is incorporated herein by reference for all purposes as if copied and pasted herein]. The periaqueductal gray, raphe nuclei, and locus coeruleus also project to many other sites within the brain, including those that would be excited during acute or chronic inflammation.

Description of Various Nerve Stimulating/Modulating Devices

Figure 1B:
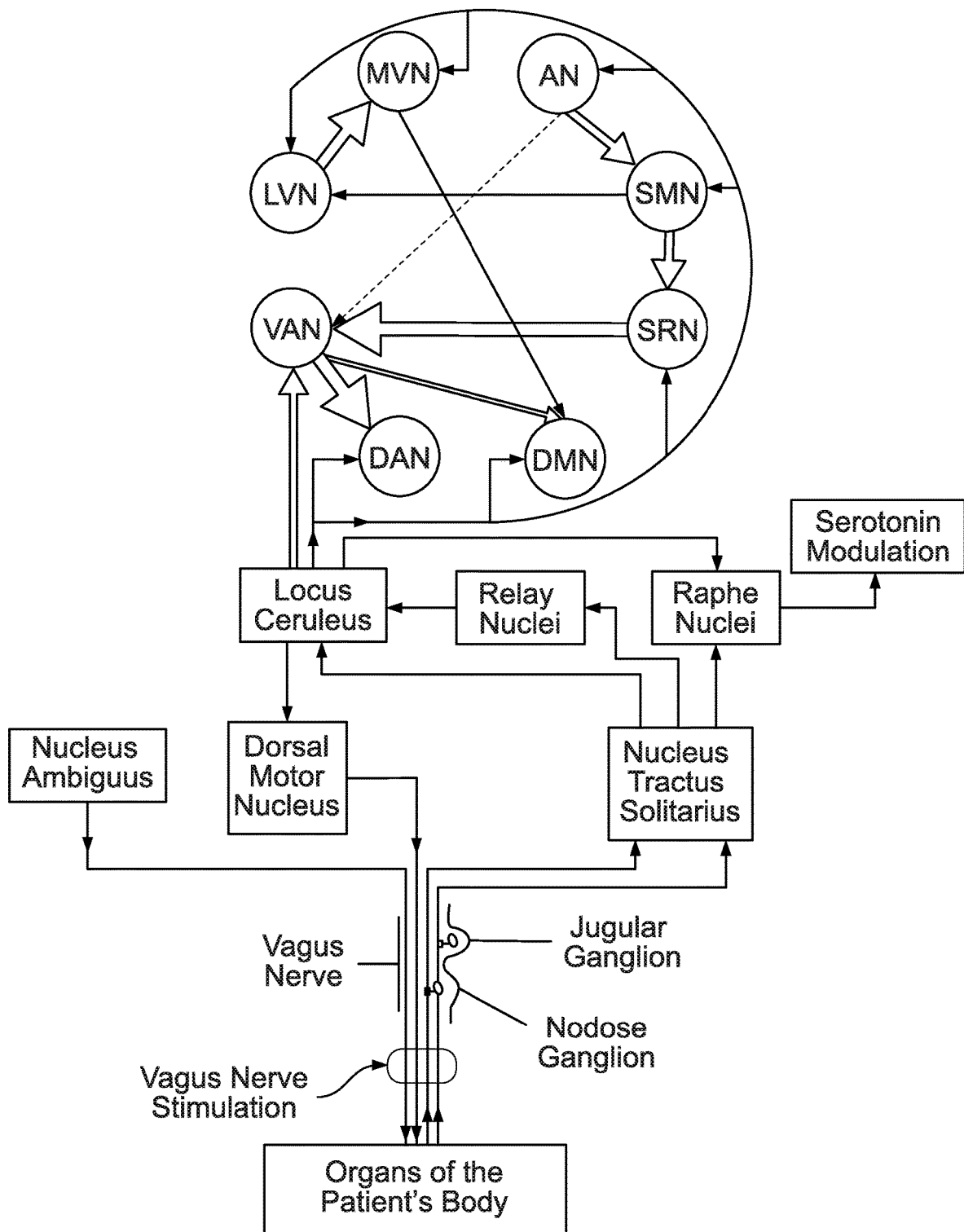
FIG. 1B shows functional networks within the brain (resting state networks) that may be modulated by electrical stimulation of a vagus nerve according to this disclosure.
Figure 1C:
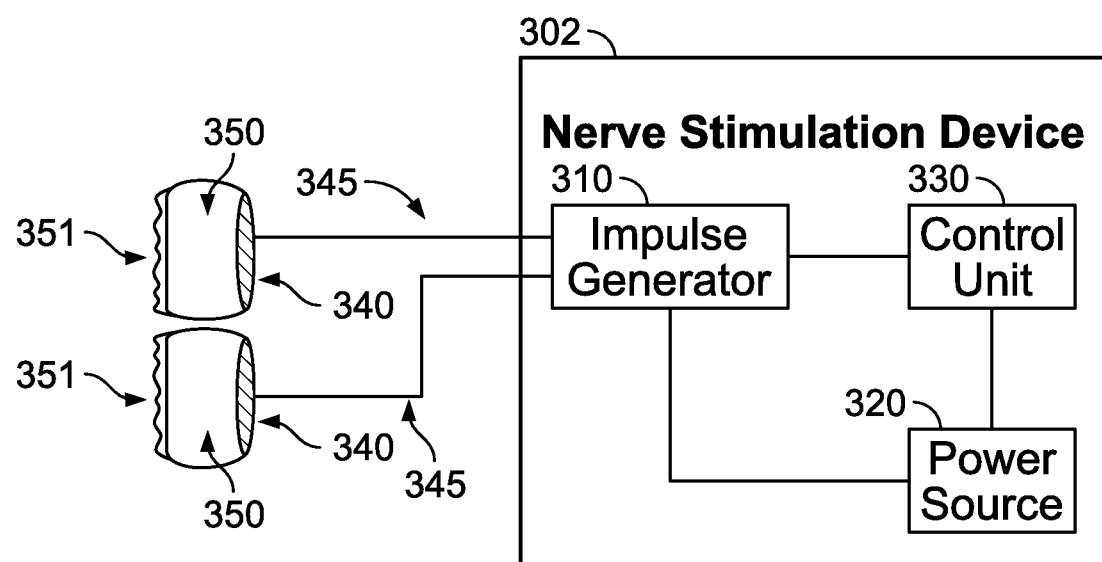
FIG. 1C shows a schematic view of embodiments of nerve modulating devices according to this disclosure, which supply controlled pulses of electrical current to surface electrodes.

Some devices that are used to stimulate a vagus nerve are now described. An embodiment is shown in FIG. 1C, which is a schematic diagram of an electrode-based nerve stimulating and/or modulating device 302 for delivering impulses of energy to nerves for the treatment of medical conditions. As shown, device 302 may include an impulse generator 310; a power source 320 coupled to the impulse generator 310; a control unit 330 in communication with the impulse generator 310 and coupled to the power source 320; and electrodes 340 coupled via wires 345 to impulse generator 310. In some embodiments, the same impulse generator 310, power source 320, and control unit 330 may be used for either a magnetic stimulator or the electrode-based stimulator 302, allowing the user to change parameter settings depending on whether magnetic coils or the electrodes 340 are attached.

Although a pair of electrodes 340 is shown in FIG. 1C, in practice the electrodes may also comprise three or more distinct electrode elements, each of which is connected in series or in parallel to the impulse generator 310. Thus, the electrodes 340 that are shown in FIG. 1C represent some, most, many, or all electrodes of the device collectively.

The item labeled in FIG. 1C as 350 is a volume, contiguous with an electrode 340, that is filled with electrically conducting medium. The conducting medium in which the electrode 340 is embedded need not completely surround or extend about an electrode. The volume 350 is electrically connected to the patient at a target skin surface in order to shape the current density passed through an electrode 340 that is needed to accomplish stimulation of the patient's nerve or tissue. The electrical connection to the patient's skin surface is through an interface 351. In some embodiments, the interface is made of an electrically insulating (dielectric) material, such as a thin sheet of Mylar. In that case, electrical coupling of the stimulator to the patient is capacitive. In some embodiments, the interface comprises electrically conducting material, such as the electrically conducting medium 350 itself, an electrically conducting or permeable membrane, or a metal piece. In that case, electrical coupling of the stimulator to the patient is ohmic. As shown, the interface may be deformable such that it is form fitting when applied to the surface of the body. Thus, the sinuousness or curvature shown at the outer surface of the interface 351 corresponds also to sinuousness or curvature on the surface of the body, against which the interface 351 is applied, so as to make the interface and body surface contiguous.

The control unit 330 controls the impulse generator 310 to generate a signal for each of the device's electrodes (or magnetic coils). The signals are selected to be suitable for amelioration of a particular medical condition, when the signals are applied non-invasively to a target nerve or tissue via the electrodes 340. It is noted that nerve stimulating/modulating device 302 may be referred to by its function as a pulse generator. Patent application publications US2005/0075701 and US2005/0075702, both to SHAFER, the disclosure of which is incorporated herein by reference for all purposes as if copied and pasted herein, contain descriptions of pulse generators that may be applicable to this disclosure. By way of example, a pulse generator is also commercially available, such as Agilent 33522A Function/Arbitrary Waveform Generator, Agilent Technologies, Inc., 5301 Stevens Creek Blvd Santa Clara CA 95051.

The control unit 330 may comprise a general purpose computer, comprising one or more CPU, computer memories for the storage of executable computer programs (including the system's operating system) and the storage and retrieval of data, disk storage devices, communication devices (such as serial and USB ports) for accepting external signals from a keyboard, computer mouse, and touchscreen, as well as any externally supplied physiological signals, analog-to-digital converters for digitizing externally supplied analog signals, communication devices for the transmission and receipt of data to and from external devices such as printers and modems that comprise part of the system, hardware for generating the display of information on monitors or display screens that comprise part of the system, and busses to interconnect the above-mentioned components. Thus, the user may operate the system by typing or otherwise providing instructions for the control unit 330 at a device such as a keyboard or touch-screen and view the results on a device such as the system's computer monitor or display screen, or direct the results to a printer, modem, and/or storage disk. Control of the system may be based upon feedback measured from externally supplied physiological or environmental signals. Alternatively, the control unit 330 may have a compact and simple structure, for example, wherein the user may operate the system using only an on/off switch and power control wheel or knob, or their touchscreen equivalent. In a section below, an embodiment is also described wherein the stimulator housing has a simple structure, but other components of the control unit 330 are distributed into other devices (see FIG. 5).

Parameters for the nerve or tissue stimulation include power level, frequency and train duration (or pulse number). The stimulation characteristics of each pulse, such as depth of penetration, strength and selectivity, depend on the rise time and peak electrical energy transferred to the electrodes, as well as the spatial distribution of the electric field that is produced by the electrodes. The rise time and peak energy are governed by the electrical characteristics of the stimulator and electrodes, as well as by the anatomy of the region of current flow within the patient. In some embodiments, pulse parameters are set in such a way as to account for the detailed anatomy surrounding the nerve that is being stimulated [Bartosz SAWICKI, Robert Szmurlo, Przemyslaw Plonecki, Jacek Starzynski, Stanislaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, 105 Press, 2008, the disclosure of which is incorporated herein by reference for all purposes as if copied and pasted herein]. Pulses may be monophasic, biphasic or polyphasic. In some embodiments, some devices include those that are fixed frequency, where each pulse in a train has the same interstimulus interval, and those that have modulated frequency, where the intervals between each pulse in a train can be varied.

FIG. 2A illustrates an example of an electrical voltage/current profile for a stimulating, blocking and/or modulating impulse applied to a portion or portions of selected nerves in accordance with an embodiment of this disclosure. For some embodiments, the voltage and current refer to those that are non-invasively produced within the patient by the electrodes (or magnetic coils). As shown, a suitable electrical voltage/current profile 400 for the blocking and/or modulating impulse 410 to the portion or portions of a nerve may be achieved using pulse generator 310. In some embodiments, the pulse generator 310 may be implemented using a power source 320 and a control unit 330 having, for instance, a processor, a clock, a memory, etc., to produce a pulse train 420 to the electrodes 340 that deliver the stimulating, blocking and/or modulating impulse 410 to the nerve. Nerve stimulating/modulating device 302 may be externally powered and/or recharged or may have its own power source 320. The parameters of the modulation signal 400, such as the frequency, amplitude, duty cycle, pulse width, pulse shape, etc., can be programmable, non-programmable, modifiable, locally or remotely updateable, or others. An external communication device may modify the pulse generator programming to improve treatment.

In addition, or as an alternative to some of the devices to implement the modulation unit for producing the electrical voltage/current profile of the stimulating, blocking and/or modulating impulse to the electrodes, the device disclosed in US Patent Application Publication No. US2005/0216062, the disclosure of which is incorporated herein by reference for all purposes as if copied and pasted herein, may be employed. That patent publication discloses a multifunctional electrical stimulation (ES) system adapted to yield output signals for effecting electromagnetic or other forms of electrical stimulation for a broad spectrum of different biological and biomedical applications, which produce an electric field pulse in order to non-invasively stimulate nerves. The system includes an ES signal stage having a selector coupled to a plurality of different signal generators, each producing a signal having a distinct shape, such as a sine wave, a square or a saw-tooth wave, or simple or complex pulse, the parameters of which are adjustable in regard to amplitude, duration, repetition rate and other variables. Examples of the signals that may be generated by such a system are described in a publication by LIBOFF [A. R. LIBOFF. Signal shapes in electromagnetic therapies: a primer. pp. 17-37 in: Bioelectromagnetic Medicine (Paul J. Rosch and Marko S. Markov, eds.). New York: Marcel Dekker (2004), the disclosure of which is incorporated herein by reference for all purposes as if copied and pasted herein]. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated, as well as the outputs of various sensors which sense prevailing conditions prevailing in this substance, whereby the user of the system can manually adjust the signal, or have it automatically adjusted by feedback, to provide an electrical stimulation signal of whatever type the user wishes, who can then observe the effect of this signal on a substance being treated.

The stimulating and/or modulating impulse signal 410 preferably has a frequency, an amplitude, a duty cycle, a pulse width, a pulse shape, etc. selected to influence the therapeutic result, namely, stimulating and/or modulating some or all of the transmission of the selected nerve. For example, the frequency may be about 1 Hz or greater, such as between about 15 Hz to 100 Hz, preferably between about 15-50 Hz and more preferably between about 15-35 Hz. In some embodiments, the frequency is 25 Hz. The modulation signal may have a pulse width selected to influence the therapeutic result, such as about 1 microseconds to about 1000 microseconds, preferably about 100-400 microseconds and more preferably about 200-400 microseconds. For example, the electric field induced or produced by the device within tissue in the vicinity of a nerve may be about 5 to 600 V/m, preferably less than 100 V/m, and even more preferably less than 30 V/m. The gradient of the electric field may be greater than 2 V/m/mm. More generally, the stimulation device produces an electric field in the vicinity of the nerve that is sufficient to cause the nerve to depolarize and reach a threshold for action potential propagation, which is approximately 8 V/m at 1000 Hz. The modulation signal may have a peak voltage amplitude selected to influence the therapeutic result, such as about 0.2 volts or greater, such as about 0.2 volts to about 40 volts, preferably between about 1-20 volts and more preferably between about 2-12 volts.

In some embodiments, an objective of some of the disclosed stimulators is to provide both nerve fiber selectivity and spatial selectivity. Spatial selectivity may be achieved in part through the design of the electrode (or magnetic coil) configuration, and nerve fiber selectivity may be achieved in part through the design of the stimulus waveform, but designs for the two types of selectivity are intertwined. This is because, for example, a waveform may selectively stimulate only one of two nerves whether they lie close to one another or not, obviating the need to focus the stimulating signal onto only one of the nerves [GRILL W and Mortimer J T. Stimulus waveforms for selective neural stimulation. IEEE Eng. Med. Biol. 14 (1995): 375-385, the disclosure of which is incorporated herein by reference for all purposes as if copied and pasted herein]. These methods complement others that are used to achieve selective nerve stimulation, such as the use of local anesthetic, application of pressure, inducement of ischemia, cooling, use of ultrasound, graded increases in stimulus intensity, exploiting the absolute refractory period of axons, and the application of stimulus blocks [John E. SWETT and Charles M. Bourassa. Electrical stimulation of peripheral nerve. In: Electrical Stimulation Research Techniques, Michael M. Patterson and Raymond P. Kesner, eds. Academic Press. (New York, 1981) pp. 243-

295, the disclosure of which is incorporated herein by reference for all purposes as if copied and pasted herein].

For some devices, to date, some of the selection of stimulation waveform parameters for nerve stimulation has been highly empirical, in which the parameters are varied about some initially successful set of parameters, in an effort to find an improved set of parameters for each patient. A more efficient approach to selecting stimulation parameters might be to select a stimulation waveform that mimics electrical activity in the anatomical regions that one is attempting stimulate indirectly, in an effort to entrain the naturally occurring electrical waveform, as suggested in patent number U.S. Pat. No. 6,234,953, entitled Electrotherapy device using low frequency magnetic pulses, to THOMAS et al; the disclosure of which is incorporated herein by reference for all purposes as if copied and pasted herein, and application number US20090299435, entitled Systems and methods for enhancing or affecting neural stimulation efficiency and/or efficacy, to GLINER et al, the disclosure of which is incorporated herein by reference for all purposes as if copied and pasted herein. One may also vary stimulation parameters iteratively, in search of an optimal setting [U.S. Pat. No. 7,869,885, entitled Threshold optimization for tissue stimulation therapy, to BEGNAUD et al, the disclosure of which is incorporated herein by reference for all purposes as if copied and pasted herein]. However, some stimulation waveforms, such as those described herein, are discovered by trial and error, and then deliberately improved upon.

Invasive nerve stimulation typically uses square wave pulse signals. However, Applicant found that square waveforms are not ideal for non-invasive stimulation, as they produce excessive pain, but still can be used. Prepulses and similar waveform modifications have been suggested as methods to improve selectivity of nerve stimulation waveforms, but Applicant also did not find them ideal, although they still can be used [Aleksandra VUCKOVIC, Marco Tosato and Johannes J Struijk. A comparative study of three techniques for diameter selective fiber activation in the vagal nerve: anodal block, depolarizing prepulses and slowly rising pulses. J. Neural Eng. 5 (2008): 275-286, the disclosure of which is incorporated herein by reference for all purposes as if copied and pasted herein; Aleksandra VUCKOVIC, Nico J. M. Rijkhoff, and Johannes J. Struijk. Different Pulse Shapes to Obtain Small Fiber Selective Activation by Anodal Blocking—A Simulation Study. IEEE Transactions on Biomedical Engineering 51(5,2004):698-706, the disclosure of which is incorporated herein by reference for all purposes as if copied and pasted herein; Kristian HENNINGS. Selective Electrical Stimulation of Peripheral Nerve Fibers: Accommodation Based Methods. Ph.D. Thesis, Center for Sensory-Motor Interaction, Aalborg University, Aalborg, Denmark, 2004, the disclosure of which is incorporated herein by reference for all purposes as if copied and pasted herein].

The Applicant also found that stimulation waveforms including of bursts of square pulses are not ideal for non-invasive stimulation, but can still be used [M. I. JOHNSON, C. H. Ashton, D. R. Bousfield and J. W. Thompson. Analgesic effects of different pulse patterns of transcutaneous electrical nerve stimulation on cold-induced pain in normal subjects. Journal of Psychosomatic Research 35 (2/3, 1991): 313-321, the disclosure of which is incorporated herein by reference for all purposes as if copied and pasted herein; U.S. Pat. No. 7,734,340, entitled Stimulation design for neuromodulation, to De Ridder, the disclosure of which is incorporated herein by reference for all purposes as if copied and pasted herein]. However, bursts of sinusoidal pulses are a desired stimulation waveform, as shown in FIGS. 2B and 2C. As seen there, individual sinusoidal pulses have a period of T, and a burst consists of N such pulses. This is followed by a period with no signal (the inter-burst period). The pattern of a burst followed by silent inter-burst period repeats itself with a period of T. For example, the sinusoidal period T may be between about 50-1000 microseconds (substantially equivalent to about 1-20 KHz), preferably between about 100-400 microseconds (substantially equivalent to about 2.5-10 KHz), more preferably about 133-400 microseconds (substantially equivalent to about 2.5-7.5 KHZ) and even more preferably about 200 microseconds (substantially equivalent to about 5 KHz); the number of pulses per burst may be N=1-20, preferably about 2-10 and more preferably about 5; and the whole pattern of burst followed by silent inter-burst period may have a period T comparable to about 10-100 Hz, preferably about 15-50 Hz, more preferably about 25-35 Hz and even more preferably about 25 Hz (a much smaller value of T is shown in FIG. 2E to make the bursts discernable). When these exemplary values are used for T and τ, the waveform contains significant Fourier components at higher frequencies (1/200 microseconds=5000/sec), as compared with those contained in transcutaneous nerve stimulation waveforms, as currently practiced.

The above waveform is essentially a 1-20 KHz signal that includes bursts of pulses with each burst having a frequency of about 10-100 Hz and each pulse having a frequency of about 1-20 KHz. Another way of thinking about the waveform is that it is a 1-20 KHz waveform that repeats itself at a frequency of about 10-100 Hz. The Applicant is unaware of such a waveform having been used with vagus nerve stimulation, but a similar waveform has been used to stimulate muscle as a means of increasing muscle strength in elite athletes. However, for the muscle strengthening application, the currents used (200 mA) may be very painful and two orders of magnitude larger than what are disclosed herein. Furthermore, the signal used for muscle strengthening may be other than sinusoidal (e.g., triangular), and the parameters T, N, and T may also be dissimilar from the values exemplified above [A. DELITTO, M. Brown, M. J. Strube, S. J. Rose, and R. C. Lehman. Electrical stimulation of the quadriceps femoris in an elite weight lifter: a single subject experiment. Int J Sports Med 10(1989):187-191, the disclosure of which is incorporated herein by reference for all purposes as if copied and pasted herein; Alex R WARD, Nataliya Shkuratova. Russian Electrical Stimulation: The Early Experiments. Physical Therapy 82 (10,2002): 1019-1030, the disclosure of which is incorporated herein by reference for all purposes as if copied and pasted herein; Yocheved LAUFER and Michel Elboim. Effect of Burst Frequency and Duration of Kilohertz-Frequency Alternating Currents and of Low-Frequency Pulsed Currents on Strength of Contraction, Muscle Fatigue, and Perceived Discomfort. Physical Therapy 88 (10,2008):1167-1176, the disclosure of which is incorporated herein by reference for all purposes as if copied and pasted herein; Alex R WARD. Electrical Stimulation Using Kilohertz-Frequency Alternating Current. Physical Therapy 89 (2,2009):181-190, the disclosure of which is incorporated herein by reference for all purposes as if copied and pasted herein; J. PETROFSKY, M. Laymon, M. Prowse, S. Gunda, and J. Batt. The transfer of current through skin and muscle during electrical stimulation with sine, square, Russian and interferential waveforms. Journal of Medical Engineering and Technology 33 (2,2009): 170-181, the disclosure of which is incorporated herein by reference for all purposes as if copied and pasted herein; U.S. Pat. No. 4,177,819, entitled Muscle stimulating apparatus, to KOFSKY et al, the disclosure of which is incorporated herein by reference for all purposes as if copied and pasted herein]. Burst stimulation has also been disclosed in connection with implantable pulse generators, but wherein the bursting is characteristic of the neuronal firing pattern itself [U.S. Pat. No. 7,734,340 to DE RIDDER, entitled Stimulation design for neuromodulation, the disclosure of which is incorporated herein by reference for all purposes as if copied and pasted herein; US Patent Application Publication US20110184486 to DE RIDDER, entitled Combination of tonic and burst stimulations to treat neurological disorders, the disclosure of which is incorporated herein by reference for all purposes as if copied and pasted herein]. By way of example, the electric field shown in FIGS. 2B and 2C may have an $E_{max}$ value of 17 V/m, which is sufficient to stimulate the nerve but is significantly lower than the threshold needed to stimulate surrounding muscle.

In some embodiments, the use of feedback to generate the modulation signal 400 may result in a signal that is not periodic, particularly if the feedback is produced from sensors that measure naturally occurring, time-varying aperiodic physiological signals from the patient. In fact, the absence of significant fluctuation in naturally occurring physiological signals from a patient is ordinarily considered to be an indication that the patient is in ill health. This is because a pathological control system that regulates the patient's physiological variables may have become trapped around only one of two or more possible steady states and is therefore unable to respond normally to external and internal stresses. Accordingly, even if feedback is not used to generate the modulation signal 400, it may be useful to artificially modulate the signal in an aperiodic fashion, in such a way as to simulate fluctuations that would occur naturally in a healthy individual. Thus, the noisy modulation of the stimulation signal may cause a pathological physiological control system to be reset or undergo a non-linear phase transition, through a mechanism known as stochastic resonance [B. SUKI, A. Alencar, M. K. Sujeer, K. R. Lutchen, J. J. Collins, J. S. Andrade, E. P. Ingenito, S. Zapperi, H. E. Stanley, Life-support system benefits from noise, Nature 393 (1998) 127-128, the disclosure of which is incorporated herein by reference for all purposes as if copied and pasted herein; W Alan C MUTCH, M Ruth Graham, Linda G Girling and John F Brewster. Fractal ventilation enhances respiratory sinus arrhythmia. Respiratory Research 2005, 6:41, pp. 1-9, the disclosure of which is incorporated herein by reference for all purposes as if copied and pasted herein].

In some embodiments, the modulation signal 400, with or without feedback, will stimulate the selected nerve fibers in such a way that one or more of the stimulation parameters (e.g., power, frequency, and others mentioned herein) are varied by sampling a statistical distribution having a mean corresponding to a selected, or to a most recent running-averaged value of the parameter, and then setting the value of the parameter to the randomly sampled value. The sampled statistical distributions will comprise Gaussian and 1/f, obtained from recorded naturally occurring random time series or by calculated formula. Parameter values will be so changed periodically, or at time intervals that are themselves selected randomly by sampling another statistical distribution, having a selected mean and coefficient of variation, where the sampled distributions comprise Gaussian and exponential, obtained from recorded naturally occurring random time series or by calculated formula.

In some embodiments, some devices, as disclosed herein, are provided in a "pacemaker" type form, in which electrical impulses 410 are generated to a selected region of the nerve by a stimulator device on an intermittent basis, to create in the patient a lower reactivity of the nerve.

Embodiments of the Electrode-Based Stimulators

The electrodes of the some of the devices, as disclosed herein, are applied to the surface of the neck, or to some other surface of the body, and are used to deliver electrical energy non-invasively to a nerve. Embodiments may differ with regard to the number of electrodes that are used, the distance between electrodes, and whether disk or ring electrodes are used. In some embodiments, one selects the electrode configuration for individual patients, in such a way as to optimally focus electric fields and currents onto the selected nerve, without generating excessive currents on the surface of the skin. This tradeoff between focality and surface currents is described by DATTA et al. [Abhishek DATTA, Maged Elwassif, Fortunato Battaglia and Marom Bikson. Transcranial current stimulation focality using disc and ring electrode configurations: FEM analysis. J. Neural Eng. 5 (2008): 163-174, the disclosure of which is incorporated herein by reference for all purposes as if copied and pasted herein]. Although DATTA et al. are addressing the selection of electrode configuration specifically for transcranial current stimulation, some of the principles that they describe are applicable to peripheral nerves as well [RATTAY F. Analysis of models for extracellular fiber stimulation. IEEE Trans. Biomed. Eng. 36 (1989): 676-682, the disclosure of which is incorporated herein by reference for all purposes as if copied and pasted herein].

Figure 3A:
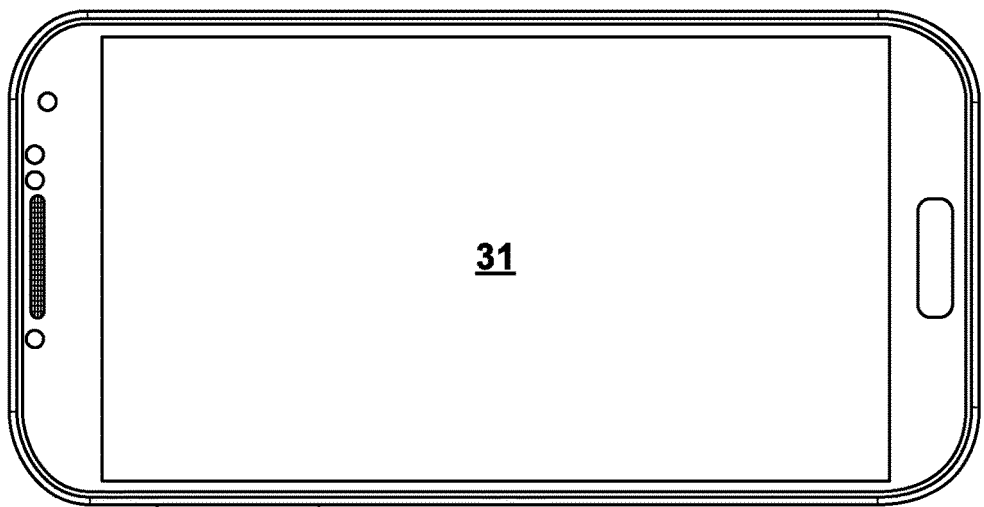
FIG. 3A is a front view of an embodiment of a dual-electrode stimulator according to this disclosure, showing that the stimulator device comprises a smartphone.
Figure 3B:
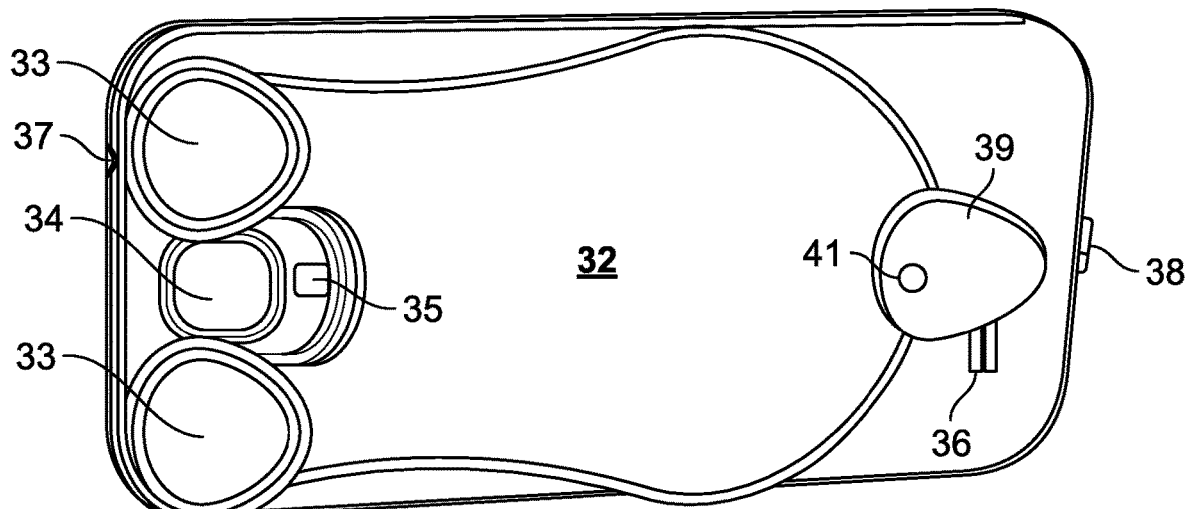
FIG. 3B is a back view of an embodiment of the dual-electrode stimulator shown in FIG. 3A according to this disclosure.

An embodiment of an electrode-based stimulator is shown in FIG. 3. As shown, the stimulator comprises a smartphone (31) with its back cover removed and and joined to a housing (32) that comprises a pair of electrode surfaces (33) along with circuitry to control and power the electrodes and interconnect with the smartphone. The electrode surface (33) in FIG. 3 corresponds to item 351 in FIG. 1. FIG. 3A shows the side of the smartphone (31) with a touch-screen. FIG. 3B shows the housing of the stimulator (32) joined to the back of the smartphone. Portions of the housing lie flush with the back of the smartphone, with windows to accommodate smartphone components that are found on the original back of the smartphone. Such components may also be used with the stimulator, e.g., the smartphone's rear camera (34), flash (35) and speaker (36). Other original components of the smartphone may also be used, such as the audio headset jack socket (37) and multi-purpose jack (38). Note that the original components of the smartphone shown in FIG. 3 correspond to a Samsung Galaxy smartphone, and their locations may be different for embodiments that use different smartphone models by different smartphone manufacturers. Note that tablets can be used as well.

Figure 3C:
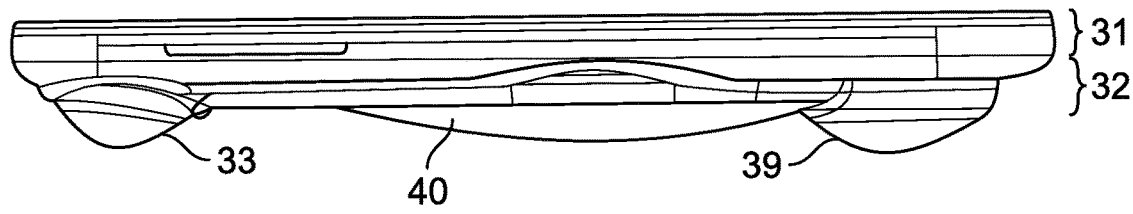
FIG. 3C is a side view of an embodiment of the dual-electrode stimulator shown in FIG. 3A according to this disclosure.

FIG. 3C shows that several portions of the housing (32) protrude towards the back. The two electrode surfaces (33) protrude so that they may be applied to the skin of the patient. The stimulator may be held in place by straps or frames or collars, or the stimulator may be held against the patient's body by hand. In some embodiments, the neurostimulator may comprise a single such electrode surface or more than two electrode surfaces.

A dome (39) also protrudes from the housing, so as to allow the device to lie more or less flat on a table when supported also by the electrode surfaces. The dome also accommodates a relatively tall component that may lie underneath it, such as a battery. Alternatively, the stimuluation device may be powered by the smartphone's battery. If the battery under the dome is rechargeable, the dome may contain a socket (41) through which the battery is recharged using a jack that is inserted into it, which is, for example, attached to a power cable from a base station (described below). The belly (40) of the housing protrudes to a lesser extent than the electrodes and dome. The belly accommodates a printed circuit board that contains electronic components within the housing (not shown), as described below.

Generally, the stimulator is designed to situate the electrodes of the stimulator (340 in FIG. 1) remotely from the surface of the skin within a chamber, with conducting material (350 in FIG. 1) placed in a chamber between the electrode and the exterior component of the stimulator head that contacts the skin (351 in FIG. 1). One of the features of this design is that the stimulator, along with a correspondingly suitable stimulation waveform (see FIG. 2), shapes the electric field, producing a selective physiological response by stimulating that nerve, but avoiding substantial stimulation of nerves and tissue other than the target nerve, particularly avoiding the stimulation of nerves that produce pain. The shaping of the electric field is described in terms of the corresponding field equations in co-pending, commonly assigned application US20110230938 (application Ser. No. 13/075,746), entitled Devices and methods for non-invasive electrical stimulation and their use for vagal nerve stimulation on the neck of a patient, to SIMON et al., the disclosure of which is incorporated herein by reference for all purposes as if copied and pasted herein.

In some embodiments, the disc interface 351 actually functions as the electrode and the screw 340 is simply the output connection to the signal generator electronics. In this embodiment, electrically conductive fluid (e.g., liquid, gas) or gel is positioned between the signal generator and the interface or electrode 351. In this embodiment, the conductive fluid filters out or eliminates high frequency components from the signal to smooth out the signal before it reaches the electrode(s) 351. When the signal is generated, power switching and electrical noise typically add unwanted high frequency spikes back into the signal. In addition, the pulsing of the sinusoidal bursts may induce high frequency components in the signal. By filtering the signal just before it reaches the electrodes 351 with the conductive fluid, a smoother, cleaner signal is applied to the patient, thereby reducing the pain and discomfort felt by the patient and allowing a higher amplitude to be applied to the patient. This allows a sufficiently strong signal to be applied to reach a deeper nerve, such as the vagus nerve, without causing too much pain and discomfort to the patient at the surface of their skin.

In some embodiments, a low-pass filter may be used additional to or instead of the electrically conductive fluid to filter out the undesirable high frequency components of the signal. The low-pass filter may comprise a digital or active filter or simply two series resistors and a parallel capacitor placed between the signal generator and the electrode/interface.

Figure 4A:
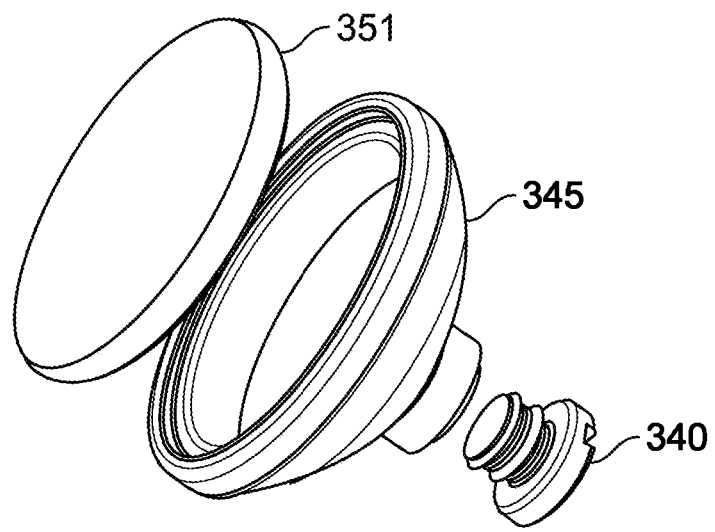
FIG. 4A illustrates an exploded view of an embodiment of an electrode assembly according to this disclosure and FIG. 4B illustrates an assembled view of an embodiment of the electrode assembly shown in FIG. 4A according to this disclosure.
Figure 4B:
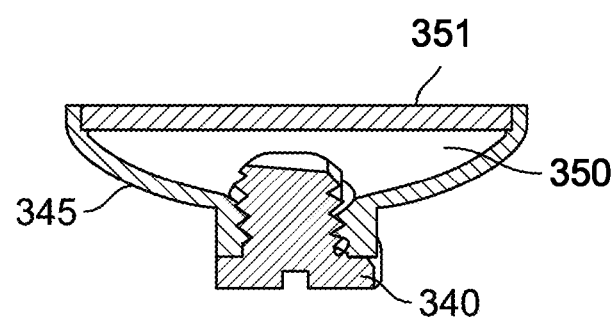

The electrode surface (33) was shown in FIG. 3C as being roughly hemispherical so that as the electrode surface is pressed into the patient's skin, the surface area of skin contact would increase. However, in other designs of the electrode surface (corresponding to 351 in FIG. 1), the electrode surface may be flat. Such an alternate design is shown in FIG. 4. As shown in FIG. 4A, the electrode surface (351) comprises a metal (e.g., stainless steel) disc that fits into the top of a non-conducting (e.g., plastic) chamber (345). At the other end of the chamber, a threaded port accepts a metal screw that serves as the actual electrode (340). A wire will be attached to the screw, connecting it to impulse generating circuitry. The assembled components are shown in FIG. 4B, which also shows the location of an electrically conducting material (350) within the chamber, such as an electrolyte solution or gel, that allows the electrode (340) to conduct current to the external electrode surface (351).

Electronics and Software of the Stimulator

In some embodiments, the signal waveform (FIG. 2) that is to be applied to electrodes of the stimulator is initially generated in a component of the impulse generator (310 in FIG. 1) that is exterior to, and remote from, the mobile phone housing. The mobile phone preferably includes a software application that can be downloaded (e.g., mobile app store, USB cable, memory stick, Bluetooth connection) into the phone to receive, from the external control component, a wirelessly transmitted waveform, or to receive a waveform that is transmitted by cable, e.g., via the multipurpose jack 38 in FIG. 3. If the waveforms are transmitted in compressed form, they are preferably compressed in a lossless manner, e.g., making use of FLAC (Free Lossless Audio Codec). Alternatively, the downloaded software application may itself be coded to generate a particular waveform that is to be applied to the electrodes (340 in FIG. 1C) and subsequently conveyed to the external interface of the electrode assembly (351 in FIG. 1C and 33 in FIG. 3). In some embodiments, the software application is not downloaded from outside the device, but is instead available internally, for example, within read-only-memory that is present within the housing of the stimulator (32 in FIGS. 3B and 3C).

In some embodiments, the waveform is first conveyed by the software application to contacts within the phone's speaker output or the earphone jack socket (37 in FIG. 3B), as though the waveform signal were a generic audio waveform. That pseudo-audio waveform will generally be a stereo waveform, representing signals that are to be applied to the "left" and "right" electrodes. The waveform will then be conveyed to the housing of the stimulator (32 in FIGS. 3B and 3C), as follows. The housing of the stimulator may have an attached dangling audio jack that is plugged into the speaker output or the earphone jack socket 37 whenever electrical stimulation is to be performed, or the electrical connection between the contacts of the speaker output or the earphone jack socket and the housing of the stimulator may be hard-wired. In either case, electrical circuits on a printed circuit board located under the belly of the housing (40 in FIG. 3C) of the stimulator may then shape, filter, and/or amplify the pseudo-audio signal that is received via the speaker output or earphone jack socket. A power amplifier within the housing of the stimulator may then drive the signal onto the electrodes, in a fashion that is analogous to the use of an audio power amplifier to drive loudspeakers. Alternatively, the signal processing and amplification may be implemented in a separate device that can be plugged into sockets on the phone and/or housing of the stimulator (32 in FIGS. 3B and 3C), to couple the software application and the electrodes.

In addition to passing the stimulation waveform from the smartphone to the stimulator housing as described herein, the smartphone may also pass control signals to the stimulator housing. Thus, the stimulation waveform may generally be regarded as a type of analog, pseudo-audio signal, but if the signal contains a signature series of pulses signifying that a digital control signal is about to be sent, logic circuitry in the stimulator housing may then be set to decode the series of digital pulses that follows the signature series of pulses, analogous to the operation of a modem.

Many of the steps that direct the waveform to the electrodes, including steps that may be controlled by the user via the touchscreen (31 in FIG. 3A), are implemented in the above-mentioned software application. By way of example, the software application may be written for a phone that uses the Android operating system. Such applications are typically developed in the Java programming language using the Android Software Development Kit (SDK), in an integrated development environment (IDE), such as Eclipse [Mike WOLFSON. Android Developer Tools Essentials. Sebastopol, CA: O'Reilly Media Inc., 2013; Ronan SCHWARZ, Phil Duston, James Steele, and Nelson To. The Android Developer's Cookbook. Building Applications with the Android SDK, Second Edition. Upper Saddle River, NJ: Addison-Wesley, 2013, the disclosure of which is incorporated herein by reference for all purposes as if copied and pasted herein; Shane CONDER and Lauren Darcey. Android Wireless Application Development, Second Edition. Upper Saddle River, NJ: Addison-Wesley, 2011; Jerome F. DIMARZIO. Android—A Programmer's Guide. New York: McGraw-Hill. 2008. pp. 1-319, the disclosure of which is incorporated herein by reference for all purposes as if copied and pasted herein]. Application programming interfaces (APIs) that are particularly relevant to the audio features of such an Android software application (e.g., MediaPlayer APIs) are described by: Android Open Source Project of the Open Handset Alliance. Media Playback, at web domain developer.android.com with subdomain/guide/topics/media/, Jul. 18, 2014, the disclosure of which is incorporated herein by reference for all purposes as if copied and pasted herein. Those APIs can be relevant to a use of the smartphone camera capabilities, as described below. Additional components of the software application are available from device manufacturers [Samsung Mobile SDK, at web domain developer.samsung.com with subdomain/samsung-mobile-sdk, Jul. 18, 2014, the disclosure of which is incorporated herein by reference for all purposes as if copied and pasted herein].

In some embodiments, the stimulator and/or smartphone will include a user control, such as a switch or button, that disables/enables the stimulator. Preferably, the switch will automatically disable some, many, most, or all smartphone functions when the stimulator is enabled (and vice versa). This ensures that the medical device functionality of the smartphone is completely segregated from the rest of the phone's functionality. In some embodiments, the switch will be password-controlled such that only the patient/owner of the stimulator/phone will be able to enable the stimulator functionality. In one such embodiment, the switch will be controlled by a biometric scan (e.g., fingerprint, optical scan or the like) such that the stimulator functionality can only be used by the patient. This ensures that only the patient will be able to use the prescribed therapy in the event the phone is lost or stolen.

The stimulator and/or phone can also include software that allows the patient to order more therapy doses over the internet (discussed in more detail below in connection with the docking station). The purchase of such therapy doses will require physician authorization through a prescription or the like. To that end, the software can include an authorization code for entry in order for the patient to download authorization for more therapies. In some embodiments, without such authorization, the stimulator will be disabled and will not deliver therapy.

Although the device shown in FIG. 3 is an adapted commercially available smartphone, it is understood that in some embodiments, the housing of the stimulator may also be joined to and/or powered by a wireless device that is not a phone (e.g., Wi-Fi enabled device, wearable, tablet). Alternatively, the stimulator may be coupled to a phone or other Wi-Fi enabled device through a wireless connection for exchanging data at short distances, such as Bluetooth or the like. In this embodiment, the stimulator housing is not attached to the smartphone and, therefore, may comprise a variety of other shapes and sizes that are convenient for the patient to carry in his or her purse, wallet or pocket.

In some embodiments, the stimulator housing may be designed as part of a protective or decorative case for the phone that can be attached to the phone, similar to standard phone cases. In one such embodiment, the stimulator/case may also include additional battery life for the phone and may include an electrical connection to the phone's battery to recharge the battery (e.g., part of a Mophie® or the like). This electrical connection may also be used to couple the smartphone to the stimulator.

Embodiments with Distributed Controllers

In some embodiments, significant portions of the control of the vagus nerve stimulation reside in controller components that are physically separate from the housing of the stimulator. In these embodiment, separate components of the controller and stimulator housing generally communicate with one another wirelessly, although wired or waveguide communication is possible. Thus, the use of wireless technology avoids the inconvenience and distance limitations of interconnecting cables. Additional reasons in the present disclosure for physically separating many components of the controller from the stimulator housing are as follows.

First, the stimulator may be constructed with the minimum number of components needed to generate the stimulation pulses, with the remaining components placed in parts of the controller that reside outside the stimulator housing, resulting in a lighter and smaller stimulator housing. In fact, the stimulator housing may be made so small that it could be difficult to place, on the stimulator housing's exterior, switches and knobs that are large enough to be operated easily. Instead, for the present disclosure, the user may generally operate the device using the smartphone touchscreen.

Second, the controller (330 in FIG. 1C) may be given additional functions when free from the limitation of being situated within or near the stimulator housing. For example, one may add to the controller a data logging component that records when and how stimulation has been applied to the patient, for purposes of medical recordkeeping and billing. The complete electronic medical record database for the patient may be located far from the stimulator (e.g., somewhere on the internet), and the billing system for the stimulation services that are provided may also be elsewhere, so it would be useful to integrate the controller into that recordkeeping and billing system, using a communication system that includes access to the internet or telephone networks.

Third, communication from the databases to the controller would also be useful for purposes of metering electrical stimulation of the patient, when the stimulation is self-administered. For example, if the prescription for the patient only permits only a specified amount of stimulation energy to be delivered during a single session of vagus nerve stimulation, followed by a wait-time before allowing the next stimulation, the controller can query the database and then permit the stimulation only when the prescribed wait-time has passed. Similarly, the controller can query the billing system to assure that the patient's account is in order, and withhold the stimulation if there is a problem with the account.

Fourth, as a corollary of the previous considerations, the controller may be constructed to include a computer program separate from the stimulating device, in which the databases are accessed via cell phone or internet connections.

Fifth, in some applications, it may be desired that the stimulator housing and parts of the controller be physically separate. For example, when the patient is a child, one wants to make it impossible for the child to control or adjust the vagus nerve stimulation. The best arrangement in that case is for the stimulator housing to have no touchscreen elements, control switches or adjustment knobs that could be activated by the child. Alternatively, any touchscreen elements, switches and knobs on the stimulator can be disabled, and control of the stimulation then resides only in a remote controller with a child-proof operation, which would be maintained under the control of a parent or healthcare provider.

Sixth, in some applications, the particular control signal that is transmitted to the stimulator by the controller will depend on physiological and environmental signals that are themselves transmitted to and analyzed by the controller. In such applications, many of the physiological and environmental signals may already be transmitted wirelessly, in which case it is most convenient to design an external part of the controller as the hub of all such wireless activity, including any wireless signals that are sent to and from the stimulator housing.

With these considerations in mind, an embodiment of can include a base station that may send/receive data to/from the stimulator, and may send/receive data to/from databases and other components of the system, including those that are accessible via the internet (or another network such as local area, wide area, satellite, cellular). Typically, the base station will be a laptop computer attached to additional components needed for it to accomplish its function. Thus, prior to any particular stimulation session, the base station may load into the stimulator (FIG. 3) parameters of the session, including waveform parameters, or the actual waveform. See FIG. 2. In some embodiments, the base station is also used to limit the amount of stimulation energy that may be consumed by the patient during the session, by charging the stimulator's rechargable battery (see 41 in FIG. 3) with only a specified amount of releasable electrical energy, which is different than setting a parameter to restrict the duration of a stimulation session. Thus, the base station may comprise a power supply that may be connected to the stimulator's rechargable battery, and the base station meters the recharge. As a practical matter, the stimulator may therefore use two batteries, one for applying stimulation energy to the electrodes (the charge of which may be limited by the base station) and the other for performing other functions. Methods for evaluating a battery's charge or releasable energy can be as disclosed in U.S. Pat. No. 7,751,891, entitled Power supply monitoring for an implantable device, to ARMSTRONG et al, the disclosure of which is incorporated herein by reference for all purposes as if copied and pasted herein. Alternatively, some control components within the stimulator housing may monitor the amount of electrode stimulation energy that has been consumed during a stimulation session and stop the stimulation session when a limit has been reached, irrespective of the time when the limit has been reached.

Figure 5:
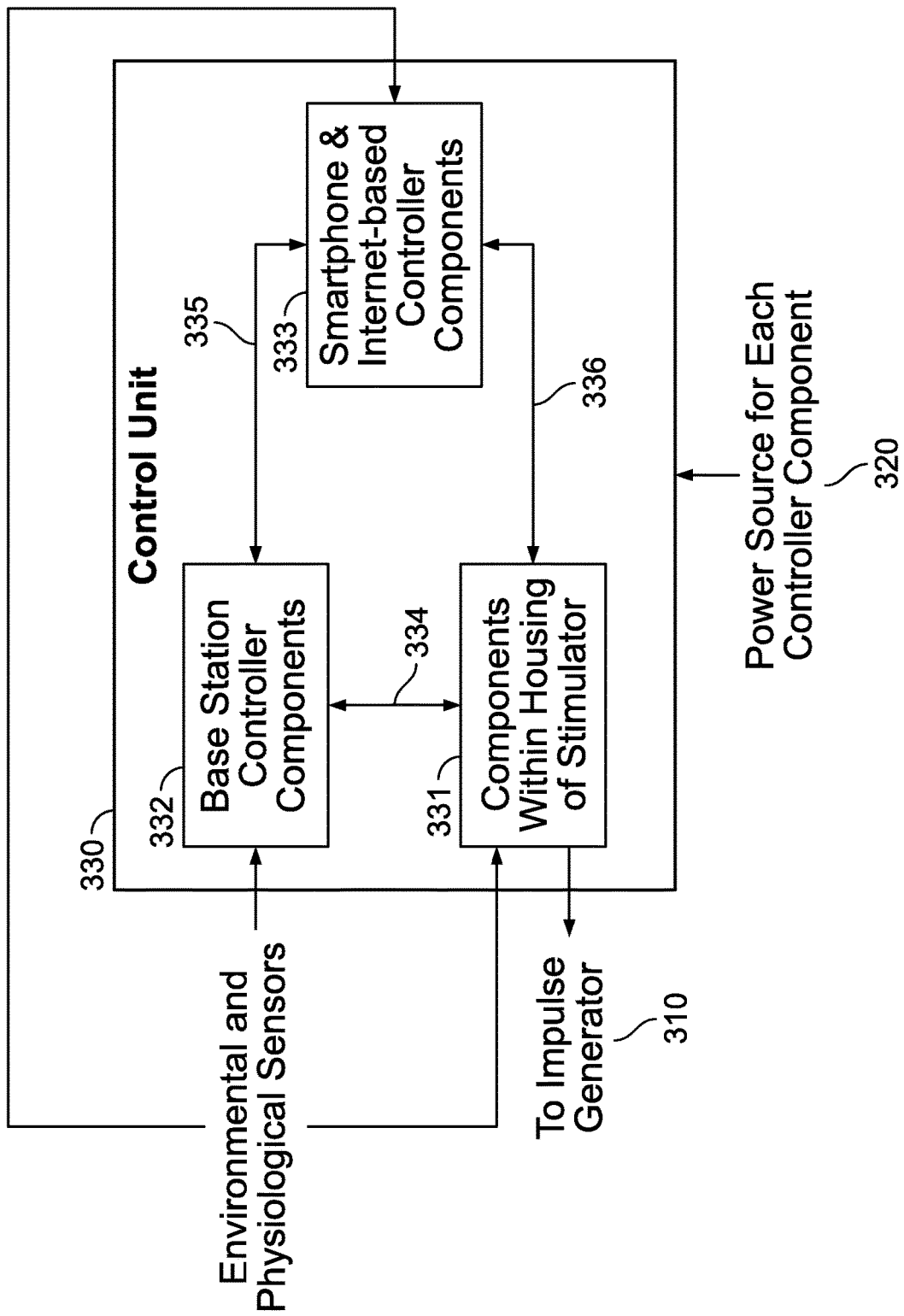
FIG. 5 shows an expanded diagram of an embodiment of the control unit shown in FIG. 1, separating components of the control unit into those within the housing of the stimulator, those within a base station, and those within smartphone and internet-based devices, also showing communication paths between such components according to this disclosure.

The communication connections between different components of the stimulator's controller are shown in FIG. 5, which is an expanded representation of the control unit 330 in FIG. 1C. Connection between the base station controller components 332 and components within the stimulator housing 331 is denoted in FIG. 5 as 334. Connection between the base station controller components 332 and internet-based (or network based) or smartphone components 333 is denoted as 335. Connection between the components within the stimulator housing 331 and internet-based or smartphone components 333 is denoted as 336. For example, control connections between the smartphone and stimulator housing via the audio jack socket would fall under this category, as would any wireless communication directly between the stimulator housing itself and a device situated on the internet. In principle, the connections 334, 335 and 336 in FIG. 5 may be either wired or wireless or waveguide-based. Different embodiments may lack one or more of the connections.

Although infrared or ultrasound wireless control might be used to communicate between components of the controller, they are not preferred because of line-of-sight limitations. Instead, in the present disclosure, the communication between devices preferably makes use of radio communication within unlicensed ISM frequency bands (260-470 MHz, 902-928 MHz, 2400-2.4835 GHz). Components of the radio frequency system in devices in 331, 332, and 333 typically comprise a system-on-chip transciever with an integrated microcontroller; a crystal; associated balun & matching circuitry, and an antenna [Dag GRINI. RF Basics, RF for Non-RF Engineers. Texas Instruments, Post Office Box 655303, Dallas, TX 75265, 2006, the disclosure of which is incorporated herein by reference for all purposes as if copied and pasted herein].

Transceivers based on 2.4 GHz offer high data rates (greater than 1 Mbps) and a smaller antenna than those operating at lower frequencies, which makes them suitable for with short-range devices. Furthermore, a 2.4 GHz wireless standard (e.g., Bluetooth, Wi-Fi, and Zig Bee) may be used as the protocol for transmission between devices. Although the ZigBee wireless standard operates at 2.4 GHz in most jurisdictions worldwide, it also operates in the ISM frequencies 868 MHz in Europe, and 915 MHz in the USA and Australia. Data transmission rates vary from 20 to 250 kilobits/second with that standard. Because many commercially available health-related sensors may operate using Zig Bee, its use may be recommended for applications in which the controller uses feedback and feedforward methods to adjust the patient's vagus nerve stimulation based on the sensors' values, as described below in connection with FIG. 11 [ZigBee Wireless Sensor Applications for Health, Wellness and Fitness. ZigBee Alliance 2400 Camino Ramon Suite 375 San Ramon, CA 94583].

A 2.4 GHz radio has higher power consumption than radios operating at lower frequencies, due to reduced circuit efficiencies. Furthermore, the 2.4 GHz spectrum is crowded and subject to significant interference from microwave ovens, cordless phones, 802.11b/g wireless local area networks, Bluetooth devices, etc. Sub-GHz radios enable lower power consumption and can operate for years on a single battery. These factors, combined with lower system cost, make sub-GHz transceivers ideal for low data rate applications that need maximum range and multi-year operating life.

The antenna length needed for operating at different frequencies is 17.3 cm at 433 MHz, 8.2 cm at 915 MHz, and 3 cm at 2.4 GHz. Therefore, unless the antenna is included in a neck collar that supports the device shown in FIG. 3, the antenna length may be a disadvantage for 433 MHz transmission. The 2.4 GHz band has the advantage of enabling one device to serve in all major markets worldwide since the 2.4 GHz band is a global spectrum standard. However, 433 MHz is a viable alternative to 2.4 GHz for most of the world, and designs based on 868 and 915 MHz radios can serve the US and European markets with a single product.

Range is determined by the sensitivity of the transceiver and its output power. A primary factor affecting radio sensitivity is the data rate. Higher data rates reduce sensitivity, leading to a need for higher output power to achieve sufficient range. For many applications that require only a low data rate, the preferred rate is 40 Kbps where the transceiver can still use a standard off-the-shelf 20 parts per million crystal.

A signal waveform that might be transmitted wirelessly to the stimulator housing was shown in FIGS. 2B and 2C. As seen there, individual sinusoidal pulses have a period of tau, and a burst consists of N such pulses. This is followed by a period with no signal (the inter-burst period). The pattern of a burst followed by silent inter-burst period repeats itself with a period of T. For example, the sinusoidal period tau may be 200 microseconds; the number of pulses per burst may be N=5; and the whole pattern of burst followed by silent inter-burst period may have a period of T=40000 microseconds, which is comparable to 25 Hz stimulation (a much smaller value of T is shown in FIG. 2C to make the bursts discernable). When these exemplary values are used for T and tau, the waveform contains significant Fourier components at higher frequencies (1/200 microseconds=5000/sec). Such a signal may be easily transmitted using 40 Kbps radio transmission. Compression of the signal is also possible, by transmitting only the signal parameters tau, N, T, Emax, etc., but in that case the stimulator housing's control electronics would then have to construct the waveform from the transmitted parameters, which would add to the complexity of components of the stimulator housing.

However, because it is contemplated that sensors attached to the stimulator housing may also be transmitting information, the data transfer requirements may be substantially greater than what is required only to transmit the signal shown in FIG. 2. Therefore, the present disclosure may make use of any frequency band, not limited to the ISM frequency bands, as well as techniques known in the art to suppress or avoid noise and interferences in radio transmission, such as frequency hopping and direct sequence spread spectrum.

Applications of Stimulators to the Neck of the Patient

Selected nerve fibers are stimulated in different embodiments of methods that make use of the disclosed electrical stimulation devices, including stimulation of the vagus nerve at a location in the patient's neck. At that location, the vagus nerve is situated within the carotid sheath, near the carotid artery and the interior jugular vein. The carotid sheath is located at the lateral boundary of the retropharyngeal space on each side of the neck and deep to the sternocleidomastoid muscle. The left vagus nerve is sometimes selected for stimulation because stimulation of the right vagus nerve may produce undesired effects on the heart, but depending on the application, the right vagus nerve or both right and left vagus nerves may be stimulated instead.

The three major structures within the carotid sheath are the common carotid artery, the internal jugular vein and the vagus nerve. The carotid artery lies medial to the internal jugular vein, and the vagus nerve is situated posteriorly between the two vessels. Typically, the location of the carotid sheath or interior jugular vein in a patient (and therefore the location of the vagus nerve) will be ascertained in any manner known in the art, e.g., by feel or ultrasound imaging. Proceeding from the skin of the neck above the sternocleidomastoid muscle to the vagus nerve, a line may pass successively through the sternocleidomastoid muscle, the carotid sheath and the internal jugular vein, unless the position on the skin is immediately to either side of the external jugular vein. In the latter case, the line may pass successively through only the sternocleidomastoid muscle and the carotid sheath before encountering the vagus nerve, missing the interior jugular vein. Accordingly, a point on the neck adjacent to the external jugular vein might be preferred for non-invasive stimulation of the vagus nerve. The magnetic stimulator coil may be centered on such a point, at the level of about the fifth to sixth cervical vertebra.

Figure 6:
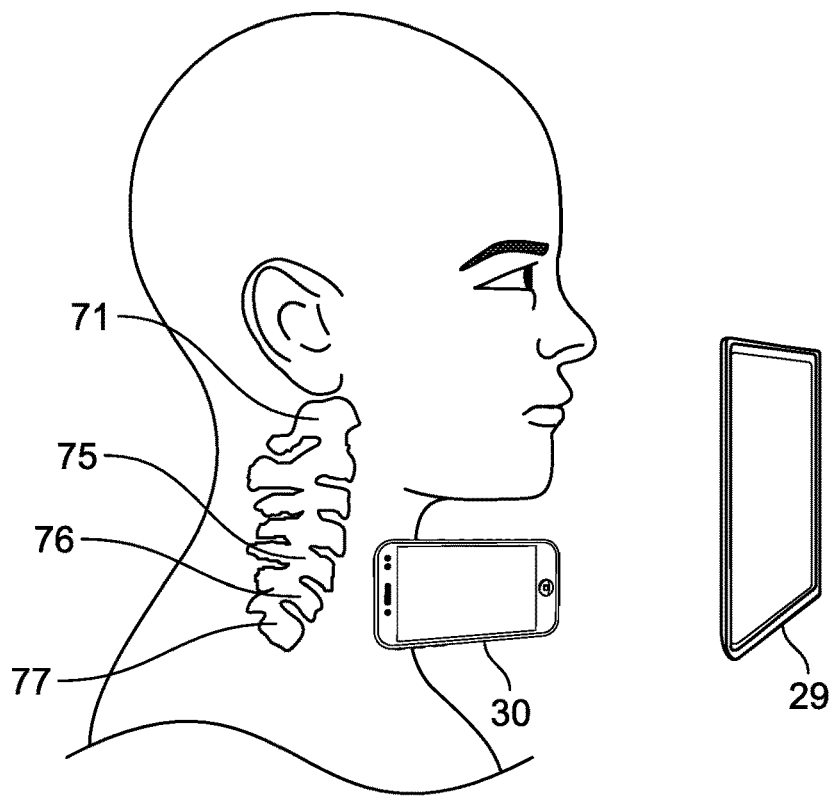
FIG. 6 illustrates an embodiment of an approximate position of a stimulator according to this disclosure, when used to stimulate a right vagus nerve in a neck of an adult patient.

FIG. 6 illustrates use of the device 30 shown in FIG. 3 (30 in FIG. 8=31+32 in FIG. 3) to stimulate the vagus nerve at that location in the neck, in which the stimulator device 30 is shown to be applied to the target location on the patient's neck as described herein. For reference, FIG. 6 shows the locations of the following vertebrae: first cervical vertebra 71, the fifth cervical vertebra 75, the sixth cervical vertebra 76, and the seventh cervical vertebra 77. Because the smartphone is applied to the patient's neck, the patient will generally need a mirror 29 to view and touch the phone's touchscreen. Therefore, the images displayed on the phone's screen may be reversed when the device is used as shown in FIG. 6. Alternatively, the images displayed on the phone's screen may be transmitted wirelessly to a computer program in the base station, which will display (inclusive of augmented reality) the images on the computer screen of the base station, and the patient may interact with the smartphone wirelessly via the base station.

Figure 7:
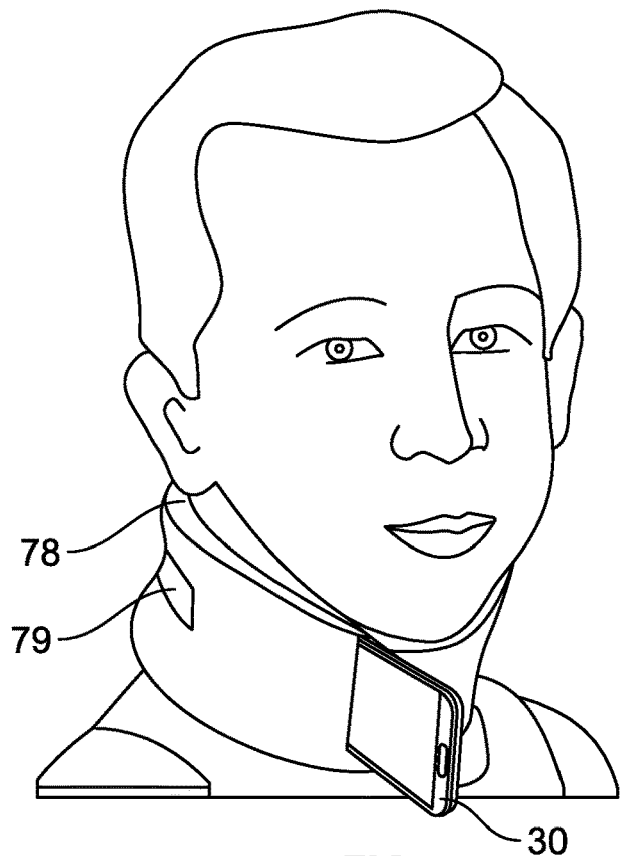
FIG. 7 illustrates an embodiment of an approximate position of a stimulator according to this disclosure, when used to stimulate a right vagus nerve in a neck of a child who wears a collar to hold the stimulator.

FIG. 7 shows the stimulator 30 applied to the neck of a child, which is partially immobilized with a foam cervical collar 78 that is similar to ones used for neck injuries and neck pain. The collar is tightened with a strap 79, and the stimulator is inserted through a hole in the collar to reach the child's neck surface. In such applications, the stimulator may be turned on and off remotely, using a wireless controller that may be used to adjust the stimulation parameters of the controller (e.g., on/off, stimulation amplitude, frequency, etc.).

Figure 8:
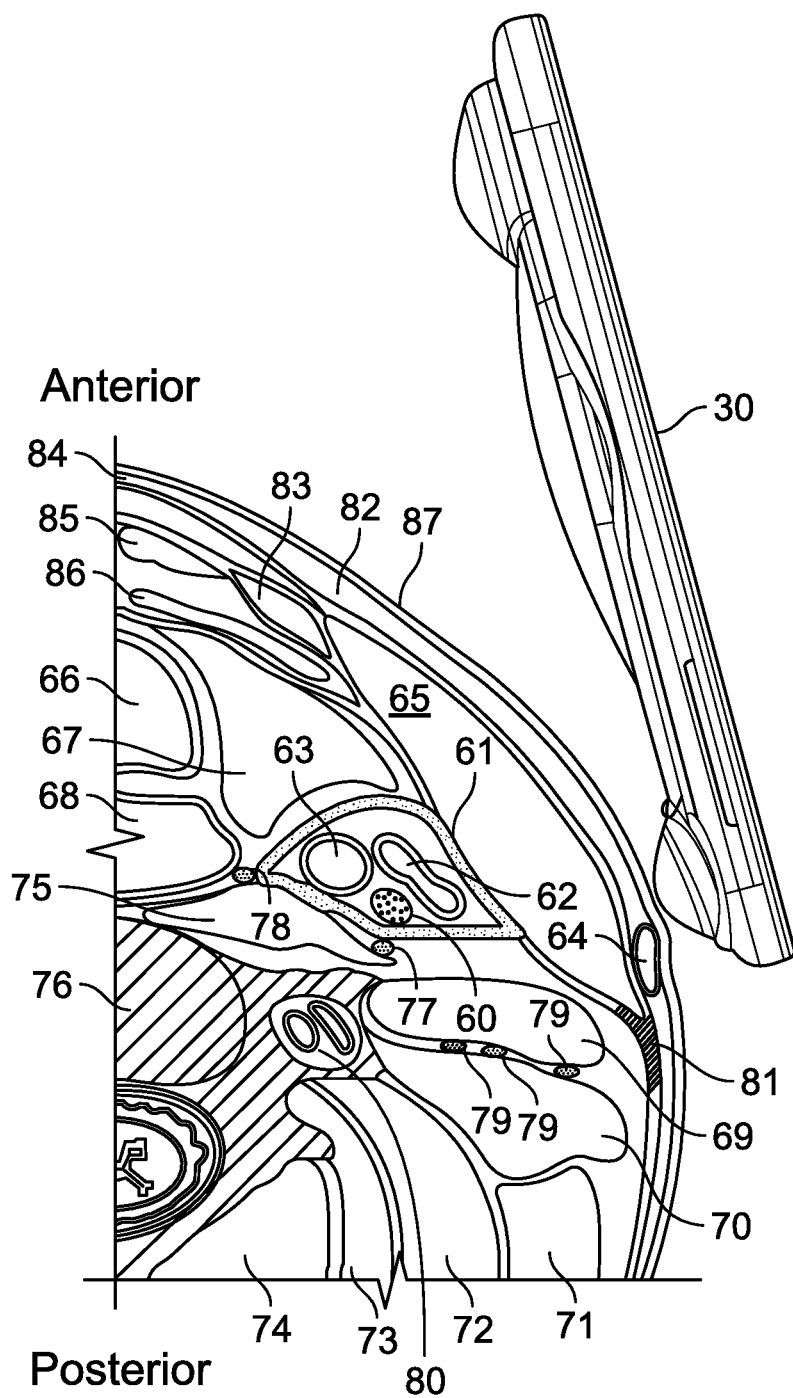
FIG. 8 illustrates an embodiment of a stimulator according to this disclosure, when positioned to stimulate a vagus nerve in a patient's neck, wherein the stimulator is applied to a surface of the neck in a vicinity of various identified anatomical structures.
Figure 9:
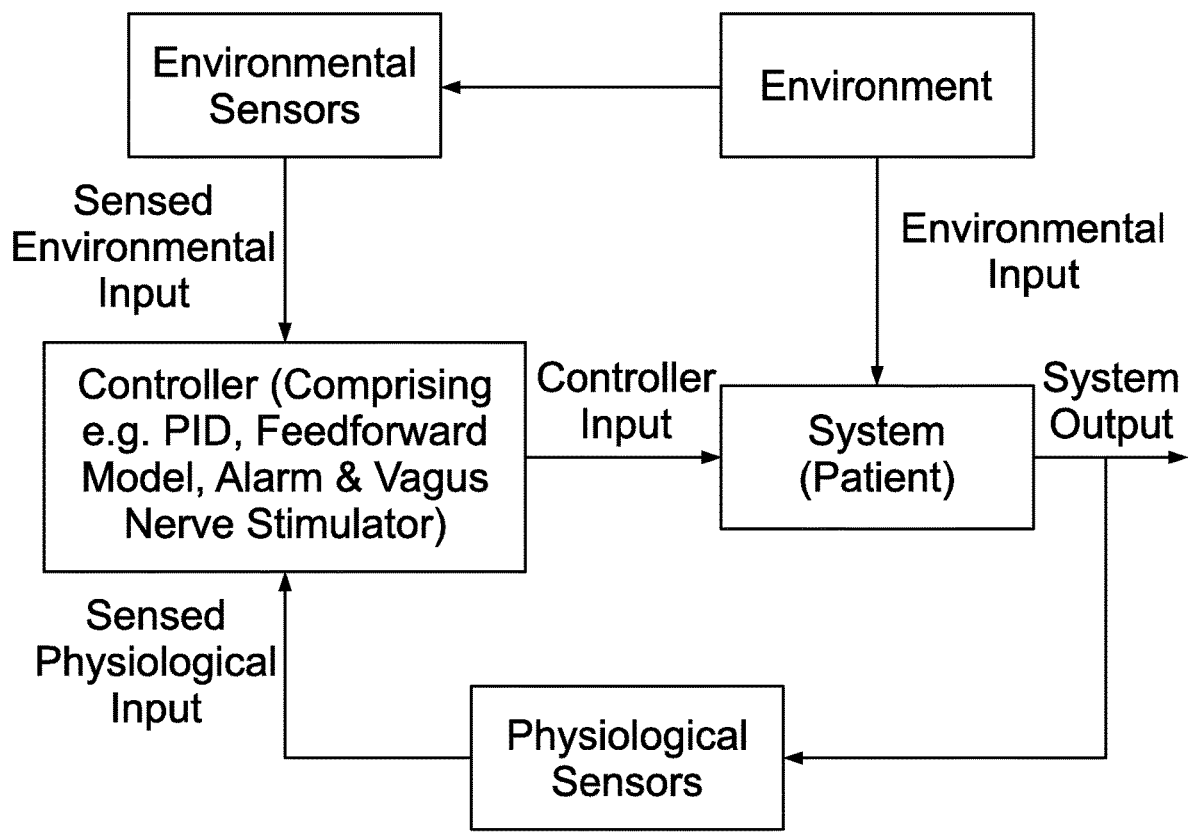
FIG. 9 illustrates an embodiment of connections between a controller and a controlled system according to this disclosure, their input and output signals, and external signals from an ambient environment.

FIG. 8 provides a more detailed view of use of the electrical stimulator 30, when positioned to stimulate the vagus nerve at the neck location that is indicated in FIG. 6. The anatomy shown in FIG. 8 is a cross-section of half of the neck at vertebra level C6. The vagus nerve 60 is identified in FIG. 8, along with the carotid sheath 61 that is identified there in bold peripheral outline. The carotid sheath encloses not only the vagus nerve, but also the internal jugular vein 62 and the common carotid artery 63. Structures that may be identified near the surface of the neck include the external jugular vein 64 and the sternocleidomastoid muscle 65, which protrudes when the patient turns his or her head. Additional organs in the vicinity of the vagus nerve include the trachea 66, thyroid gland 67, esophagus 68, scalenus anterior muscle 69, scalenus medius muscle 70, levator scapulae muscle 71, splenius colli muscle 72, semispinalis capitis muscle 73, semispinalis colli muscle 74, longus colli muscle and longus capitis muscle 75. The sixth cervical vertebra 76 is shown with bony structure indicated by hatching marks. Additional structures shown in the figure are the phrenic nerve 77, sympathetic ganglion 78, brachial plexus 79, vertebral artery and vein 80, prevertebral fascia 81, platysma muscle 82, omohyoid muscle 83, anterior jugular vein 84, sternohyoid muscle 85, sternothyroid muscle 86, and skin with associated fat 87.

Some methods of treating a patient comprise stimulating the vagus nerve as indicated in FIGS. 6, 7, and 8, using the electrical stimulation devices that are disclosed herein. Stimulation may be performed on the left or right vagus nerve or on both of them simultaneously or alternately. The position and angular orientation of the device are adjusted about that location until the patient perceives stimulation when current is passed through the stimulator electrodes. The applied current is increased gradually, first to a level wherein the patient feels sensation from the stimulation. The power is then increased, but is set to a level that is less than one at which the patient first indicates any discomfort. Straps, harnesses, or frames may be used to maintain the stimulator in position. The stimulator signal may have a frequency and other parameters that are selected to produce a therapeutic result in the patient, i.e., stimulation parameters for each patient are adjusted on an individualized basis. Ordinarily, the amplitude of the stimulation signal is set to the maximum that is comfortable for the patient, and then the other stimulation parameters are adjusted.

The stimulation is then performed with a sinusoidal burst waveform like that shown in FIG. 2. As seen there, individual sinusoidal pulses have a period of T, and a burst consists of N such pulses. This is followed by a period with no signal (the inter-burst period). The pattern of a burst followed by silent inter-burst period repeats itself with a period of T. For example, the sinusoidal period T may be between about 50-1000 microseconds (substantially equivalent to about 1-20 KHz), preferably between about 100-400 microseconds (substantially equivalent to about 2.5-10 KHz), more preferably about 133-400 microseconds (substantially equivalent to about 2.5-7.5 KHZ) and even more preferably about 200 microseconds (substantially equivalent to about 5 KHz); the number of pulses per burst may be N=1-20, preferably about 2-10 and more preferably about 5; and the whole pattern of burst followed by silent inter-burst period may have a period T comparable to about 10-100 Hz, preferably about 15-50 Hz, more preferably about 25-35 Hz and even more preferably about 25 Hz (a much smaller value of T is shown in FIG. 2C to make the bursts discernable). When these example values are used for T and T, the waveform contains significant Fourier components at higher frequencies (1/200 microseconds=5000/sec), as compared with those contained in transcutaneous nerve stimulation waveforms.

When a patient is using the stimulation device to perform self-stimulation therapy, e.g., at home or at a workplace, he or she will follow the steps that are now described. It is assumed that the optimal stimulation position has already been marked on the patient's neck, as described above and that a reference image of the fluorescent spots has already been acquired. The previous stimulation session will ordinarily have discharged the rechargeable batteries of the stimulator housing, and between sessions, the base station will have been used to recharge the stimulator at most only up to a minimum level. If the stimulator's batteries had charge remaining from the previous stimulation session, the base station will discharge the stimulator to a minimum level that will not support stimulation of the patient.

The patient can initiate the stimulation session using the mobile phone or base station (e.g., laptop computer) by invoking a computer program (on the laptop computer or through an app on the mobile phone) that is designed to initiate use of the stimulator. The programs in the smartphone and base station may initiate and interact with one another wirelessly, so in what follows, reference to the program (app) in the smartphone may also apply to the program in the base station, because both may be operating in tandem. For security reasons, the program would begin with the request for a user name and a password, and that user's demographic information and any data from previous stimulator experiences would already be associated with it in the login account. The smartphone may also be used to authenticate the patient using a fingerprint or voice recognition app, or other reliable authentication methods. If the patient's physician has not authorized further treatments, the base station will not charge the stimulator's batteries, and instead, the computer program will call or otherwise communicate with the physician's computer requesting authorization. After authorization by the physician is received, the computer program (on the laptop computer or through an app on the mobile phone) may also query a database that is ordinarily located somewhere on the internet to verify that the patient's account is in order. If it is not in order, the program may then request prepayment for one or more stimulation sessions, which would be paid by the patient using a credit card, debit card, PayPal, cryptocurrency, bitcoin, or the like. The computer program will also query its internal database or that of the base station to determine that sufficient time has elapsed between when the stimulator was last used and the present time, to verify that any required wait-time has elapsed.

Having received authorization to perform a nerve stimulation session, the patient interface computer program will then ask the patient questions that are relevant to the selection of parameters that the base station will use to make the stimulator ready for the stimulation session. The questions that the computer program asks are dependent on the condition for which the patient is being treated, which for present purposes is considered to be treatment for an autoimmune disease or disorder. The questions may be things like (1) is this an acute or prophylactic treatment? (2) if acute, then how severe is your pain and in what locations, how long have you had it, (3) has anything unusual or noteworthy occurred since the last stimulation?, etc.

Having received such preliminary information from the patient, the computer programs will perform instrument diagnostic tests and make the stimulator ready for the stimulation session. In general, the algorithm for setting the stimulator parameters will have been decided by the physician and will include the extent to which the stimulator batteries should be charged, which the vagus nerve should be stimulated (right or left), and the time that the patient should wait after the stimulation session is ended until initiation of a subsequent stimulation session. The computer will query the physician's computer to ascertain whether there have been any updates to the algorithm, and if not, will use the existing algorithm. The patient will also be advised of the stimulation session parameter values by the interface computer program, so as to know what to expect.

Once the base station has been used to charge the stimulator's batteries to the requisite charge, the computer program (or smartphone app) will indicate to the patient that the stimulator is ready for use. At that point, the patient would clean the electrode surfaces, and make any other preliminary adjustments to the hardware. The stimulation parameters for the session will be displayed, and any options that the patient is allowed to select may be made. Once the patient is ready to begin, he or she will press a "start" button on the touchscreen and may begin the vagus nerve stimulation, as shown in FIG. 6.

Multiple methods may be used to test whether the patient is properly attempting to stimulate the vagus nerve (or another nerve or organ or muscle or bone) on the intended side of the neck (or another portion of a human body). For example, accelerometers and gyroscopes within the smartphone may be used to determine the position and orientation of the smartphone's touch screen relative to the patient's expected view of the screen, and a decision by the stimulator's computer program as to which hand is being used to hold the stimulator may be made by measuring capacitance on the outside of the stimulator body, which may distinguish fingers wrapped around the device versus the ball of a thumb [Raphael WIMMER and Sebastian Boring. HandSense: discriminating different ways of grasping and holding a tangible user interface. Proceedings of the 3rd International Conference on Tangible and Embedded Interaction, pp. 359-362. ACM New York, NY, 2009, the disclosure of which is incorporated herein by reference for all purposes as if copied and pasted herein]. Pressing of the electrodes against the skin will result in a resistance drop across the electrodes, which can initiate operation of the rear camera. A fluorescent image should appear on the smartphone screen only if the device is applied to the side of the neck in the vicinity of the fluorescent spots that had been applied as a tattoo earlier. If the totality of these data indicates to the computer program that the patient is attempting to stimulate the wrong vagus nerve or that the device is being held improperly, the stimulation will be withheld, and the stimulator may then communicate with the patient via the interface computer program (in the mobile phone or laptop computer) to alert the patient of that fact. The program may then offer suggestions on how to better apply the device to the neck.

However, if the stimulator is being properly applied, and an image of the fluorescent spots on the patient's neck appears on the screen of the phone, the stimulator begins to stimulate according to predetermined initial stimulus parameters. The patient will then adjust the position and angular orientation of the stimulator about what he or she thinks is the correct neck position, until he or she perceives stimulation when current is passed through the stimulator electrodes. An attempt is also made to superimpose the currently viewed fluorescence image of the neck spots with the previously acquired reference image. The applied current is increased gradually using keys on the keyboard of the base station or on the smartphone touchscreen, first to a level wherein the patient feels sensation from the stimulation. The stimulation amplitude is then increased by the patient, but is set to a level that is less than one at which he first senses any discomfort. By trial and error, the stimulation is then optimized by the patient, who tries to find the greatest acceptable sensation with the lowest acceptable stimulation amplitude, with the stimulator aligned using the fluorescent spots. If the stimulator is being held in place by hand, it is likely that there may be inadvertent fluctuating movement of the stimulator, due for example to neck movement during respiration. Such relative movements will affect the effectiveness of the stimulation. However, they may be monitored by accelerometers and gyroscopes within the smartphone, which may be transmitted as movement data from the stimulator to the patient interface computer program (in the mobile phone or laptop computer). The relative movements may also be monitored and measured as fluctuations in the position of the fluorescence spots that are being imaged. By watching a graphical display of the relative movements shown by the patient interface computer program, the patient may use that display in an attempt to deliberately minimize the movements. Otherwise, the patient may attempt to adjust the amplitude of the stimulator as compensation for movement of the stimulator away from its optimum position. In a section that follows, it is described how the stimulator itself may modulate the amplitude of the stimulation in order to make such compensations.

During the session, the patient may lift the stimulator from his neck, which will be detected as an increase in resistance between the electrodes and a loss of the fluorescent image of the spots on the patient's neck. When that occurs, the device will withhold power to the stimulator for reasons of safety. The patient can then reapply the stimulator to his neck to resume the session, although the interruption of stimulation will be recognized and recorded by the computer program. Stimulation by the patient will then continue until the battery of the stimulator is depleted, or the patient decides to terminate the stimulation session. At that point, the patient will acknowledge that the stimulation session is finished by touching a response button on the smartphone screen, whereupon the stimulator will transfer to the base station data that its microprocessor has caused to be stored regarding the stimulation session (e.g., stimulation amplitude as a function of time and information about movements of the device during the session, duration of the stimulation, the existence of interruptions, etc.). Such information will then be transmitted to and displayed by the patient interface computer program (in the mobile phone or laptop computer), which will subsequently ask the patient questions regarding the effectiveness of the stimulation. Such questions may be in regard to the post-stimulation severity of the headache, whether the severity decreased gradually or abruptly during the course of the stimulation, and whether anything unusual or noteworthy occurred during the stimulation. Some, most, many, or all of such post-stimulation data will also be delivered over the internet by the patient interface computer program to the physician's computer for review and possible adjustment of the algorithm that is used to select stimulation parameters and regimens. It is understood that the physician will adjust the algorithm based not only on the experience of each individual patient, but on the experience of all patients collectively so as to improve effectiveness of the stimulator's use, for example, by identifying characteristics of most and least responsive patients.

Before logging off of the interface computer program, the patient may also review database records and summaries about all previous treatment sessions, so as to make his or her own judgment about treatment progress. If the stimulation was part of a prophylactic treatment regimen that was prescribed by the patient's physician, the patient interface computer program will remind the patient about the schedule for the upcoming self-treatment sessions and allow for a rescheduling if necessary.

For some patients, the stimulation may be performed for as little as 90 seconds, but it may also be for up to 30 minutes or longer. The treatment is generally performed once or twice daily or several times a week, for 12 weeks or longer before a decision is made as to whether to continue the treatment. For patients experiencing intermittent symptoms, the treatment may be performed only when the patient is symptomatic. However, it is understood that parameters of the stimulation protocol may be varied in response to heterogeneity in the pathophysiology of patients. Different stimulation parameters may also be used as the course of the patient's condition changes.

In some embodiments, pairing of vagus nerve stimulation may be with an additional sensory stimulation. The paired sensory stimulation may be bright light, sound, tactile stimulation, or electrical stimulation of the tongue to simulate odor/taste, e.g., pulsating with the same frequency as the vagus nerve electrical stimulation. The rationale for paired sensory stimulation is the same as simultaneous, paired stimulation of both left and right vagus nerves, namely, that the pair of signals interacting with one another in the brain may result in the formation of larger and more coherent neural ensembles than the neural ensembles associated with the individual signals, thereby enhancing the therapeutic effect. This pairing may be considered especially when some such corresponding sensory circuit of the brain is thought to be partly responsible for triggering the migraine headache.

Selection of stimulation parameters to preferentially stimulate particular regions of the brain may be done empirically, wherein a set of stimulation parameters are chosen, and the responsive region of the brain is measured using fMRI or a related imaging method [CHAE J H, Nahas Z, Lomarev M, Denslow S, Lorberbaum J P, Bohning D E, George M S. A review of functional neuroimaging studies of vagus nerve stimulation (VNS). J Psychiatr Res. 37(6,2003): 443-455, the disclosure of which is incorporated herein by reference for all purposes as if copied and pasted herein; CONWAY C R, Sheline Y I, Chibnall J T, George M S, Fletcher J W, Mintun M A. Cerebral blood flow changes during vagus nerve stimulation for depression. Psychiatry Res. 146(2,2006):179-84, the disclosure of which is incorporated herein by reference for all purposes as if copied and pasted herein]. Thus, by performing the imaging with different sets of stimulation parameters, a database may be constructed, such that the inverse problem of selecting parameters to match a particular brain region may be solved by consulting the database.

The individualized selection of parameters for the nerve stimulation protocol may be based on trial and error in order to obtain a beneficial response without the sensation of skin pain or muscle twitches. Alternatively, the selection of parameter values may involve tuning as understood in control theory, as described below. It is understood that parameters may also be varied randomly in order to simulate normal physiological variability, thereby possibly inducing a beneficial response in the patient [Buchman T G. Nonlinear dynamics, complex systems, and the pathobiology of critical illness. Curr Opin Crit Care 10(5,2004):378-82, the disclosure of which is incorporated herein by reference for all purposes as if copied and pasted herein].

In some embodiments, various methods can use vagal nerve stimulation to suppress inflammation. In some embodiments, some methods and devices involve the inhibition of pro-inflammatory cytokines, or more specifically, stimulation of the vagus nerve to inhibit and/or block the release of such pro-inflammatory cytokines. In some embodiments, some methods and devices use vagal nerve stimulation to increase the concentration or effectiveness of anti-inflammatory cytokines. TRACEY et al do not consider the modulation of anti-inflammatory cytokines to be part of the cholinergic anti-inflammatory pathway that their method of vagal nerve stimulation is intended to activate. Thus, they explain that "activation of vagus nerve cholinergic signaling inhibits TNF (tumor necrosis factor) and other proinflammatory cytokine overproduction through 'immune' a7 nicotinic receptor-mediated mechanisms" [V. A. PAVLOV and K. J. Tracey. Controlling inflammation: the cholinergic anti-inflammatory pathway. Biochemical Society Transactions 34, (2006, 6): 1037-1040, the disclosure of which is incorporated herein by reference for all purposes as if copied and pasted herein]. In contrast, anti-inflammatory cytokines are said to be part of a different "diffusible anti-inflammatory network, which includes glucocorticoids, anti-inflammatory cytokines, and other humoral mediators" [CZURA C J, Tracey K J. Autonomic neural regulation of immunity. J Intern Med. 257(2005, 2): 156-66, the disclosure of which is incorporated herein by reference for all purposes as if copied and pasted herein]. Others make a similar distinction between vagal and humoral mediation [GUYON A, Massa F, Rovère C, Nahon J L. How cytokines can influence the brain: a role for chemokines? J Neuroimmunol 2008; 198: 46-55, the disclosure of which is incorporated herein by reference for all purposes as if copied and pasted herein].

The disclaiming by TRACEY and colleagues of a role for anti-inflammatory cytokines as mediators of inflammation following stimulation of the vagus nerve may be due to a recognition that anti-inflammatory cytokines (e.g., TGF-β) are usually produced constitutively, while pro-inflammatory cytokines (e.g., TNF-alpha) are not produced constitutively, but are instead induced. However, anti-inflammatory cytokines are inducible as well as constitutive, so that for example, an increase in the concentrations of potentially anti-inflammatory cytokines such as transforming growth factor-beta (TGF-13) can in fact be accomplished through stimulation of the vagus nerve [RA BAUMGARTNER, V A Deramo and MA Beaven. Constitutive and inducible mechanisms for synthesis and release of cytokines in immune cell lines. The Journal of Immunology 157 (1996, 9): 4087-4093, the disclosure of which is incorporated herein by reference for all purposes as if copied and pasted herein; CORCORAN, Ciaran; Connor, Thomas J; O'Keane, Veronica; Garland, Malcolm R. The effects of vagus nerve stimulation on pro- and anti-inflammatory cytokines in humans: a preliminary report. Neuroimmunomodulation 12 (5, 2005): 307-309, the disclosure of which is incorporated herein by reference for all purposes as if copied and pasted herein].

An example of a pro-anti-inflammatory mechanism that is particularly relevant to the treatment of multiple sclerosis is as follows. TGF-β converts undifferentiated T cells into regulatory T (Treg) cells that block the autoimmunity that causes demyelination in multiple sclerosis. However, in the presence of interleukin-6, TGF-β also causes the differentiation of T lymphocytes into proinflammatory IL-17 cytokine-producing T helper 17 (TH17) cells, which promote autoimmunity and inflammation. Thus, it is conceivable that an increase of TGF-β levels might actually cause or exacerbate inflammation, rather than suppress it. Accordingly, a step in an embodiment of the methods that are disclosed herein is to deter TGF-β from realizing its pro-inflammatory potential, by selecting nerve stimulation parameters that bias the potential of TGF-β towards anti-inflammation, and/or by treating the patient with an agent such as the vitamin A metabolite retinoic acid that is known to promote such an anti-inflammatory bias [MUCIDA D, Park Y, Kim G, Turovskaya O, Scott I, Kronenberg M, Cheroutre H. Reciprocal TH17 and regulatory T cell differentiation mediated by retinoic acid. Science 317(2007, 5835): 256-60, the disclosure of which is incorporated herein by reference for all purposes as if copied and pasted herein; Sheng XIAO, Hulin Jin, Thomas Korn, Sue M. Liu, Mohamed Oukka, Bing Lim, and Vijay K. Kuchroo. Retinoic acid increases Foxp3+ regulatory T cells and inhibits development of Th17 cells by enhancing TGF-β-driven Smad3 signaling and inhibiting IL-6 and IL-23 receptor expression. J Immunol. 181(2008, 4): 2277-2284, the disclosure of which is incorporated herein by reference for all purposes as if copied and pasted herein]. Retinoic acid is a member of a class of compounds known as retinoids, comprising three generations: (1) retinol, retinal, retinoic acid (tretinoin, Retin-A), isotretinoin and alitretinoin; (2) etretinate and acitretin; (3) tazarotene, bexarotene and Adapalene.

In some embodiments, endogenous retinoic acid that is released by neurons themselves is used to produce the anti-inflammatory bias. Thus, vagal nerve stimulation may induce differentiation through release of retinoic acid that is produced in neurons from retinaldehyde by retinaldehyde dehydrogenases, and some embodiments disclosed herein can promote anti-inflammatory regulatory T cell (Treg) differentiation by this type of mechanism [van de PAVERT S A, Olivier B J, Goverse G, Vondenhoff M F, Greuter M, Beke P, Kusser K, Höpken U E, Lipp M, Niederreither K, Blomhoff R, Sitnik K, Agace W W, Randall T D, de Jonge W J, Mebius R E. Chemokine CXCL13 is essential for lymph node initiation and is induced by retinoic acid and neuronal stimulation. Nat Immunol. 10(11, 2009): 1193-1199, the disclosure of which is incorporated herein by reference for all purposes as if copied and pasted herein].

The retinoic acid so released might also directly inhibit the release or functioning of proinflammatory cytokines, which would be an anti-pro-inflammatory mechanism that is distinct from the one proposed by TRACEY and colleagues [Malcolm Maden. Retinoic acid in the development, regeneration and maintenance of the nervous system. Nature Reviews Neuroscience 8(2007), 755-765, the disclosure of which is incorporated herein by reference for all purposes as if copied and pasted herein]. However, if the proinflammatory cytokine that is blocked is TNF-alpha, its inhibition in multiple sclerosis patients might be counterproductive. This is because blocking TNF-alpha with the drug lenercept promotes and exacerbates multiple sclerosis attacks rather than delaying them, which might be attributable to the fact that TNF-alpha promotes remyelination and the proliferation of oligodendrocytes that perform the myelination. [ANONYMOUS. TNF neutralization in MS: Results of a randomized, placebo controlled multicenter study. Neurology 1999, 53:457, the disclosure of which is incorporated herein by reference for all purposes as if copied and pasted herein; ARNETT H A, Mason J, Marino M, Suzuki K, Matsushima G K, Ting J P. TNF alpha promotes proliferation of oligodendrocyte progenitors and remyelination. Nat Neurosci 2001, 4:1116-1122, the disclosure of which is incorporated herein by reference for all purposes as if copied and pasted herein].

In this example, the competence of anti-inflammatory cytokines may be modulated by the retinoic acid (RA) signaling system of the nervous system. The most important mechanism of RA activity is the regulation of gene expression. This is accomplished by its binding to nuclear retinoid receptors that are ligand-activated transcription factors. Thus, RA acts as a transcriptional activator for a large number of other, downstream regulatory molecules, including enzymes, transcription factors, cytokines, and cytokine receptors. Retinoic acid is an essential morphogen in vertebrate development and participates in tissue regeneration in the adult [Jorg MEY and Peter MdCaffery. Retinoic Acid Signaling in the Nervous System of Adult Vertebrates. The Neuroscientist 10(5, 2004): 409-421, the disclosure of which is incorporated herein by reference for all purposes as if copied and pasted herein]. RA also increases synaptic strength in a homeostatic response (synaptic scaling) to neuronal inactivity through a mechanism involving protein synthesis that requires the participation of TNF-alpha. RA is also intimately involved in the control of the rhythmic electrical activity of the brain. More generally, all-trans retinoic acid, 9-cis retinoic acid, and 13-cis retinoic acid are some of a very small number of entrainment factors that regulate the natural rhythmicity of metabolic processes in many types of individual cells [Mehdi Tafti, Norbert B. Ghyselinck. Functional Implication of the Vitamin A Signaling Pathway in the Brain. Arch Neurol. 64(12,2007): 1706-1711, the disclosure of which is incorporated herein by reference for all purposes as if copied and pasted herein].

The potentially anti-inflammatory cytokine TGF-beta is a member of the TGF-beta superfamily of neurotrophic factors. Neurotrophic factors serve as growth factors for the development, maintenance, repair, and survival of specific neuronal populations, acting via retrograde signaling from target neurons by paracrine and autocrine mechanisms. Other neurotrophic factors also promote the survival of neurons during neurodegeneration. These include members of the nerve growth factor (NGF) superfamily, the glial-cell-line-derived neurotrophic factor (GDNF) family, the neurokine superfamily, and non-neuronal growth factors such as the insulin-like growth factors (IGF) family. However, major problems in using such neurotrophic factors for therapy are their inability to cross the blood-brain-barrier, adverse effects resulting from binding to the receptor in other organs of the body and their low diffusion rate [Yossef S. Levy, Yossi Gilgun-Sherki, Eldad Melamed and Daniel Offen. Therapeutic Potential of Neurotrophic Factors in Neurodegenerative Diseases. Biodrugs 2005; 19 (2): 97-127, the disclosure of which is incorporated herein by reference for all purposes as if copied and pasted herein].

It is known that vagal nerve stimulation and transcranial magnetic stimulation can increase the levels of at least one neurotrophic factor in the brain, namely, brain-derived neurotrophic factor (BDNF) in the NGF superfamily, which has been studied extensively in connection with the treatment of depression. However, vagal nerve stimulation to increase levels of neurotrophic factors has not been reported in connection with neurodegenerative diseases. Because BDNF may be modulated by stimulating the vagus nerve, vagal nerve stimulation may likewise promote the expression of other neurotrophic factors in patients with neurodegenerative disease, thereby circumventing the problem of blood-brain barrier blockage [Follesa P, Biggio F, Gorini G, Caria S, Talani G, Dazzi L, Puligheddu M, Marrosu F, Biggio G. Vagus nerve stimulation increases norepinephrine concentration and the gene expression of BDNF and bFGF in the rat brain. Brain Research 1179(2007): 28-34, the disclosure of which is incorporated herein by reference for all purposes as if copied and pasted herein; Biggio F, Gorini G, Utzeri C, Olla P, Marrosu F, Mocchetti I, Follesa P. Chronic vagus nerve stimulation induces neuronal plasticity in the rat hippocampus. Int J Neuropsychopharmacol. 12(9, 2009):1209-21, the disclosure of which is incorporated herein by reference for all purposes as if copied and pasted herein; Roberta Zanardini, Anna Gazzoli, Mariacarla Ventriglia, Jorge Perez, Stefano Bignotti, Paolo Maria Rossini, Massimo Gennarelli, Luisella Bocchio-Chiavetto. Effect of repetitive transcranial magnetic stimulation on serum brain derived neurotrophic factor in drug resistant depressed patients. Journal of Affective Disorders 91 (2006) 83-86, the disclosure of which is incorporated herein by reference for all purposes as if copied and pasted herein]. US Patent Application Publication US20100280562, the disclosure of which is incorporated herein by reference for all purposes as if copied and pasted herein, entitled Biomarkers for monitoring treatment of neuropsychiatric diseases, to PI et al, disclosed the measurement of GDNF and other neurotrophic factors following vagal nerve stimulation. However, that application is concerned with the search for biomarkers involving the levels of GDNF, rather than a method for treating autoimmune diseases using vagal nerve stimulation.

Figure 10:
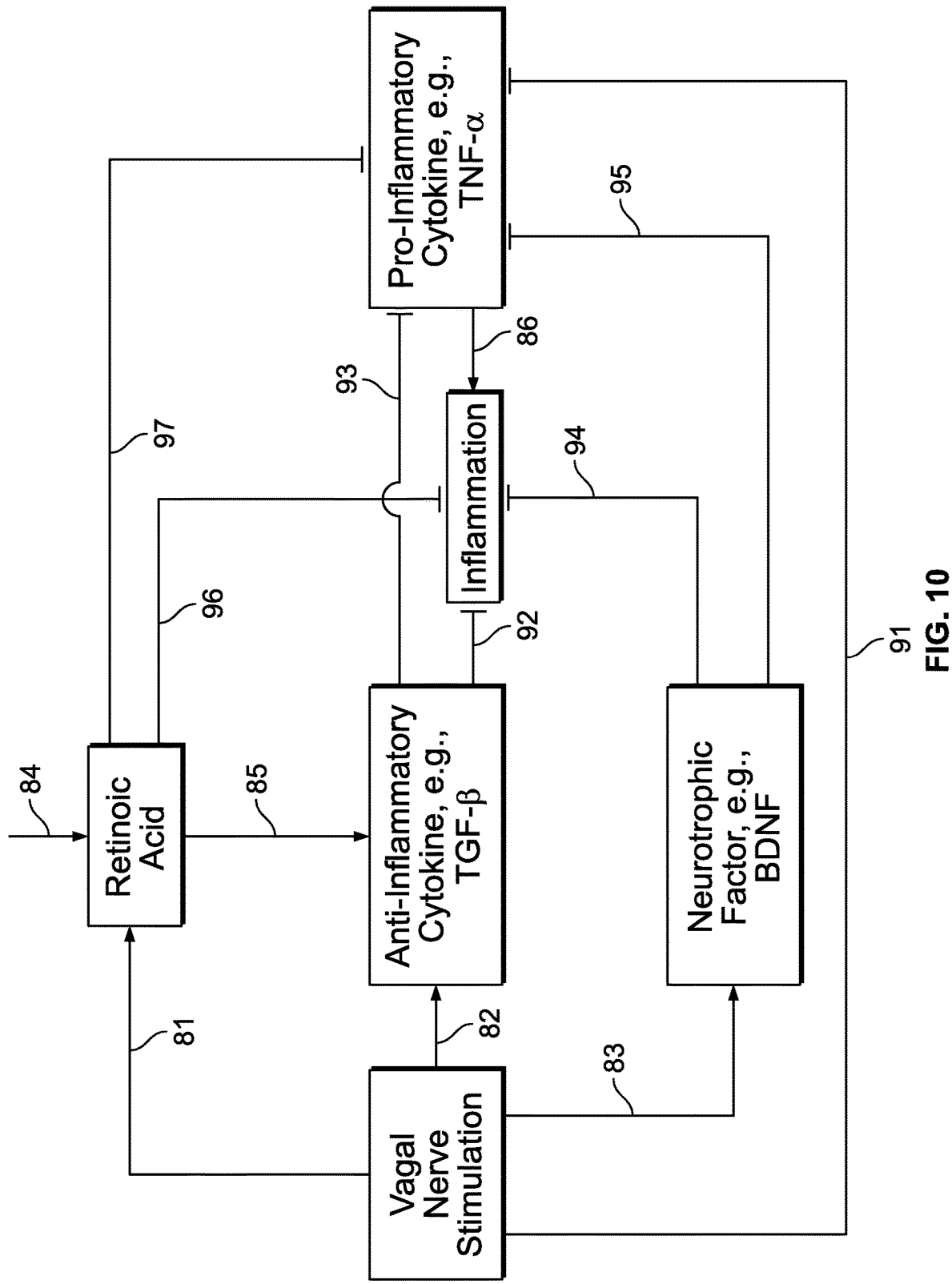
FIG. 10 illustrates an embodiment of mechanisms or pathways through which stimulation of the vagus nerve may reduce inflammation in patients with neurodegenerative or autoimmune disorders according to this disclosure.

FIG. 10 illustrates mechanisms or pathways through which stimulation of the vagus nerve may be used to reduce inflammation in patients with neurodegenerative disorders. In what follows, each of the mechanisms or pathways is described in connection with treatment of particular disorders, namely, Alzheimer's disease, Parkinson's disease, multiple sclerosis, Sjôgren's syndrome, Type 2 diabetes, RA and fibromyalgia. However, it is understood that the treatment of other autoimmune disease or disorders using vagal nerve stimulation may also make use of methods involving these mechanisms or pathways. It is also understood that not all of the pathways or mechanisms may be used in the treatment of a particular patient and that pathways or mechanisms that are not shown in FIG. 10 may also be used. Thus, particular pathways or mechanisms are invoked by the selection of particular stimulation parameters, such as current, frequency, pulse width, duty cycle, etc. Nevertheless, as an aid to understanding the applications that follow, it is useful to consider at once all the mechanisms shown in FIG. 10.

Two types of pathways are shown in FIG. 10. The pathways that stimulate or upregulate are indicated with an arrow ( ). The pathways that inhibit or downregulate are indicated with a blockage bar ( ). Pathways resulting from stimulation of the vagus nerve are shown to stimulate retinoic acid 81, anti-inflammatory cytokines 82 such as TGF-beta, and neurotrophic factors 83 such as BDNF. The patient may also be treated with retinoic acid or some other retinoid by administering it as a drug 84. For cytokines that may have both anti-inflammatory and pro-inflammatory capabilities, the retinoic acid biases such cytokines to exhibit their anti-inflammatory potential, as shown in the pathway labeled as 85. Pro-inflammatory cytokines, on the other hand, promote inflammation by pathways labeled as 86. Stimulation of the vagus nerve inhibits the release of pro-inflammatory cytokines 91 directly through pathways that have been described by TRACEY and colleagues. The other pathways shown in FIG. 8 to inhibit inflammation following stimulation of the vagus nerve are novel to this disclosure, and include inhibition of inflammation via anti-inflammatory cytokine pathways 92 including those that inhibit the release of pro-inflammatory cytokines 93, inhibition via neurotrophic factors 94 including those that inhibit the release of pro-inflammatory cytokines 95, and inhibition via retinoic acid pathways 96 including those that inhibit the release of pro-inflammatory cytokines 97.

It is understood that the labels in FIG. 10 that are used for simplicity to describe the pathways actually refer to a large set of related pathways. For example, the box labeled as "retinoic acid" actually refers to not only retinoic acid but also to a larger class of retinoids, as well as to retinaldehyde dehydrogenases, retinoic acid receptors (RAR), retinoid X receptors (RXR), retinoic acid response elements (RAREs), and more generally to the retinoic acid signaling system of the nervous system and related pathways.

Furthermore, it is understood that the box labeled "Anti-Inflammatory Cytokine, e.g., TGF-beta" can actually be placed within the box entitled "Neurotrophic Factor", because TFG-beta is a member of the superfamily of TGF-beta neurotrophic factors [Yossef S. Levy, Yossi Gilgun-Sherki, Eldad Melamed and Daniel Offen. Therapeutic Potential of Neurotrophic Factors in Neurodegenerative Diseases. Biodrugs 2005; 19 (2): 97-127, the disclosure of which is incorporated herein by reference for all purposes as if copied and pasted herein]. However, because TGF-beta is ordinarily referred to simply as a cytokine, and because its anti-inflammatory competence is known to be influenced by retinoic acid, it was placed in a separate box to avoid undue confusion.

The role of the sympathetic nervous system (SNS) in the regulation of the immune system has been long appreciated through the activity of the hypothalamicpituitary-adrenal axis (HPA) and through which corticosteroids (cortisol) and other naturally occurring immunosuppressive compounds are released (Rook, 1999). In parallel with this understanding, beginning in the 1930s and 1940s, it was observed that a splenectomy could provide relief from severe inflammatory conditions such as Rheumatoid arthritis (Bach, 1946). It was a natural extension of these two lines of thinking, therefore, to attempt to modulate the splenic nerve (an element of the SNS) and identify how the immune system was impacted. The effects of stimulating these neural inputs to the spleen began to be reported as early as the 1960s (Davies et al., 1968) (FIG. 132.1).

Besedovsky et al. (1979) described the SNS as playing an important role in a feedback loop that coupled lymphoid organ activity to the CNS. In this model, the efferent arm of the SNS projects to immune system organs, releasing NE from sympathetic nerve terminals in these organs (Elenkov et al., 2000). The role of NE in modulating macrophages and other immune cells in an anti-inflammatory direction has been well established (Hu et al., 1991). Both endogenous, tonic expression, and volume transmission through extra-synaptic means, i.e., varicosities, have been proposed as a means for maintaining a baseline level of suppression over immune activity (Straub et al., 1998). With respect to the afferent arm of this feedback loop, it has been suggested that peripheral cytokine levels are able to modulate the CNS to alter sympathetic outflow. In fact, two separate groups reported, in 1989 and 1991, that infusion of IL-1! or IFN-" into the ventricles of the brain causes rapid, significant reductions in peripheral and splenic immune cell activity (Sundar et al., 1989; Brown et al., 1991). To facilitate this activation within the CNS, afferent vagal fibers were proposed as a functional pathway for peripheral cytokine modulation of the CNS (Maier et al., 1998).

Further evidence of VN involvement with splenic immune function came when Bernik et al. (2001) studied the significant peripheral, anti-inflammatory effects of semapimod (a compound formerly known as CNI-1493), which, at one point, was believed to inhibit inflammation through inhibition of p38 MAP kinase. Minute quantities of semapimod, were administered intracerebro-ventricular (ICV), just as IL-1 # and IFN-$ had been used previously. However, unlike the prior thesis of sympathetic pathway involvement, Bernik et al. reversed the assumption of efferent signaling from sympathetic to the parasympathetic (vagus), when it was found that severing of the VN abolished the anti-inflammatory effects. Their conclusion was that semapimod was a potent activator of efferent, vagal outflow (Oke et al., 2007). Borovikova et al. (2000) had previously demonstrated that electrical stimulation of the distal remains of the severed VN, i.e., the efferent vagal component, was able to trigger anti-inflammatory effects, even in the absence of ICV administration of semapimod, IL-1 #, or IFN-$. (As will be discussed later, additional studies showed that electrical stimulation of the afferent arms, postvagotomy, were also able to affect the same immune modulation.)

A review of the available literature on this subject strongly suggests that there is broad, albeit not universal, agreement that stimulation of the VN (using appropriate stimulation, signal parameters) generates a splenic nerve-mediated, anti-inflammatory effect. Initial proposals to explain the pathway suggest a simple efferent model that is based solely on acetylcholine release (the primary neurotransmitter released by efferent vagal fibers), whereby direct release of acetylcholine and binding to receptors on macrophages suppresses the production of inflammatory cytokines. The specific, efferent pathway was hypothesized to be through a binding of acetylcholine to the $7-nicotinic, acetylcholine receptor ($7nAChR), since the anti-inflammatory effect of efferent (postvagotomy) stimulation was lost in $7nAChR knockout animals (de Jonge et al., 2007).

In some embodiments, the systemic anti-inflammatory effects of VNS are believed to result from the activation of sympathetic fibers in the splenic nerve, through a connection at the celiac ganglion. These sympathetic fibers release norepinephrine into the spleen in close proximity to a specialized group of immune cells that release acetylcholine, or ACh. This release of ACh activates a receptor, the alpha 7 nicotinic ACh receptor, or 7nAChR, on cytokine-releasing immune cells called macrophages. Activation of these receptors is believed to function by blocking transcription factors that promote inflammatory cytokine expression. Based on the role of ACh in activating this pathway, which is shown in FIG. 11 below, it has been termed the cholinergic anti-inflammatory pathway, or CAP. Examples of stimulation of the vagus nerve to treat multiple sclerosis, Sjôgren's Syndrome, Rheumatoid Arthritis, and Type 2 Diabetes can be found in commonly-assigned U.S. patent application Ser. No. 16/229,401, filed Dec. 21, 2018, the complete disclosure of which is herein incorporated by reference for all purposes as if copied and pasted herein.

Embodiments of Reusable Neurostimulators

Figure 12A:
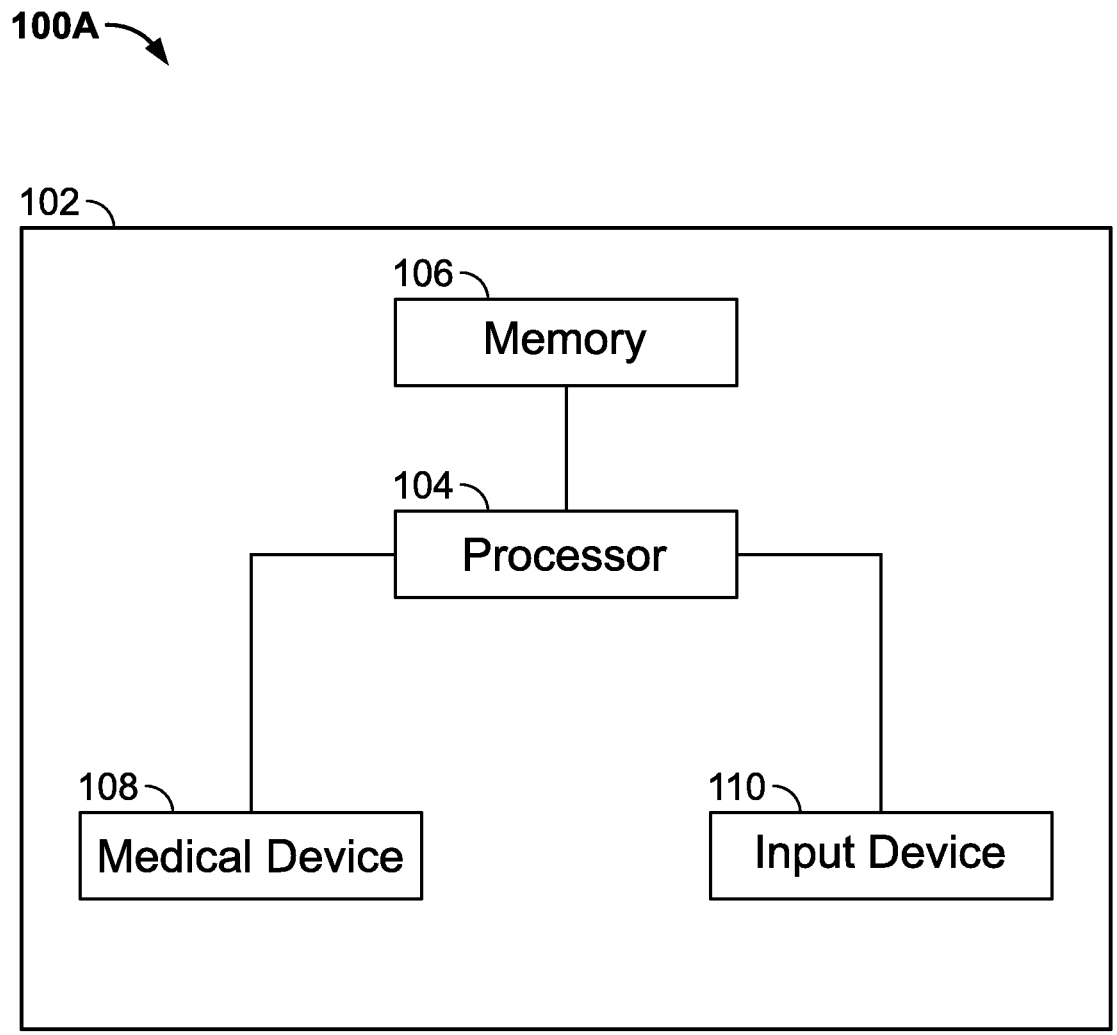
FIG. 12A is a schematic diagram of an embodiment of a system containing a medical device and an input device according to this disclosure.
Figure 12B:
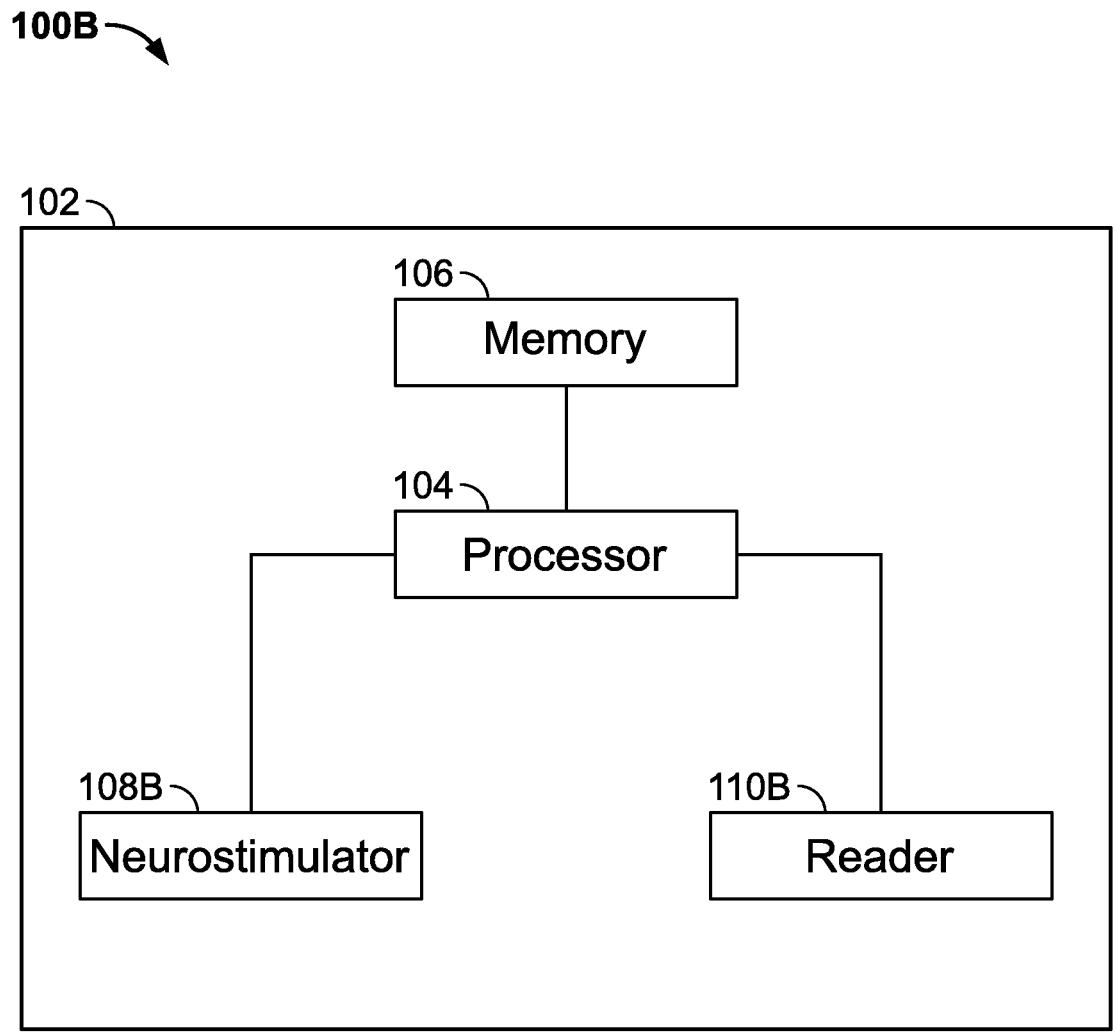
FIG. 12B is a schematic diagram of an embodiment of a system containing a neurostimulator and a reader according to this disclosure.
Figure 12C:
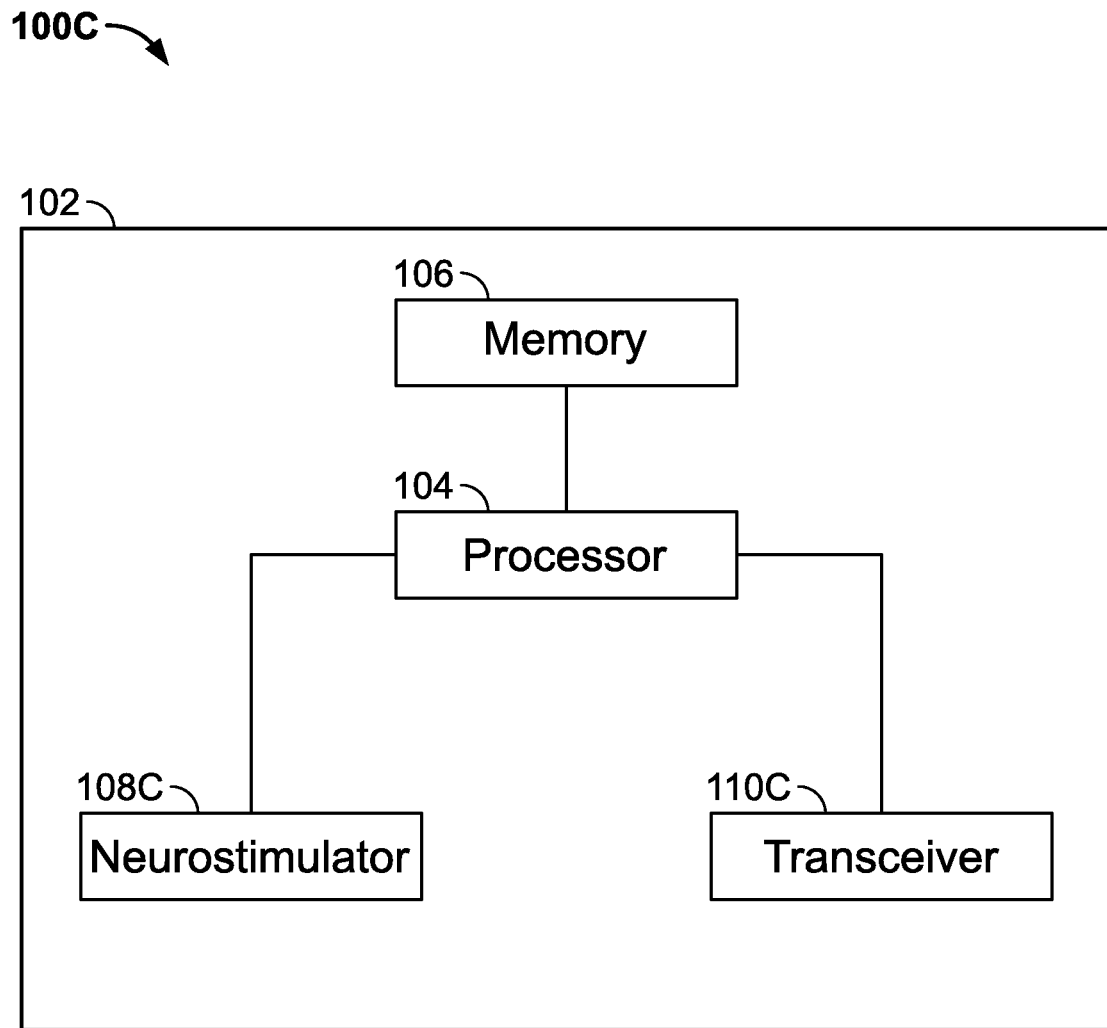
FIG. 12C is a schematic diagram of an embodiment of a system containing a neurostimulator and a transceiver according to this disclosure.
Figure 12D:
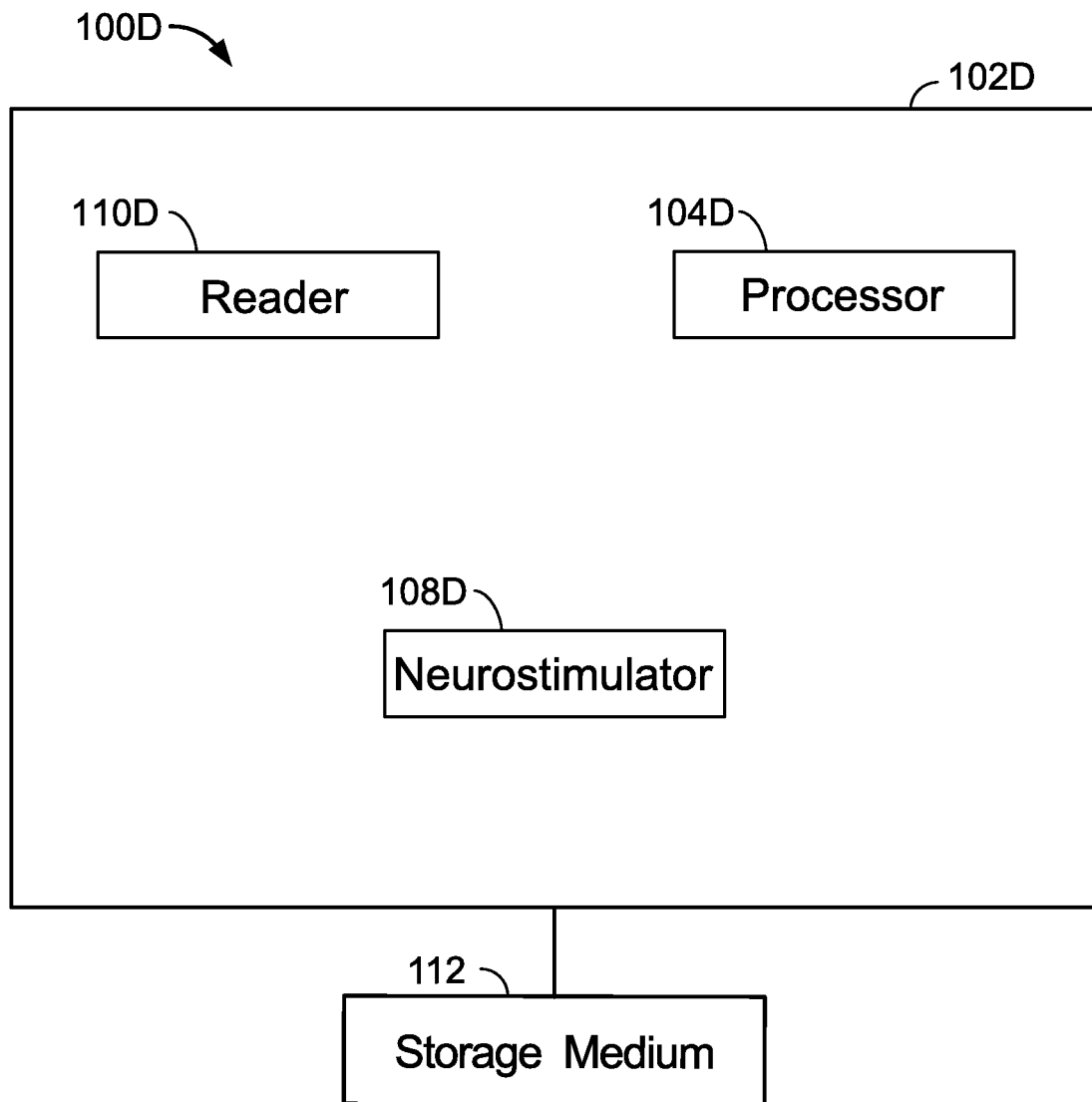
FIG. 12D is a schematic diagram of an embodiment of a system containing a neurostimulator and a storage medium according to this disclosure.

Referring now to FIGS. 12A-12D, systems and methods for refilling neurostimulator devices, such as the ones portrayed above, will now be described. FIG. 12A shows a schematic diagram of an embodiment of a system containing a medical device and an input device according to this disclosure. FIG. 12B shows a schematic diagram of an embodiment of a system containing a neurostimulator and a reader according to this disclosure. FIG. 12C shows a schematic diagram of an embodiment of a system containing a neurostimulator and a transceiver according to this disclosure. FIG. 12D shows a schematic diagram of an embodiment of a system containing a neurostimulator and a storage medium according to the present disclosure.

In particular, in FIG. 12A, a system 100A includes a housing 102, a processor 104, a memory 106, a medical device 108, and an input device 110. In FIG. 12B, a system 102B includes a housing 102, a processor 104, a memory 106, a medical device 108B and a reader 110B. In FIG. 12C, a system 102C includes a housing 102, a processor 104, a memory 106, a medical device 108C and a transceiver 110C. In FIG. 12D, a system 100D includes a medical device 102D having a reader 108D and a processor 104D, and a storage medium 112, such as a magnetic card, a radio frequency identification (RFID) card, a chip card, a barcode, a Quick Response (QR) code, or others.

The system 100D will now be more fully described although it should be noted that many of the components and elements of system 100D may be also be utilized in the systems 100A, 100B and/or 100C. System 100D includes a medical device 102D and a storage medium 112, such as a card (an example of an exemplary medical device 702 and a card 706 according to the present disclosure in shown in FIG. 20E, described in further detail below).

The system 100D is powered via a power source, such as a rechargeable or single-use battery, a mains powerline, a photovoltaic cell, a fluid turbine, or others. For example, when the system 100D is powered via the battery, then the battery can be positioned interior or exterior to the housing 102D, yet securely supported via the housing 102 (e.g., fastening, mating, interlocking, adhering, hook-and-looping). For example, the battery can be rechargeable, whether over a wired, wireless, or waveguide connection, such as via a wireless charger housed or coupled to the housing 102D. Similarly, when the system 100D is powered via the mains powerline, then the system 100D includes a conductive wire (e.g., copper, aluminum) or a cable (e.g. coaxial, data communication) spanning between the housing 102D and the mains powerline, with the conductive wire or the cable being coupled (e.g., mechanically, electrically) the housing 102D, such as via a plug, a socket, a junction box, a pigtail, or others, and the mains powerline, such as via a plug, a socket, a junction box, a pigtail, or others.

The housing 102D houses (e.g., internally, externally) the processor 104D, the reader 110D and the medical device 108D. The housing 102D can include plastic, metal, rubber, or others. The housing 102D can be rigid, elastic, resilient, or flexible. For example, the housing 102D can be included in or embodied as a phone, a tablet, a laptop, a phone/tablet/laptop case, a patch, an adhesive bandage, a strip, an anklet, a belt, a bracelet, a necklace, a garment, a pad, a ring, a mattress, a pillow, a blanket, a robot, a surgical instrument, a stimulator, an infusion device, or others. For example, the housing 102D can be embodied as described in US Patent Application Publication 20140330336 and U.S. Pat. Nos. 8,874,205, 9,174,066, 9,205,258, 9,375,571, and 9,427,581, all of which are herein incorporated by reference for all purposes as if copied and pasted herein, such as all structures, all functions, and all methods of manufacture and use, as disclosed therein. As such, the medical device 108D can be embodied as described in US Patent Application Publication 20140330336 and U.S. Pat. Nos. 8,874,205, 9,174, 066, 9,205,258, 9,375,571, and 9,427,581, all of which are herein incorporated by reference for all purposes as if copied and pasted herein, such as all structures, all functions, and all methods of manufacture and use, as disclosed therein.

In some embodiments, the housing 102D includes a plurality of housings 102, wherein the processor 104D, the reader 110D and the medical device 108D are distributed (e.g., internally, externally) among the housings 102D in any permutational or combinatory manner. For example, one of the housings 102D may include the processor 104D and the reader 110D, whereas another of the housings 102D may include the medical device 108D, where the one of the housings 102D and the another of the housings 102D are signally coupled to each other, such as via wiring, wireless, transceivers, waveguides, or others. For example, one of the housings 102D may include the processor 104D and the medical device 108D, whereas another of the housings 102D may include the reader 110D, where the one of the housings 102D and the another of the housings 102D are signally coupled to each other, such as via wiring, wireless, transceivers, waveguides, or others.

In some embodiments, the housing 102D is anti-tamper or includes an anti-tamper device or technique, such as via a mechanic or chemical technique. Note that anti-tamper or the anti-tamper device includes at least one of a tamper resistance, a tamper detection, a tamper response, or a tamper evidence. For example, the housing 102D can be mechanically anti-tamper via including a screw that can be operated with a non-standard bit. For example, the housing 102D can be chemically anti-tamper via including a tamper evident seal.

The processor 104D is coupled to the medical device 108D, and the reader 110D, such as via wiring, wireless, transceivers, waveguides, or other wireless or wired coupling methods. The processor 104D can include a single core or multicore processor. The processor 104 can be included in or be a controller, such as a programmable logic controller (PLC) or others. The processor 104 can be distinct from the medical device 108 or be a component of the medical device 108.

In some embodiments, system 102D will further include a memory 106 (see FIG. 12A). Memory 106 may be included within storage medium 112 and/or it may be included within housing 102D. The memory 106, whether volatile or non-volatile, is at least one of a mechanical memory, such as a punch card or others, or a semiconductor memory, such as a flash memory or others. The memory 106 can be distinct from the medical device 108D or be a component of the medical device 108D. The memory 106 can receive, such as via a physical recordation, a wired or wireless connection, or others, and store a logic, such as projections, depressions, holes, modules, objects, programs, apps, firmware, microcode, or other forms of instruction, for execution via the processor 104D. For example, the logic can be programmed or input via a (1) a manufacturer of the system 100D, (2) a distributor of the system 100D, (3) a retailer of the system 100D, (4) a wholesaler of the system 100D, or (5) a user of the system 100D, such as a medical service provider, a patient, or others. For example, a pharmacist can receive the system 100D programmed for use with a specific medical condition, disease, or disorder or a specific dosage or a specific patient or the pharmacist can receive the system 100D without being programmed for use with a specific medical condition, disease, or disorder or a specific dosage or a specific patient and then the pharmacist can program for use with a specific medical condition, disease, or disorder or a specific dosage or a specific patient, as disclosed herein. For example, a pharmacist or assistant thereof can program, such as over a wired or wireless connection, the logic via a pharmacy electronic terminal, which can include an electronic payment device, such as a payment card reader, a mobile phone wallet reader, a currency input device, a bill acceptor, a cash register, or others, or via a point-of-sale (POS) system, which may include some, most, or all of the foregoing, and can be positioned in a customer interaction area or a back pharmacy or restricted personnel area, or others. Such programming can include input or modification of (1) patient identification information, such as personal information, biometrics (e.g., fingerprint, retina scan), or others, (2) medical condition, disease, or disorder type, (3) prevention, diagnosis, monitoring, amelioration, or treatment information, such as medical device operation parameters, such as dosages, timing, or others. For example, the logic can be executed via the processor 104D, such as to authenticate users, to use or to track use of the medical device 108D for at least one of prevention, diagnosis, monitoring, amelioration, or treatment, to modify prescription data, to switch the medical device 108D between a plurality of modes, to communicate with other devices, accessories, peripherals, to reconfigure, retrofit, or update the medical device 108, or others.

In certain embodiments, the memory 106 is included within the storage medium 112. In these embodiments, storage medium 112 also stores a content, such as an activation code, a set of prescription data, a set of dosage/frequency of use data, or others. For example, the content can include a content that includes a specified number of doses that may be used by the medical device, or a specific period of time in which the medical device may be used, or a combination of these doses and time, as described in detail below.

In certain embodiments, the storage medium 112 may include a second content (e.g., barcode, text, image, sound) that is unique with respect to a particular medical device 108D and/or other similar medical devices 108D, such as a serial number, a device identifier, a device parameter, or others, or a plurality of medical devices listed in a database, as disclosed herein. The second content can be stored internal or external to the logic stored in the memory 106. The second content can be of any type, such as an alphanumeric, an image, a barcode, a sound, a data structure, a projection, a depression, a hole, or any others. The second content can be formatted in any manner, such as binary, denary, hexadecimal, or others.

The reader 110D is configured to read the content(s) from storage medium 112. The reader 110D can include one or more sensors, such as, for example, biosensors, feedback sensors, chemical sensors, optical sensors, acoustic sensors, vibration sensors, motion sensors, fluid sensors, radiation sensors, temperature sensors, motion sensors, proximity sensors, fluid sensors, or others. The one sensor can be used to sense and detect various properties, conditions and/or characteristics or variations to same or lack thereof. The sensor may generate an output, such as one or more outputs, which are communicated, via wire, wirelessly or waveguide, to the medical device 108D, a base station, processor, server, or other logic or computing device. The output may be used as an input to one or more of the foregoing devices to forecast or avert an imminent onset or predicted upcoming onset of a symptom, episode, condition or disease. For example, as disclosed in U.S. Patent App. Pub. No. 2017/0120052, which is incorporated herein by reference in its entirety for at least these purposes as if copied and pasted herein, as disclosed herein, and for all purposes as if copied and pasted herein, such as all structures, all functions, and all methods of manufacture and use, as disclosed therein.

The medical device 108D can be of any type to at least one of prevent, diagnose, monitor, ameliorate, or treat a medical condition, a disease, or a disorder of a patient, such as a mammal, such as a human, whether infant, child, adult, or elderly, or others.

For example, the medical device 108 can be configured to prevent, diagnose, monitor, ameliorate, or treat any or the conditions, diseases or disorders listed previously. For example, the medical device 108 can be configured to prevent, diagnose, monitor, ameliorate, or treat a neurological condition, such as epilepsy, headache/migraine, whether primary or secondary, whether cluster or tension, neuralgia, seizures, vertigo, dizziness, concussion, aneurysm, palsy, Parkinson's disease, Alzheimer's disease, or others, as understood to skilled artisans and which are only omitted here for brevity.

For example, the medical device 108 can be configured to prevent, diagnose, monitor, ameliorate, or treat neurological, neuropsychological, or neuropsychiatric activity, such as a modulation of neuronal function or processing to affect a functional outcome. The modulation of neuronal function can be useful with regard to diagnose, monitor, prevent, treat, or ameliorate of neurological, psychiatric, psychological, conscious state, behavioral, mood, or thought activity. For example, this activity can manifests itself in a form of a disorder, such as attention or cognitive disorders (e.g., Autistic Spectrum Disorders), mood disorder (e.g., major depressive disorder, bipolar disorder, dysthymic disorder), anxiety disorder (e.g., panic disorder, posttraumatic stress disorder, obsessive-compulsive disorder, phobic disorder); neurodegenerative diseases (e.g., multiple sclerosis, Alzheimer's disease, amyotrophic lateral sclerosis (ALS), Parkinson's disease, Huntington's Disease, Guillain-Barre syndrome, myasthenia gravis, and chronic idiopathic demyelinating disease (CID)), movement disorders (e.g., dyskinesia, tremor, dystonia, chorea and ballism, tic syndromes, Tourette's Syndrome, myoclonus, drug-induced movement disorders, Wilson's Disease, Paroxysmal Dyskinesias, Stiff Man Syndrome and Akinetic-Ridgid Syndromes and Parkinsonism), epilepsy, tinnitus, pain, phantom pain, diabetes neuropathy, enhancing or diminishing any neurological or psychiatric function not just an abnormality or disorder or others, as understood to skilled artisans and which are only omitted here for brevity. Neurological activity that may be modulated can include normal functions, such as alertness, conscious state, drive, fear, anger, anxiety, repetitive behavior, impulses, urges, obsessions, euphoria, sadness, and the fight or flight response, as well as instability, vertigo, dizziness, fatigue, photophobia, concentration dysfunction, memory disorders, headache, dizziness, irritability, fatigue, visual disturbances, sensitivity to noise (misophonia, hyperacusis, phonophobia), judgment problems, depression, symptoms of traumatic brain injury (whether physical, emotional, social, or chemical), autonomic functions, which includes sympathetic or parasympathetic functions (e.g., control of heart rate), somatic functions, or enteric functions.

For example, the medical device 108 can be configured to prevent, diagnose, monitor, ameliorate, or treat a neurodegenerative disease, such as Alzheimer's disease, Parkinson's disease, multiple sclerosis, postoperative cognitive dysfunction, and postoperative delirium, or others, as understood to skilled artisans and which are only omitted here for brevity.

For example, the medical device 108 can be configured to prevent, diagnose, monitor, ameliorate, or treat an inflammatory disorder, such as Alzheimer's disease, ankylosing spondylitis, arthritis (osteoarthritis, rheumatoid arthritis (RA), psoriatic arthritis), asthma, atherosclerosis, Crohn's disease, colitis, dermatitis, diverticulitis, fibromyalgia, hepatitis, irritable bowel syndrome (IBS), systemic lupus erythematous (SLE), nephritis, Parkinson's disease, ulcerative colitis, chronic peptic ulcer, tuberculosis, periodontitis, sinusitis, hepatitis, or others, as understood to skilled artisans and which are only omitted here for brevity.

For example, the medical device 108 can be configured to prevent, diagnose, monitor, ameliorate, or treat a gastrointestinal condition, such as ileus, irritable bowel syndrome, Crohn's disease, ulcerative colitis, diverticulitis, gastroesophageal reflux disease, or others, as understood to skilled artisans and which are only omitted here for brevity.

For example, the medical device 108 can be configured to prevent, diagnose, monitor, ameliorate, or treat a bronchial disorder, such as asthma, bronchitis, pneumonia, or others, as understood to skilled artisans and which are only omitted here for brevity.

For example, the medical device 108 can be configured to prevent, diagnose, monitor, ameliorate, or treat a coronary artery disease, heart attack, arrhythmia, cardiomyopathy, or others, as understood to skilled artisans and which are only omitted here for brevity.

For example, the medical device 108 can be configured to prevent, diagnose, monitor, ameliorate, or treat a urinary disorder, such as urinary incontinence, urinalysis, overactive bladder, or others, as understood to skilled artisans and which are only omitted here for brevity.

For example, the medical device 108 can be configured to prevent, diagnose, monitor, ameliorate, or treat a cancer, such as bladder cancer, breast cancer, prostate cancer, lung cancer, colon or rectal cancer, skin cancer, thyroid cancer, brain cancer, leukemia, liver cancer, lymphoma, pancreatic cancer, or others, as understood to skilled artisans and which are only omitted here for brevity.

For example, the medical device 108 can be configured to prevent, diagnose, monitor, ameliorate, or treat a metabolic disorder, such as diabetes (type 1, type 2, or gestational), Gaucher's disease, sick cell anemia, cystic fibrosis, hemochromatosis, or others, as understood to skilled artisans and which are only omitted here for brevity.

The medical device 108 can be configured to output an energy via an energy source of the medical device 108, such as a mechanical energy via an actuation source (e.g., actuator) of the medical device 108, an electrical energy via a current or voltage source (e.g., electrode) of the medical device 108, an electromagnetic energy via an impulse source (e.g., generator) of the medical device 108, a thermal energy via a heating (e.g., heating element) or cooling (e.g., ice pack, fan) source of the medical device 108, an acoustic energy via an acoustic source (e.g., speaker, transducer) of the medical device 108, or a light energy via a light source (e.g., bulb, laser beam generator) of the medical device 108. For example, as shown in FIG. 1B, the medical device 108 can include a neurostimulator 108B, whether invasive, non-invasive, or hybrid. For example, the neurostimulator 108B can be embodied as described in US Patent Application Publication 2014/0330336 and U.S. Pat. Nos. 8,874,205, 9,037,247, 9,174,066, 9,205,258, 9,375,571, and 9,427,581, all of which are herein incorporated by reference for all purposes as if copied and pasted herein, such as all structures, all functions, and all methods of manufacture and use, as disclosed therein. For example, the neurostimulator can modulate central or peripheral nervous systems. For example, the neurostimulator can be enable spinal cord stimulation to provide therapy for intractable pain and refractory angina; occipital nerve stimulation to provide therapy for occipital neuralgia and transformed migraine; afferent vagus nerve modulation to provide therapy for a host of neurological and neuropsychiatric disorders, such as epilepsy, depression, Parkinson's disease, bulemia, anxiety/obsessive compulsive disorders, Alzheimer's disease, autism, and neurogenic pain; efferent vagus nerve stimulation for rate control in atrial fibrillation, and to provide therapy for congestive heart failure; gastric nerves or gastric wall stimulation to provide therapy for obesity; sacral nerve stimulation to provide therapy for urinary urge incontinence; deep brain stimulation to provide therapy for Parkinson's disease, and other neurological and neuropsychiatric disorders; cavernous nerve stimulation to provide therapy for erectile dysfunction. However, as explained herein, note that the medical device 108 can be of any type or modality for at least one of prevention, diagnosis, monitoring, amelioration, or treatment of a medical condition, disease, or a disorder of a patient. For example, the medical device 108 can be configured to output a fluid, such as a liquid, a suspension, or a gas. For example, the medical device 108 can be configured to output a gel, a powder, or a foam. For example, the medical device 108 can be configured to increase or decrease pressure or provide physical support, whether internal or external to a patient. An example of a device that can be used is a mechanical actuator, vibration device, piezoelectric device, electric motor (e.g., brushed, brushless) or engine (e.g., combustion) or any other force generator, applicator, or output device.

The medical device 108 can be configured to prevent, diagnose, monitor, ameliorate, or treat a medical condition, a disease, or a disorder of a patient based on a contact with or output of an energy (e.g. mechanical, electrical, thermal, acoustic, photonic) or a fluid (e.g., liquid, gas, gel, suspension, solution) or powder to various organ systems of human body or any components thereof. These organ systems can include a muscular system, such as human skeleton, joints, ligaments, or tendons. These organ systems can include a digestive system, such as mouth, salivary glands, pharynx, esophagus, stomach, small intestine, large intestine, liver, gallbladder, mesentery, pancreas, anal canal and anus, or appendix. These organ systems can include a respiratory system, such as nasal cavity, pharynx, larynx, trachea, bronchi, lungs, or diaphragm. These organ systems can include a urinary system, such as kidneys, ureters, bladder, or urethra. These organ systems can include a reproductive system, such as female reproductive system, ovaries, fallopian tubes, uterus, vagina, vulva, clitoris, placenta, male reproductive system, testes, epididymis, vas deferens, seminal vesicles, prostate, bulbourethral glands, penis, or scrotum. These organ systems can include an endocrine system, such as pituitary gland, pineal gland, thyroid gland, parathyroid glands, adrenal glands, or pancreas. These organ systems can include a circulatory system, such as heart, patent foramen ovale, arteries, veins, or capillaries. These organ systems can include a lymphatic system, such as lymphatic vessel, lymph node, bone marrow, thymus, spleen, or gut-associated lymphoid tissue. These organ systems can include a nervous system, such as brain, brainstem, cerebellum, spinal cord, ventricular system, peripheral nervous system, nerves, sensory organs, eye, ear, olfactory epithelium, or tongue. These organ systems can include integumentary system, such as mammary glands, skin, or subcutaneous tissue.

The medical device 108 can be configured to prevent, diagnose, monitor, ameliorate, or treat a medical condition, a disease, or a disorder of a patient based on a contact with or output of an energy (e.g., mechanical, electrical, thermal, acoustic, photonic) or a fluid (e.g., liquid, gas, gel, suspension, solution) or powder to various muscles of human body or any components thereof. These muscle systems include These muscle systems include forehead/eyelid, such as occipitofrontalis, occipitalis, frontalis, orbicularis oculi, corrugator supercilii, or depressor supercilii. These muscle systems include extraocular muscles, such as levator palpebrae superioris, superior tarsal, rectus muscles, or oblique muscles. These muscle systems include ear, such as auriculares, temporoparietalis, stapedius, or tensor tympani. These muscle systems include nose, such as procerus, nasalis, dilator naris, depressor septi nasi, or levator labii superioris alaeque nasi. These muscle systems include mouth, such as levator anguli oris, depressor anguli oris, levator labii superioris, depressor labii, inferioris, mentalis, buccinator, orbicularis oris, risorius, or zygomatic muscles. These muscle systems include mastication, such as masseter, temporalis, or pterygoid muscles. These muscle systems include tongue, such as genioglossus, hyoglossus, chondroglossus, styloglossus, or palatoglossus. These muscle systems include intrinsic, such as superior longitudinal, transversus, inferior longitudinal, or verticalis muscle. These muscle systems include soft palate, such as levator veli palatini, tensor veli palatini, musculus uvulae, palatoglossus, or palatopharyngeus. These muscle systems include pharynx, such as stylopharyngeus, salpingopharyngeus, or pharyngeal muscles. These muscle systems include larynx, such as cricothyroid, arytenoid, thyroarytenoid, or cricoarytenoid muscles. These muscle systems include clavicular, such as platysma, or sternocleidomastoid. These muscle systems include suprahyoid, such as digastric, stylohyoid, mylohyoid, or geniohyoid. These muscle systems include anterior, such as longus colli, longus capitis, rectus capitis anterior, or rectus capitis lateralis. These muscle systems include lateral, such as scalene muscles, levator scapulae, rectus capitis lateralis, obliquus capitis superior, or obliquus capitis inferior. These muscle systems include posterior, such as rectus capitis posterior minor, rectus capitis posterior major, semispinalis capitis, longissimus capitis, splenius capitis, obliquus capitis superior, or obliquus capitis inferior. These muscle systems include back, such as erector spinae, latissimus dorsi, transversospinales, interspinales, intertransversarii, or splenius muscles. These muscle systems include chest, such as intercostals, subcostales, transversus thoracis, levatores costarum, serratus posterior muscles, diaphragm. These muscle systems include abdomen, such as transversus abdominis, rectus abdominis, pyramidalis, cremaster, quadratus lumborum, or oblique muscles. These muscle systems include pelvis, such as coccygeus, or levator ani. These muscle systems include perineum, such as sphincter ani, superficial perineal pouch, or deep perineal pouch. These muscle systems include vertebral column, such as trapezius, latissimus dorsi, rhomboids, or levator scapulae. These muscle systems include thoracic walls, such as pectoralis major, pectoralis minor, subclavius, or serratus anterior. These muscle systems include shoulder, such as deltoid, teres major, rotator cuff, supraspinatus, infraspinatus, teres minor, or subscapularis. These muscle systems include arm anterior compartment, such as coracobrachialis, biceps brachii, or brachialis. These muscle systems include arm posterior compartment, such as triceps brachii, or anconeus. These muscle systems include forearm anterior compartment, such as pronator teres, flexor carpi radialis, palmaris longus, flexor carpi ulnaris, flexor digitorum superficialis, pronator quadratus, flexor digitorum profundus, or flexor pollicis longus. These muscle systems include forearm posterior compartment, such as extensor digitorum, extensor digiti minimi, extensor carpi ulnaris, mobile wad, supinator, extensor indicis, anatomical snuff box, or extensor pollicis brevis. These muscle systems include hand such as opponens pollicis, flexor pollicis brevis, abductor pollicis brevis, adductor pollicis, palmaris brevis, hypothenar, lumbrical, dorsal interossei, or palmar interossei. These muscle systems include lower limb, such as iliopsoas, tensor fasciae latae, gluteal muscles, lateral rotator group, superior gemellus, articularis genus, sartorius, quadriceps femoris, biceps femoris, semitendinosus, semimembranosus, or adductor muscles of the hip. These muscle systems include leg, such as tibialis anterior, extensor hallucis longus, extensor digitorum longus, fibularis tertius, triceps surae, popliteus, tarsal tunnel, longus, or brevis. These muscle systems include foot, such as extensor digitorum brevis, extensor hallucis brevis, abductor hallucis, flexor digitorum brevis, abductor digiti minimi, quadratus plantae, lumbrical muscle, flexor hallucis brevis, adductor hallucis, flexor digiti minimi brevis, dorsal interossei, or plantar interossei.

The medical device 108 can be configured to prevent, diagnose, monitor, ameliorate, or treat a medical condition, a disease, or a disorder of a patient based on a contact with or output of an energy (e.g. mechanical, electrical, thermal, acoustic, photonic) or a fluid (e.g. liquid, gas, gel, suspension, solution) or powder to various nerves of human body or any components thereof. These nerves include nerves, such as abdominal aortic plexus, abducens nerve, accessory nerve, accessory obturator nerve, alderman's nerve, anococcygeal nerve, ansa cervicalis, anterior interosseous nerve, anterior superior alveolar nerve, auerbach's plexus, auriculotemporal nerve, axillary nerve, brachial plexus, buccal branch of the facial nerve, buccal nerve, cardiac plexus, cavernous nerves, cavernous plexus, celiac ganglia, cervical branch of the facial nerve, cervical plexus, chorda tympani, ciliary ganglion, coccygeal nerve, cochlear nerve, common fibular nerve, common palmar digital nerves of median nerve, deep branch of the radial nerve, deep fibular nerve, deep petrosal nerve, deep temporal nerves, diagonal band of broca, digastric branch of facial nerve, dorsal branch of ulnar nerve, dorsal nerve of clitoris, dorsal nerve of the penis, dorsal scapular nerve, esophageal plexus, ethmoidal nerves, external laryngeal nerve, external nasal nerve, facial nerve, femoral nerve, frontal nerve, gastric plexuses, geniculate ganglion, genital branch of genitofemoral nerve, genitofemoral nerve, glossopharyngeal nerve, greater auricular nerve, greater occipital nerve, greater petrosal nerve, hepatic plexus, hypoglossal nerve, iliohypogastric nerve, ilioinguinal nerve, inferior alveolar nerve, inferior anal nerves, inferior cardiac nerve, inferior cervical ganglion, inferior gluteal nerve, inferior hypogastric plexus, inferior mesenteric plexus, inferior palpebral nerve, infraorbital nerve, infraorbital plexus, infratrochlear nerve, intercostal nerves, intercostobrachial nerve, intermediate cutaneous nerve, internal carotid plexus, internal laryngeal nerve, interneuron, jugular ganglion, lacrimal nerve, lateral cord, lateral cutaneous nerve of forearm, lateral cutaneous nerve of thigh, lateral pectoral nerve, lateral plantar nerve, lateral pterygoid nerve, lesser occipital nerve, lingual nerve, long ciliary nerves, long root of the ciliary ganglion, long thoracic nerve, lower subscapular nerve, lumbar nerves, lumbar plexus, lumbar splanchnic nerves, lumboinguinal nerve, lumbosacral plexus, lumbosacral trunk, mandibular nerve, marginal mandibular branch of facial nerve, masseteric nerve, maxillary nerve, medial cord, medial cutaneous nerve of arm, medial cutaneous nerve of forearm, medial cutaneous nerve, medial pectoral nerve, medial plantar nerve, medial pterygoid nerve, median nerve, meissner's plexus, mental nerve, middle cardiac nerve, middle cervical ganglion, middle meningeal nerve, motor nerve, muscular branches of the radial nerve, musculocutaneous nerve, mylohyoid nerve, nasociliary nerve, nasopalatine nerve, nerve of pterygoid canal, nerve to obturator internus, nerve to quadratus femoris, nerve to the piriformis, nerve to the stapedius, nerve to the subclavius, nervus intermedius, nervus spinosus, nodose ganglion, obturator nerve, oculomotor nerve, olfactory nerve, ophthalmic nerve, optic nerve, otic ganglion, ovarian plexus, palatine nerves, palmar branch of the median nerve, palmar branch of ulnar nerve, pancreatic plexus, patellar plexus, pelvic splanchnic nerves, perforating cutaneous nerve, perineal branches of posterior femoral cutaneous nerve, perineal nerve, petrous ganglion, pharyngeal branch of vagus nerve, pharyngeal branches of glossopharyngeal nerve, pharyngeal nerve, pharyngeal plexus, phrenic nerve, phrenic plexus, posterior auricular nerve, posterior branch of spinal nerve, posterior cord, posterior cutaneous nerve of arm, posterior cutaneous nerve of forearm, posterior cutaneous nerve of thigh, posterior scrotal nerves, posterior superior alveolar nerve, proper palmar digital nerves of median nerve, prostatic plexus (nervous), pterygopalatine ganglion, pudendal nerve, pudendal plexus, pulmonary branches of vagus nerve, radial nerve, recurrent laryngeal nerve, renal plexus, sacral plexus, sacral splanchnic nerves, saphenous nerve, sciatic nerve, semilunar ganglion, sensory nerve, short ciliary nerves, sphenopalatine nerves, splenic plexus, stylohyoid branch of facial nerve, subcostal nerve, submandibular ganglion, suboccipital nerve, superficial branch of the radial nerve, superficial fibular nerve, superior cardiac nerve, superior cervical ganglion, superior ganglion of glossopharyngeal nerve, superior ganglion of vagus nerve, superior gluteal nerve, superior hypogastric plexus, superior labial nerve, superior laryngeal nerve, superior lateral cutaneous nerve of arm, superior mesenteric plexus, superior rectal plexus, supraclavicular nerves, supraorbital nerve, suprarenal plexus, suprascapular nerve, supratrochlear nerve, sural nerve, sympathetic trunk, temporal branches of the facial nerve, third occipital nerve, thoracic aortic plexus, thoracic splanchnic nerves, thoracoabdominal nerves, thoracodorsal nerve, tibial nerve, transverse cervical nerve, trigeminal nerve, trochlear nerve, tympanic nerve, ulnar nerve, upper subscapular nerve, uterovaginal plexus, vagus nerve, ventral ramus, vesical nervous plexus, vestibular nerve, vestibulocochlear nerve, zygomatic branches of facial nerve, zygomatic nerve, zygomaticofacial nerve, or zygomaticotemporal nerve.

The medical device 108 can be configured to prevent, diagnose, monitor, ameliorate, or treat a medical condition, a disease, or a disorder of a patient based on a contact with or output of an energy (e.g. mechanical, electrical, thermal, acoustic, photonic) or a fluid (e.g. liquid, gas, gel, suspension, solution) or powder to various bones of human body or any components thereof. These bones include spine, such as cervical vertebrae, thoracic vertebrae, lumbar vertebrae, sacral vertebrae, or coccygeal vertebrae. These bones include chest, such as hyoid, sternum, or ribs. These bones include head, such as cranial bones, facial bones, hyoid bones, or middle ear. These bones include arm, such as humerus, pectoral girdle, hand, metacarpals, or phalanges of the hand. These bones include pelvis, such as hip bone, ilium, ischium, pubis, sacrum, or coccyx. These bones include leg, such as femur, patella, tibia, fibula, or foot The medical device 108D has at least a first mode and a second mode. As such, since the processor 104D is coupled (e.g. electrically, mechanically) to the medical device 108D, the processor 104D is able to execute (e.g. serial, parallel) the logic stored on a memory in the medical device 108D or a separate memory 106 and thereby switch the medical device 108D between the first mode and the second mode based on an input, such as a trigger, a heuristic, an action, or others, and operate the medical device 108D in the first mode or the second mode based on a set of parameters, which may be accessible to or stored in or via the medical device 108D, processor 104D and/or the storage medium 112. For example, the first mode can be an off mode and the second mode can be an on mode or vice versa. Similarly, the first mode can be a deactivated mode and the second mode can be an activated mode or vice versa. However, note that (1) the medical device 108D can be in the on mode, yet still be in the deactivated mode, and (2) the medical device 108D can at least one of prevent, diagnose, monitor, ameliorate, or treat the medical condition, disease, or the disorder of the patient in the activated mode. However, note again that, within the activated mode, the medical device 108D may have a plurality of sub-modes as well, such as modes of prevention, diagnosis, monitoring, amelioration, or treatment of various types, intensities, dosages, or others, which can vary based on medical conditions, disorders, diseases, or conditions. For example, the medical device 108D can operate in a first manner during the first mode and in a second manner in the second mode, where the first manner is different from or identical to the second manner, such as in an amount of operation, in an intensity of operation, in a duration of operation, in a modality of operation, in an energy use of operation, or others. For example, when the processor 104D switches the medical device 108D from the first mode (e.g., a deactivated mode) to the second mode (e.g., an activate mode), then such switching can activate the medical device 108 for a specific time period or a number of diagnosis or treatment doses or other parameters or vice versa. For example, the amount of operation includes a number of individual doses of at least one of diagnosis or treatment doses, such as less than or more than 3 doses, 4 doses, 5 doses, 6 doses, 7 doses, 8 doses, 9 doses, 10 doses, 15 doses, 20 doses, 25 doses, 30 doses, 40 doses, 45 doses, 50 doses, 60 doses, 65 doses, 70 doses, 75 doses, 80 doses, 85 doses, 90 doses, 95 doses, 100 doses, 200 doses, 300 doses, 400 doses, 500 doses, 600 doses, 700 doses, 800 doses, 900 doses, 1000 doses, 10,000 doses or any other amount of doses from 1 to 10,000 or greater, or others, whether a dose is based on a single use or a set of uses within a predefined time period (e.g., milliseconds, seconds, minutes, hours, days, weeks, months, years). For example, the amount of operation may include a total number of doses over a total period of time. Alternatively, the amount of operation may include an unlimited number of doses for a period of time, and/or the number of doses may be limited within subsets of the period of time. For example, the number of doses may be limited to 2-10 doses per day, but otherwise unlimited for a total number of days, months or years.

As such, the medical device 108D can be adjusted where the first mode and the second mode can be equal or unequal in the amount of doses. Similarly, the intensity of operation includes a degree or type of intensity with which the medical device 108D at least one of prevents, diagnoses, monitors, ameliorates, or treats the medical condition, disease, or the disorder in the patient. For example, the first mode can be associated with a first prevention, diagnosis, monitoring, amelioration, or treatment signal/energy output and the second mode can be associated with a second prevention, diagnosis, monitoring, amelioration, or treatment signal/energy output, wherein the first signal/energy output is identical to or differs from the second signal/energy output in various parameters, such as a content, a format, an amplitude, a frequency, a time period, or others. As such, the medical device 108D can be adjusted to more intensely or less intensely prevent, diagnose, monitor, ameliorate, or treat based on switching between the first mode and the second mode. Likewise, the duration of operation includes a number of defined time periods during which the medical device can at least one of prevent, diagnose, monitor, ameliorate, or treat, such as a number of seconds, minutes, hours, days, weeks, months, or others, whether dependent on usage or independent of usage. As such, the medical device 108D can be adjusted to a least one of prevent, diagnose, monitor, ameliorate, or treat between a first defined time period and a second defined time period.

The reader 110D (or the input device 110) is configured to obtain, such as via reading, copying, or others, the content from the storage medium 112, such as a magnetic card, a radio frequency identification (RFID) card, a chip card, a barcode, a Quick Response (QR) code, or others, such that the processor 104 switches the medical device 108D between the first mode and the second mode based on the first content corresponding to the second content, such as logically or others, or vice versa. The first content may also include a second content, such as an activation code, a set of prescription data, a set of dosage/frequency of use data, or others, can be associated with the medical device 108D, such as uniquely or others, with a specific mode of operation, such as for preventing, diagnosing, monitoring, ameliorating, or treating a specific medical condition, disease, or disorder, or with a particular user, such as based on a user identifier, such as a personal identification number (PIN), a biometric, or others.

Note that the particular user can be associated with the medical device 108D, such as via a primary key of a relational database, as disclosed herein. For example, the primary key can be the PIN or another set of data such that the second content is unique to the particular user. In some embodiments, where the medical device 108 is shared among a plurality of users, the second content can be unique to one of the users, yet access control or authentication between the users can be controlled via another layer or form of identification, such as passwords, biometrics, or others, such as when the system 100D includes a user input device coupled to the processor 104D. For example, the user input device can include a keyboard or dial, whether physical, virtual (e.g., display), or haptic (e.g., display), a biometric reader, a fob or tag, a barcode, or others.

The second content can be of any of type, whether identical to or different from the first content, such as an alphanumeric, an image, a barcode, a sound, a data structure, a projection, a depression, a hole, or any others. The second content can be formatted in any manner, whether identical to or different from the first content, such as binary, denary, hexadecimal, or others.

The reader 110D or input device 110 can be of any modality or type, such as a camera, a microphone, a sensor, a card reader, a signal receiver, or others. For example, as shown in FIG. 12D, the housing 102D includes a reader 110D, such as a reader terminal, that is configured to read the content from the storage medium 112, such as a card, a display, an interface, a chip, a memory dongle, a paper, or others, whether the storage medium is in or out of a line-of-sight of the reader 110D. For example, when the storage medium is a card, which can include paper, cardboard, plastic, rubber, metal, wood, or others, and the reader 110D is a card reader, then the card can be embedded with at least one of a barcode, a magnetic strip, a computer chip, or another storage medium and the card reader can read the at least one of the barcode, the magnetic strip, the computer chip, or the another storage medium. For example, the memory dongle can include a Universal Serial Bus (USB) dongle, a CompactFlash (CF) card, Secure Digital (SD) card, a MultiMediaCard (MMC) card. Therefore, the card can be a dumb card, a smart card, a memory card, a Wiegand card, a proximity card, or others, whether contact or contactless. Correspondingly, the reader 110D can be a smart card reader, a memory card reader, a Wiegand card reader, a magnetic stripe reader, a proximity reader, or others, whether the reader 110D is a non-intelligent reader, a semi-intelligent reader, or an intelligent reader. The input device 110 or reader 110D can be distinct from the medical device 108 or be a component of the medical device 108D. The memory 106 can include the storage medium (e.g., removable memory chip) or vice versa. The memory 106 can exclude the storage medium or vice versa.

In certain embodiments, as shown in FIG. 12C, the input device 110 includes a transceiver 110C, which includes a receiver, that is configured to receive, whether over a wired, wireless, or waveguide connection, the content from the storage medium, such a card, a phone, a tablet, a laptop, a wearable, or others, such via a radio technique, an optical technique, an acoustic technique, or others, whether the storage medium is in or out of a line-of-sight of the transceiver 110C. For example, the radio technique can include a RFID interrogation, a Wi-Fi communication, a Bluetooth communication, or other radio communication formats, which can be encrypted or unencrypted. For example, the optical technique can include a laser beam, an infrared beam, a Li-Fi connection, or others. Note that the transceiver can include a transmitter or a receiver.

The input device 110 can obtain the content from the storage medium in various ways. For example, the input device 110 can obtain the content electronically, optically, electromagnetically, mechanically, or others, whether the storage medium is in or out of a line-of-sight of the input device 110. For example, when the input device 110 is the reader 110B, as per FIG. 1B, then the input device 110 can read the content from the storage medium based on at least one of a barcode of the storage medium (optically), a QR code of the storage medium (optically), a magnetic material of the storage medium (electromagnetically), a chip of the storage medium (electromagnetically), an integrated circuit of the storage medium (electronically), a non-volatile memory of the storage medium (electronically), a punched hole of the storage medium (mechanically), a tactile surface of the storage medium (mechanically), or others. Likewise, when the input device 110 is the transceiver 110C, then the input device 110 can read the content from the storage medium via an RFID technique, such as via interrogation, whether the storage medium is passive or active. Note that in some embodiments, the input device 110 includes the reader 110B and the transceiver 110C.

The first content can correspond to the second content in various ways, such as logically, such as via a Boolean logic, or others. For example, the first content can match the second content in content, format, logic, parameters, encryption, or others. For example, the first content can be equal to the second content, whether in format or value. Similarly, the first content can be unequal to the second content, whether in format or value. Likewise, the first content can logically map to the second content, such as via a logical symmetry where the first content is same as the second content or where the first content is different from the second, but related in a relatively quick computational way. For example, such correspondence can be determined based on or via hashing the first content or the second content. In some embodiments, processor 104 or the input device 110 can convert the first content or the second content before determining whether the first content corresponds to the second content. For example, such conversion can involve a format or a content of the first content or the second content.

In certain embodiments, when the first content does not correspond to the second content, such as the first content does not match the second content in value and format or others, as described above, then the medical device 108 is not switched from the first mode, such as a deactivated mode, to the second mode, such as an activated mode. In some embodiments, when the first content does not correspond to the second content, then the medical device 108 is switched from the first mode to the second mode, but the second mode is as or less operational than the first mode. For example, the second mode is a default mode of operation, a minimal mode of operation, a demo mode of operation, a disabled mode of operation, a kiosk mode of operation, or others.

In other embodiments (as shown in FIG. 12D), the storage medium 112 only includes the first content, which does not have to match up with a second content. In these embodiments, the reader 110D reads the first content from the storage medium 112 and the processor 104D switches the medical device 108D from the deactivated mode to the activated mode. The processor 104D will maintain the medical device 108D in the active mode based on the first content (i.e., how many doses and/or how much time existed in the first content).

In these embodiments, the first content in the storage medium 112 may be configured to be erased, or scrambled, after the reader 110D has read the first content from the storage medium. The first content may be actively erased or scrambled by the processor 104D or reader 110D after the information from the first content has been stored in the processor and/or the medical device 108. Alternatively, the storage medium 112 may be configured to erase or scramble itself once the first content has been read and transferred to the processor 104D. In either event, the storage medium 112 is no longer usable to activate the medical device after the first content has been read and transferred to the processor 104D.

In certain embodiments, the storage medium 112 may include a first content that represents one or more doses of the therapy and a second content that represents a larger number of doses, a time period with unlimited doses or a time period with a limited number of doses for the entire time period, or a time period with limited number of doses within sub-time periods (i.e., limited number of doses/day for a period of days, months or years). In these embodiments, the reader 110D is configured to read the first content and, via the processor 104D, switch the medical device 108D from the first mode to the second mode. The medical device 108D will then be capable of being activated or used for the number of doses in the first content.

In certain embodiments, the reader 110D may be capable of reading the first content without reading the second content. In these embodiments, the first content will be erased or scrambled after it has been read by the reader and the first content transferred to the medical device 108D by the processor 104D. Alternatively, the processor 104D and/or the medical device 108D may save an identification of the storage medium 112, such as a UID, such that the first content cannot be used again by the same or another medical device 108D. The second content may not be erased or scrambled when the first content is read by the reader 110D. If the second content includes a time period, the first content does not start the internal clock of the medical device for the time period. In this configuration, the storage medium may be configured such that the user can operate the medical device one or more times without erasing the dosing information in the second content from the storage medium. For example, a physician or caregiver may activate the medical device 108D for one or more sample doses to provide instruction or a demonstration of the proper use of the medical device 108D to the patient. These sample or demo doses can be provided without reading the second content, which contains the actual prescribed dose for the patient.

One particular advantage of this embodiment occurs if the second content provides a time period in which the medical device 110D will be activated. Reading the first content from the storage medium 112 does not necessarily start the time period for the second content (i.e., the internal clock of the medical device 110D). Thus, a physician or caregiver may read the first content, provide one or more sample/demo doses and then allow the patient to read the second content (thereby starting the clock on the time period at a later time or date when the prescription of doses is designed to begin).

Alternatively, the reader 110D may be configured to read both the first content and the second content of the storage medium 112 simultaneously such that both contents are transferred to the medical device 108D via the processor 104D. In this embodiment, the medical device 108D or the processor 104D may be configured to erase or scramble both the first content and the second content after they have been transferred to the medical device 108D. The medical device 108D will then be activated for the number of doses and/or time in both the first content and the second content.

Figure 20A:
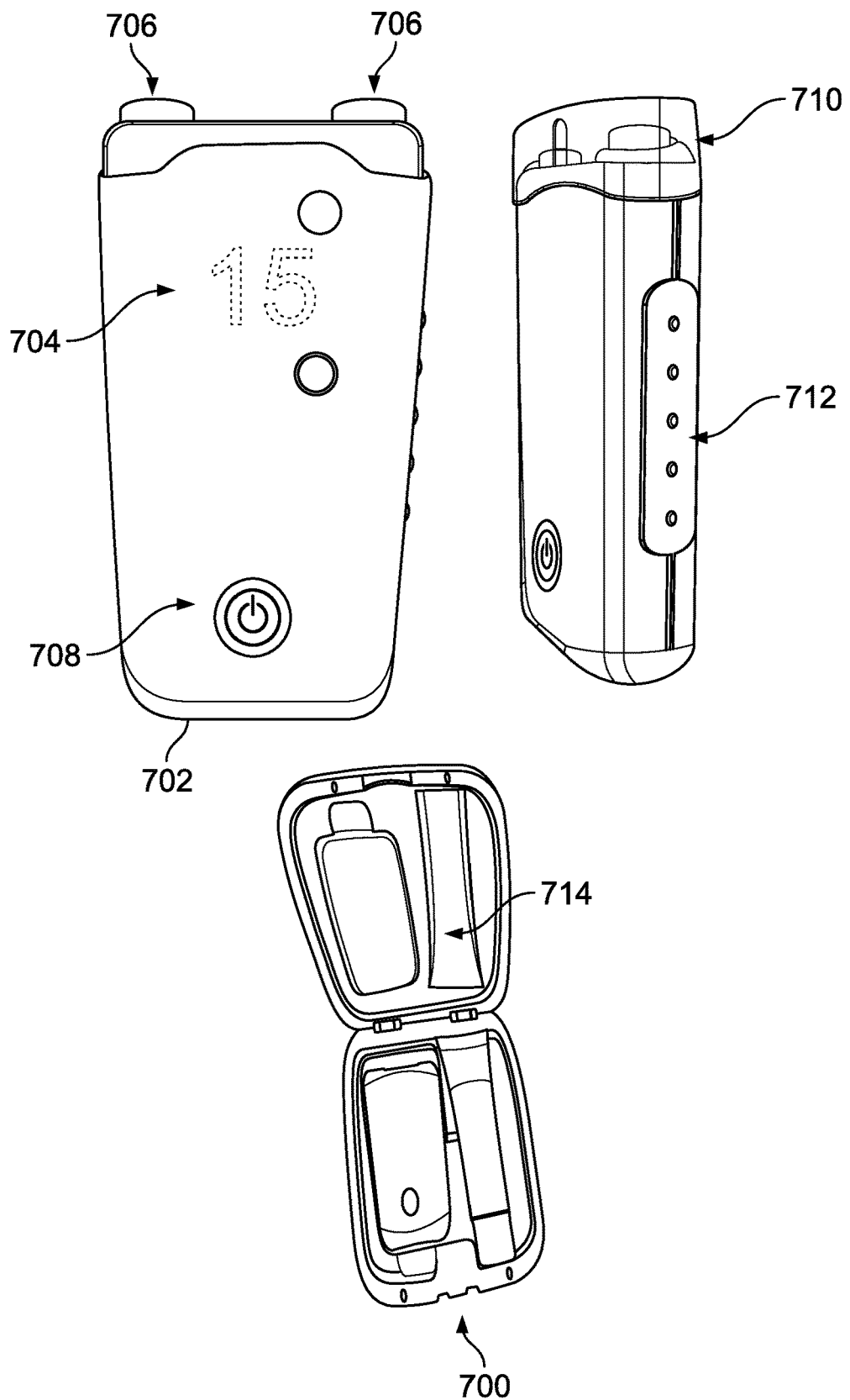

In some embodiments, system 100D will include a user display and input controls on the medical device 108D. The user display may be, for example, disposed on the medical device 108D or on a separate visual display that is coupled to the medical device. FIG. 20A illustrates one example of a visual display 704 that may be included within the medical device 108D. The input controls may include any number of suitable user inputs such as buttons, knobs, levers, rotatable wheels or discs, switches, text fields, seek bars, checkboxes, radio buttons, toggles, spinners or the like. In certain embodiments, the user display may include a time display and the input controls may include buttons that allow the user to change the time, for example, set the medical device 108D to local time or another time. In this embodiment, the user may set the time on the medical device 108D to correspond with a certain 24 hour time period, that may begin at midnight, 6 am, noon, or the like. Alternatively, the user may set the time to local time or another desired time zone.

In this embodiment, the processor 104D may be configured to synchronize the time set on the user display with a desired time period. Thus, if the first or second content read from the storage medium 112 includes a time period for activation of the medical device 108D, the time period will start at the desired time, i.e., midnight on the first day, the local time in which the patient receives the medical device 108D, or any other time desired by the physician, caregiver or the patient. The time period can be synchronized directly by the user through manipulation of the user inputs, or it can be read from the content on the storage medium 112.

In other embodiments, storage medium 112 may include content that causes the processor 104D and/or the medical device 108D to display certain data or information on the user display. For example, storage medium 112 may include a set of instructions and/or data that, when transferred to the processor 104D, causes the processor 104D to display certain information on the user display, such as unique device identification (e.g., Bluetooth address information) for the individual medical device 108D. This information may be useful for immediately providing the device identification for connecting to the medical device 108D via Bluetooth or other wireless communication during testing or manufacturing of the device.

Alternatively, the reader 110D and/or processor 104D may be configured to transfer data or information from the medical device 108D to the storage medium 112. For example, the reader 110D may be configured to recognize a storage medium 112 and, when that storage medium 112 is placed near or within a suitable distance from, the reader 110D, the reader 110D transfers information to the storage medium 112. In this embodiment, the storage medium 112 will have content and a memory that can be read and written over to transfer information or data to the storage medium 112. Storage medium 112 may also have a visual display for viewing certain content within its memory. The memory within storage medium 112, whether volatile or non-volatile, is at least one of a mechanical memory, such as a punch card or others, or a semiconductor memory, such as a flash memory or others. The memory can receive, such as via a physical recordation, a wired or wireless connection, or others, and store a logic, such as projections, depressions, holes, modules, objects, programs, apps, firmware, microcode, or other forms of instruction, for execution.

In one exemplary example, the reader 110B is configured to transfer unique device identification (e.g., Bluetooth address information) for the individual medical device 108D to the memory of storage medium 112. The unique device identification may be displayed on the visual display of storage medium 112. This information may be useful for immediately providing the device identification for connecting to the medical device 108D via Bluetooth or other wireless communication during testing or manufacturing of the device.

In some embodiments, the content on storage medium 112 may include a set of instructions, algorithms, or programs for a software application or program. The software application may reside on processor 104D, medical device 108D or a separate component of system 100D. In these embodiments, reader 110D will read the set of instructions and transfer them to the software program. The set of instructions may include, for example, instructions to display certain information or data on the user display of the medical device 108D or another visual display or instructions to transfer data within processor 104D or medical device 108D to another processor or visual display (e.g., computer, mobile phone, downloadable computer application or the like). The storage medium 112 may include the set of instructions in addition to any of the content described above, or the set of instructions may be the only content on the storage medium 112. In the former case, the processor 104D and/or the storage medium 112 may be configured such that the additional content (i.e., number of doses provided by the storage medium 112) is not erased or scrambled when the set of instructions is read from the storage medium 112. The storage medium 112 may be configured such that the set of instructions can be read multiple times with the same storage medium (e.g., during visits to the physician).

In one such embodiment, storage medium 112 includes a set of instructions to display data on the user display of the medical device 108D or another visual display coupled to the processor 104D. The data may include, for example, the total number of doses administered by the medical device 108D, the total number of doses administered during a particular time period (e.g., last 30 days, last 60 days, 90 days, year to date, month to date, etc.), the average number of uses over a particular time period, the amount of time for each dose, the actual time each dose is administered, the parameters of each dose, such as voltage, current, device settings (e.g., 1-9) and the like. This allows either the patient or the caregiver to monitor use of the device to determine if the patient has complied with the therapy prescribed by the caregiver.

In some embodiments, system 100 includes a software application that can be downloaded into the processor 104D, the medical device 108D or a separate device, such as a computer, mobile phone, tablet or the like. Alternatively, the software application is not downloaded from outside the processor 104D, medical device 108D or separate device, but is instead available internally, for example, within read-only memory that is present within the device. In this example, medical device 108D may be integrated with, or coupled to, a mobile device, such as a mobile phone. A more complete description of a suitable system for coupling a medical device 108D to a mobile device can be found in commonly-assigned U.S. Pat. No. 9,375,571, the complete disclosure of which is incorporated herein by reference for all purposes as if copied and pasted herein.

In some embodiments, storage medium 112 may include a set of instructions for transferring or downloading information or data within processor 104D or medical device 108D to the software application and/or to another device, such as a server, the internet (e.g., the cloud), a computer, mobile phone or the like. The data or information transferred may be similar to the data provided to the user display, as discussed above. The storage medium 112 may include the set of instructions in addition to any of the content described above, or the set of instructions may be the only content on the storage medium 112. In the former case, the processor 104D and/or the storage medium 112 may be configured such that the additional content (i.e., number of doses provided by the storage medium 112) is not erased or scrambled when the set of instructions is read from the storage medium 112. The storage medium 112 may be configured such that the set of instructions can be read multiple times with the same storage medium (e.g., to continuously transfer statistics from the medical device 108B to a separate software application).

In some embodiments, storage medium 112 may include data, information or a set of instructions to revise, reset and/or test certain settings, signal parameters, variables, memory, data or information, or to run system diagnostics within the medical device 108D and/or processor 104D. For example, storage medium 112 may be used in a factory setting to ensure that medical device 108D has the desired default settings, data and or variables prior to shipment to a distributor, hospital, patient or caregiver. Alternatively, the storage medium 112 may include a set of instructions to test certain parameters of the signal, such as the signal output (e.g., amplitude, voltage and/or current settings), and the like or various aspects of the hardware or software, such as the display, serial port, Bluetooth connection, and the like. This would allow the operator to test the therapy signal that is loaded into the medical device 110D as a default without having to load any other information into the device, such as dose or other therapy information. Alternatively, this embodiment can be used to instruct medical device 110B to run various self-test routines to check internal software and hardware and/or run system diagnostics during the quality assurance phase of manufacturing and/or during returns analysis.

In this embodiment, reader 110D reads and transfers a content from storage medium 112, as described above. In this case, the content may include a set of instructions for revising, resetting or testing variables, parameters or other settings in medical device. The storage medium 112 may include the set of instructions in addition to any of the content described above, or the set of instructions may be the only content on the storage medium 112. In the former case, the processor 104D and/or the storage medium 112 may be configured such that the additional content (i.e., number of doses provided by the storage medium 112) is not erased or scrambled when the set of instructions is read from the storage medium 112. The storage medium 112 may be configured such that the set of instructions can be read multiple times with the same storage medium (e.g., to use the same storage medium 112 to reset or revise default values in medical devices 110B during manufacturing or quality assurance processes).

In some embodiments, the system 100 includes an output device, such as a signal transmitter, a light, sound, or vibration source, an actuator, a data writer, or others, coupled to the processor 104, whether over a wired, wireless, or waveguide connection, where the processor 104 is configured to instruct the output device to interface with the storage medium in response to the input device 110 reading the second content. For example, the output device can include a transmitter and the processor 104 can instruct the transmitter to send a signal to the storage medium such that the storage medium can receive and process the signal, which may involve acting based on such processing. For example, such action can allow deactivating the storage medium based on or after the medical device 108 is switched from the first mode, such as a deactivated mode, to the second mode, such as an activated mode. For example, the processor 104 can request the output device to interface with the storage medium such that the storage medium is locked from further reading, when the storage medium is enabled for such locking. Similarly, the processor 104 can request the output device to interface with the storage medium such that the second content on the storage medium is rendered unusable, when the storage medium is enabled for such data modification rights. Likewise, the processor 104 can request the output device to interface with the storage medium such that the second content on the storage medium is erased from, or otherwise scrambled in, the storage medium, whether temporarily or permanently, when the storage medium is enabled for such data modification rights. Also, the processor 104 can request the output device to interface with the storage medium such that the storage medium is reformatted, when the storage medium is enabled for such data modification rights. Additionally, the processor 104 can request the output device to interface with the storage medium such that the storage medium is modified from a first state to a second state, when the storage medium is enabled for such state modification rights, and where the first state is before the input device 110 obtains the second content from the storage medium, and where the second state is after the input device 110 obtains the second content from the storage medium. Note that such interfacing can include electronically or physically modifying the storage medium or a content or data format thereon. Note that the first state and the second state can differ from each other in various ways (e.g., more or less functionality, more or less energy use, more or less data reading or modification or deletion or reformatting rights). As such, the output device can be useful to lock or wipe the storage medium once the input device 110 reads the second content from the storage medium.

When the system 100D is used to at least one of prevent, diagnose, monitor, ameliorate, or treat the medical condition, disease, or the disorder of the patient, the processor 104D tracks such use and can take an action when a predetermined threshold is satisfied or not satisfied, such as via the logic stored via the memory. For example, the logic tracks a use of the medical device 108D and when a number of uses, as programmed in advance, satisfies or does not satisfy the predetermined threshold, then the processor 104D can take an action, such as switch the medical device 108D between the first mode, such as an activated mode, and the second mode, such as a deactivated mode, or vice versa. Note that the logic has access to or can modify the predetermined threshold. Further, note that the predetermined threshold can be based on a number of single uses within a predefined time period (e.g., within a day, a week, a month, a year) or a number of single uses regardless of any time limit. For example, the action can include activating the medical device 108D, deactivating the medical device 108D, creating, modifying, or deleting a prevention, diagnosis, monitoring, amelioration, or treatment parameter of the medical device 108D, as stored via the medical device 108D or the memory, creating, modifying, or deleting a set of treatment instructions of the medical device 108D, as stored via the medical device 108D or the memory, or others.

In one mode of operation, a user of the system 100D positions the storage medium in proximity thereof, such as within about ten feet or less. The processor 104D and reader 110D then interface with the storage medium such that the processor 104 switches the medical device 108 between the first mode and the second mode. If the first mode was a deactivated mode and the second mode was an activated mode, then the user can use the system 100D to prevent, diagnose, monitor, ameliorate, or treat the medical condition, disease, or the disorder of the user or another. For example, the input device 110 or reader 110D can read the first and/or the second content from the storage medium 112 and pass the first and/or the second content to the processor 104D. In response, the processor 104D can confirm that the first content, which is uniquely associated with the medical device 108D, matches the second card, such as via value and format. Upon such confirmation, the processor 104 switches the medical device 108D from the first mode to the second mode. Alternatively, the processor 104D may simply read the first content and automatically switch the medical device 108D from the first mode to the second mode (i.e., without having a unique content associated with the medical device 108D). In this embodiment, the first content may be erased or scrambled in the storage medium 112 so that it is no longer usable to activate the medical device 108D.

Figure 13:
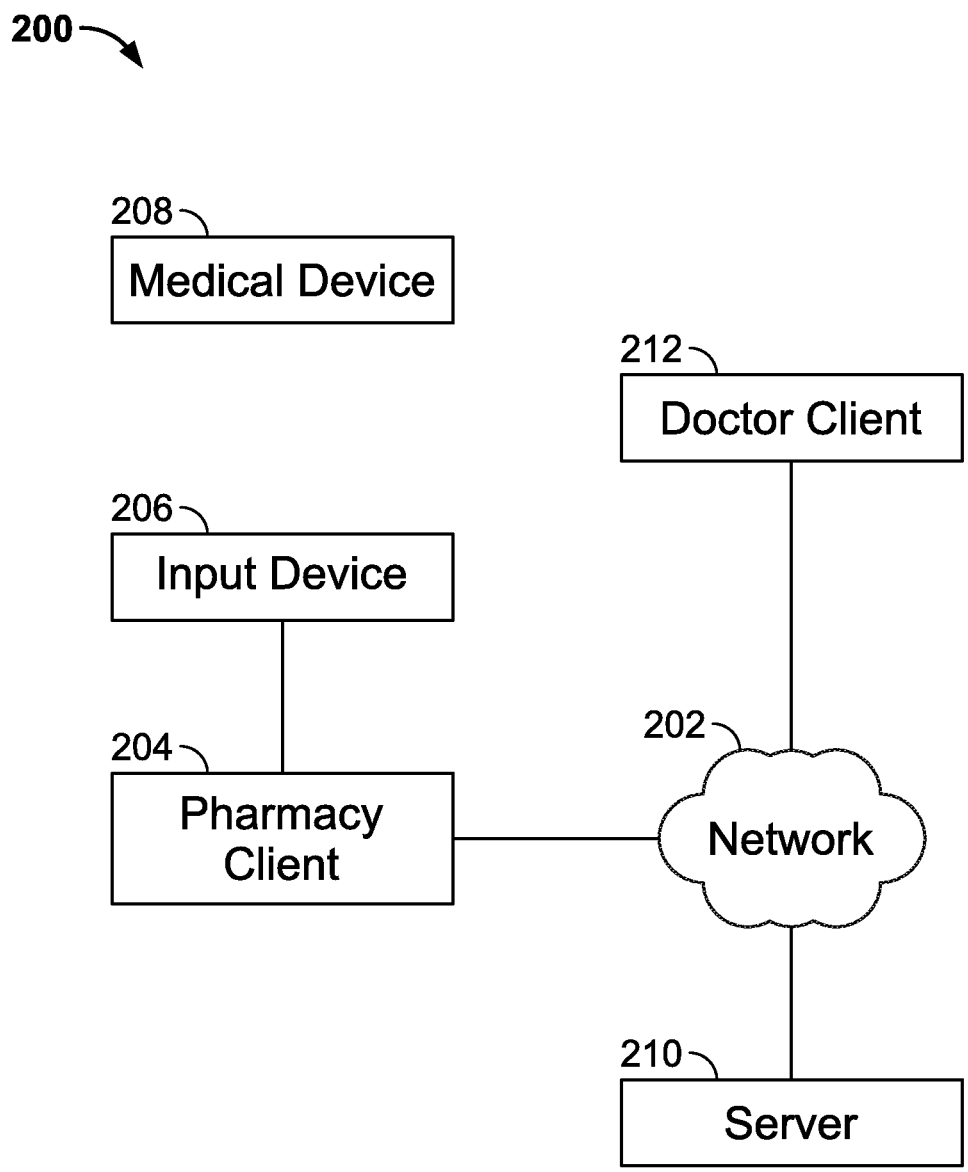
FIG. 13 is a schematic diagram of an embodiment of a network diagram for initially provisioning and refilling a system containing a medical device according to this disclosure.
Figure 14:
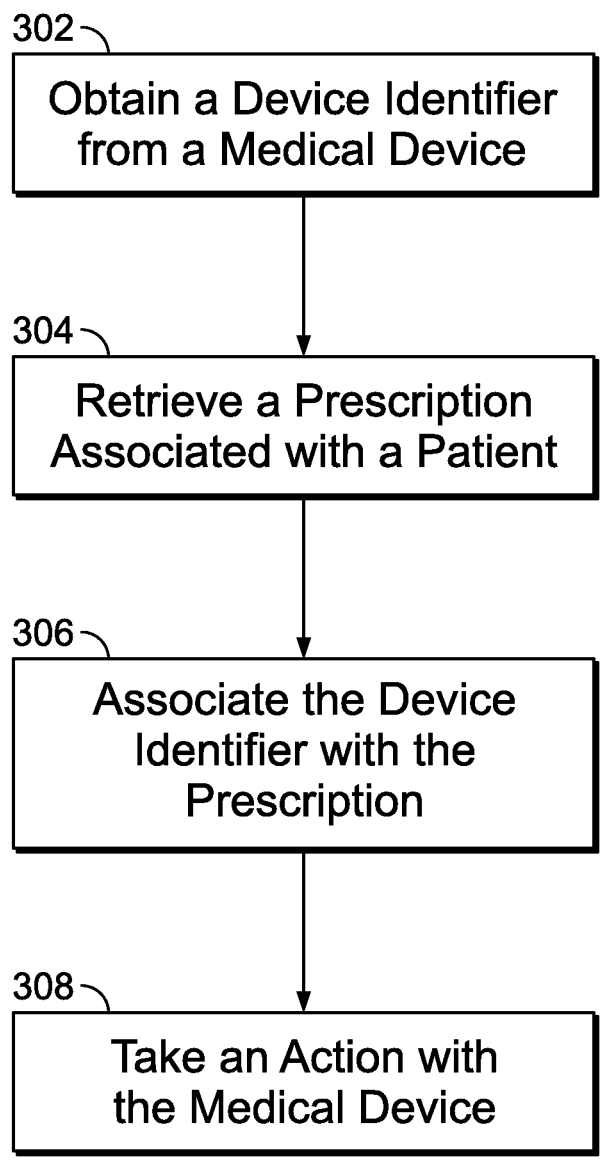
FIG. 14 is a flowchart of an embodiment of a method for initially provisioning a system containing a medical device according to this disclosure.

FIG. 13 shows a schematic diagram of an embodiment of a network diagram for initially provisioning and refilling a system containing a medical device according to this disclosure. FIG. 14 shows a flowchart of an embodiment of a method for initially provisioning a system containing a medical device according to this disclosure. In particular, a system 200 includes a network 202, a pharmacy client 204, an input device 206, a medical device 208, a server 210, and a doctor client 212. Input device 206 may include storage medium 112, which may include a card, such as one described above. The network 202 is in communication, whether over a wireless, wired, or waveguide connection, with the pharmacy client 204, the server 210, and the doctor client 212. The pharmacy client 204 is in communication, whether over a wireless, wired, or waveguide connection, with the input device 206 and the network 202.

The network 202 includes a plurality of nodes that allow for sharing of resources or information. The network 202 can be wired or wireless. For example, the network 202 can be a local area network (LAN), a wide area network (WAN), a cellular network, a satellite network, or others.

Each of the pharmacy client 204 and the doctor client 212 is a workstation that runs an operating system, such as MacOS®, Windows®, or others, and an application, such as an administrator application, on the operating system. The workstation can include and/or be coupled to, whether directly and/or indirectly, an input device, such as a mouse, a keyboard, a camera, whether forward-facing and/or back-facing, an accelerometer, a touchscreen, a biometric reader, a clicker, a microphone, a barcode or QR code reader, or any other suitable input device. The workstation can include and/or be coupled to, whether directly and/or indirectly, an output device, such as a display, a speaker, a headphone, a printer, or any other suitable output device. In some embodiments, the input device and the output device can be embodied in one unit, such as a touch-enabled display, which can be haptic. As such, the application presents a graphical user interface (GUI) configured to interact with a user to perform various functionality, as disclosed herein. In some embodiments, the application on the pharmacy client 204 can operate in an administrator mode and a kiosk mode, such as an agent mode or others, where the administrator mode has more or higher access privileges than the kiosk mode, where the kiosk mode is used for programming the input device 206 (or storage medium 112), programming the medical device 208 or coupling the medical device 208 to the storage medium, as disclosed herein. Note that the application on the pharmacy client 204 can control access between the administrator mode and the kiosk mode via user identifiers, passwords, biometrics, or others. Further, note that at least one of the pharmacy client 204 or the doctor client 212 can be a non-workstation computer as well, such as a smartphone, a tablet, a laptop, a wearable, an eyewear unit, or others.

The server 210 runs an operating system, such as MacOS®, Windows®, or others, and an application, such as a prescription management application, on the operating system. In some embodiments, the server 210 hosts or has access to a database, such as a relational database, an in-memory database, a graphical database, a NoSQL database, or others. For example, the database can include a plurality of records, where each of the records contains a plurality of fields associated with a plurality of categories, such as patient identifier, patient contact information, patient medical record, prescription name, prescription dosage, and others. Note that the database can include or be coupled to an electronic medical records (EMR) database, whether local or remote thereto, whether using a same or different schema (e.g., star, tree). The server 210 can include and/or be coupled to, whether directly and/or indirectly, an input device, such as a mouse, a keyboard, a camera, whether forward-facing and/or back-facing, an accelerometer, a touchscreen, a biometric reader, a clicker, a microphone, or any other suitable input device. The server 210 can include and/or be coupled to, whether directly and/or indirectly, an output device, such as a display, a speaker, a headphone, a printer, or any other suitable output device. In some embodiments, the input device and the output device can be embodied in one unit, such as a touch-enabled display, which can be haptic.

The input device 206 or storage medium 112 may be coupled to the pharmacy client 204, whether over in a wired, wireless, or waveguide connection, and can include a camera, a microphone, a keyboard, whether physical or virtual, a reader, or others. The input device 206 can be battery powered or powered via the pharmacy client 204. Alternatively, input device 206 may be a storage medium 112, such as a card or the like.

In some embodiments, the medical device 208, such as the system 100A, the medical device 108, or others, comprises a device identifier, such as the first content, as disclosed herein, whether internally, such as via the memory 106 or others, or externally, such as on the medical device 108 itself, on a tag coupled to the medical device 108, such as via adhering, fastening, mating, or others, or on a tag coupled to or depicted or printed on a package containing the medical device 208.

In one mode of operation, as shown in FIG. 14, in order to initially provision the medical device 208, the doctor client 212 sends a set of prescription data to the server 210 over the network 202. As per block 304, the pharmacy client 204 retrieves (e.g., reads, copies) the set of prescription data from the server 210 over the network 202, such as via a patient identifier associated with a record of the database accessible to the server 210. Upon retrieval, the pharmacy client 204 displays the set of prescription data thereon.

As per block 302, a user of the pharmacy client 204 uses the input device 206 to obtain the device identifier from the medical device 208. For example, when the device identifier, such as the first content, is internal to the medical device 208, then the input device 206 can interface with the medical device 208, whether over a wired, wireless, or waveguide connection, and obtain the device identifier, such as via an RFID interrogation or others. Likewise, when the device identifier is external to the medical device 208, then the input device 206 obtains the device identifier via reading the device identifier, such as via barcode or QR code scanning or others. Note that the block 302 can occur before, during, or after the block 304. As such, once the pharmacy client 204 has the device identifier and the set of prescription data, as per block 306, the pharmacy client 204 associates the device identifier and the set of prescription data, whether locally or on the server 210, such as via relating the device identifier and the set of prescription data in the database, such as via a primary key or others. Therefore, as per block 308, an action can be taken with the medical device 208. For example, the action can be via the pharmacy client 210 prompting a message that the medical device 208 is associated with the set of prescription data, generating a sound alert, modifying a data structure, or others. Similarly, the action can include packaging or repackaging the medical device 208, shipping the medical device 208, handing over the medical device 208 to a patient, or others.

Figure 15:
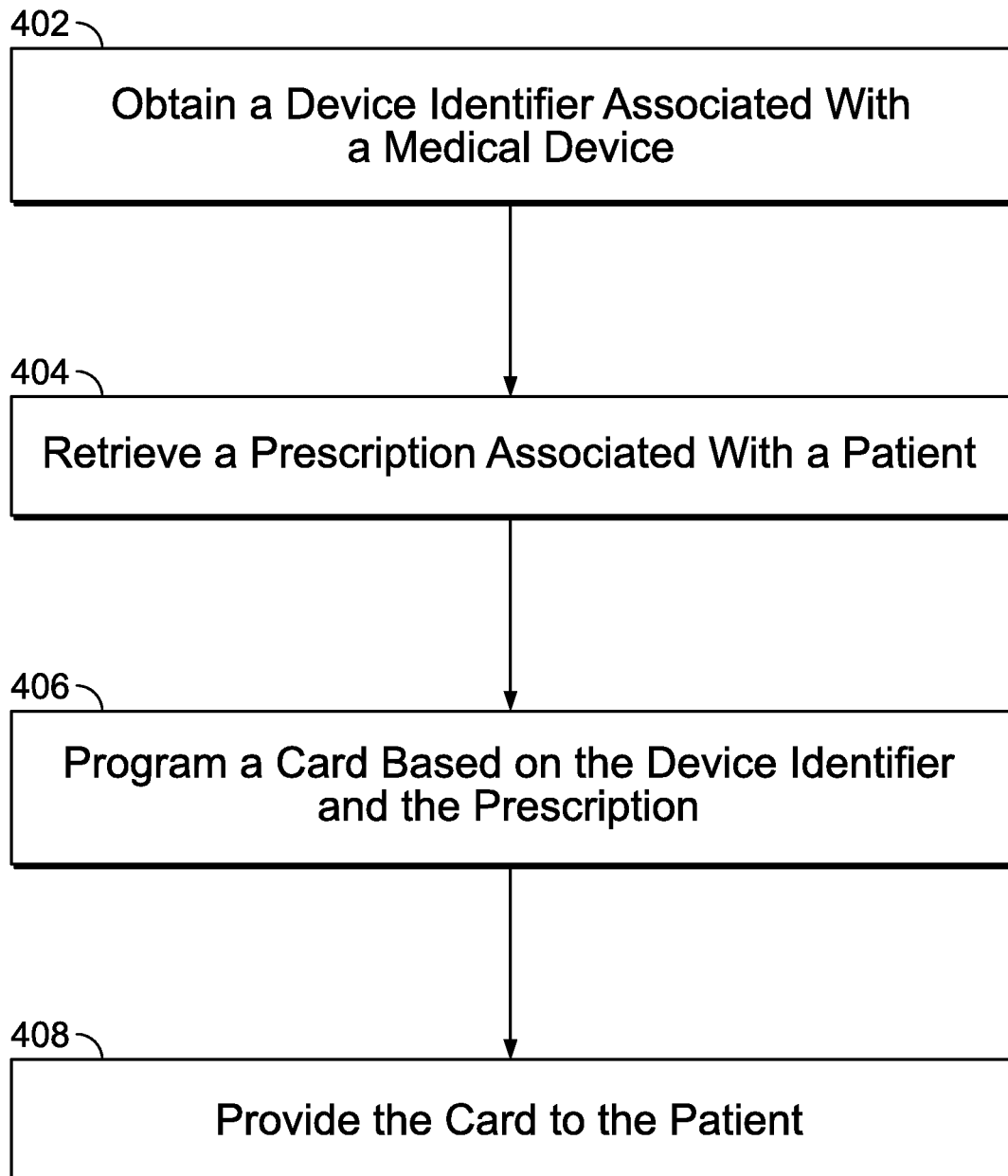
FIG. 15 is a flowchart of an embodiment of a method for refilling a system containing a medical device according to this disclosure.

FIG. 15 shows a flowchart of an embodiment of a method for refilling a system containing a medical device according to this disclosure. In particular, in order to refill the medical device 208, the doctor client 212 sends a set of prescription data to the server 210 over the network 202. As per block 404, the pharmacy client 204 retrieves (e.g., reads, copies) the set of prescription data from the server 210 over the network 202, such as via a patient identifier associated with a record of the database accessible to the server 210. Upon retrieval, the pharmacy client 204 displays the set of prescription data thereon.

As per block 402, a user of the pharmacy client 204 uses the input device 206 to obtain the device identifier from the medical device 208. For example, when the device identifier, such as the first content, is internal to the medical device 208, then the input device 206 can interface with the medical device 208, whether over a wired, wireless, or waveguide connection, and obtain the device identifier, such as via an RFID interrogation or others. Likewise, when the device identifier is external to the medical device 208, then the input device 206 obtains the device identifier via reading the device identifier, such as via barcode or QR code scanning or others. Note that the block 402 can occur before, during, or after the block 404.

As such, once the pharmacy client 204 has the device identifier and the set of prescription data, as per block 406, the pharmacy client 204 can be used to program or reprogram a storage medium, such as an RFID card or others, based on the set of prescription data, via an output device, such as a signal transmitter, a light, sound, or vibration source, an actuator, a data writer, or others, coupled to the pharmacy client 204, whether over a wired, wireless, or waveguide connection. For example, such programming can be via an RFID interrogation or other technologies. For example, such programming can involve using the pharmacy client 204 to program the storage medium to match the device identifier that is uniquely associated with the medical device 208. For example, the pharmacy client 204 can instruct the output device to interface with the storage medium, such as via adding, modifying, or deleting content or format to or from the storage medium such that the storage medium stores the set of prescription data or a logic containing a set of instructions to operate the medical device 208 according to the set of prescription data. Note that this logic can be included in the set of prescription data or generated via the server 210 or the pharmacy client 204 based on the set of prescription data. In some embodiments, the medical device 208 generates this logic based on the set of prescription data as obtained from the storage medium. Therefore, the storage medium can be positioned in proximity (e.g., within about 10 feet or less) of the system 100A to be read via the input device 110 such that the processor 104 can switch the medical device 108 between the first mode and the second mode. Note that for recordkeeping purposes, the pharmacy client 204 can communicate (e.g., email, texting, social networking, over-the-top) a message informative of such programming to the server 210 over the network 202, such as for writing into the record of the patient in the database. For example, the pharmacy client 204 associates the device identifier and the set of prescription data, whether locally or on the server 210, such as via relating the device identifier and the set of prescription data in the database, such as via a primary key or others.

Consequently, as per block 408, the storage medium, as programmed, can be provided to the patient, such as via handing over to the patient, packaging/shipping to the patient, or communicating to the patient, such as via email, text, social networking, over-the-top messaging, or others. As such, a POS terminal, such as the pharmacy client 204, can be used to (1) obtain a device identifier from the medical device 208, (2) retrieve a set of prescription data from the server 210, where the device identifier is uniquely associated with the medical device 208, and (3) program, such as via encoding or others, a storage medium, such as an RFID card or others, based on the device identifier and the set of prescription data such that the medical device 208 can be switched from a first mode, such as a deactivated mode, to a second mode, such as an activated mode, or load a set of new therapy dose data, based on the storage medium being in proximity of the medical device 208.

In some embodiments, the output device can include a transmitter (e.g., wired, wireless, waveguide) and the pharmacy client 204 can instruct the transmitter to send (e.g., wired, wireless, waveguide) a signal to the storage medium such that the storage medium can receive and process the signal, which may involve acting based on such processing. For example, the pharmacy client 204 can request the output device to interface with the storage medium such that the storage medium is locked from further reading or writing or modifying or deleting, whether in data or format, when the storage medium is enabled for such locking. Similarly, the pharmacy client 204 can request the output device to interface with the storage medium such that the second content on the storage medium is rendered unusable, when the storage medium is enabled for such data modification rights. Likewise, the pharmacy client 204 can request the output device to interface with the storage medium such that the second content on the storage medium is erased from, or scrambled in, the storage medium, whether temporarily or permanently, when the storage medium is enabled for such data modification rights. Also, the pharmacy client 204 can request the output device to interface with the storage medium such that the storage medium is reformatted, when the storage medium is enabled for such data modification rights. Note that such interfacing can include electronically or physically modifying the storage medium or a content or data format thereon or an encryption thereon.

Figure 16:
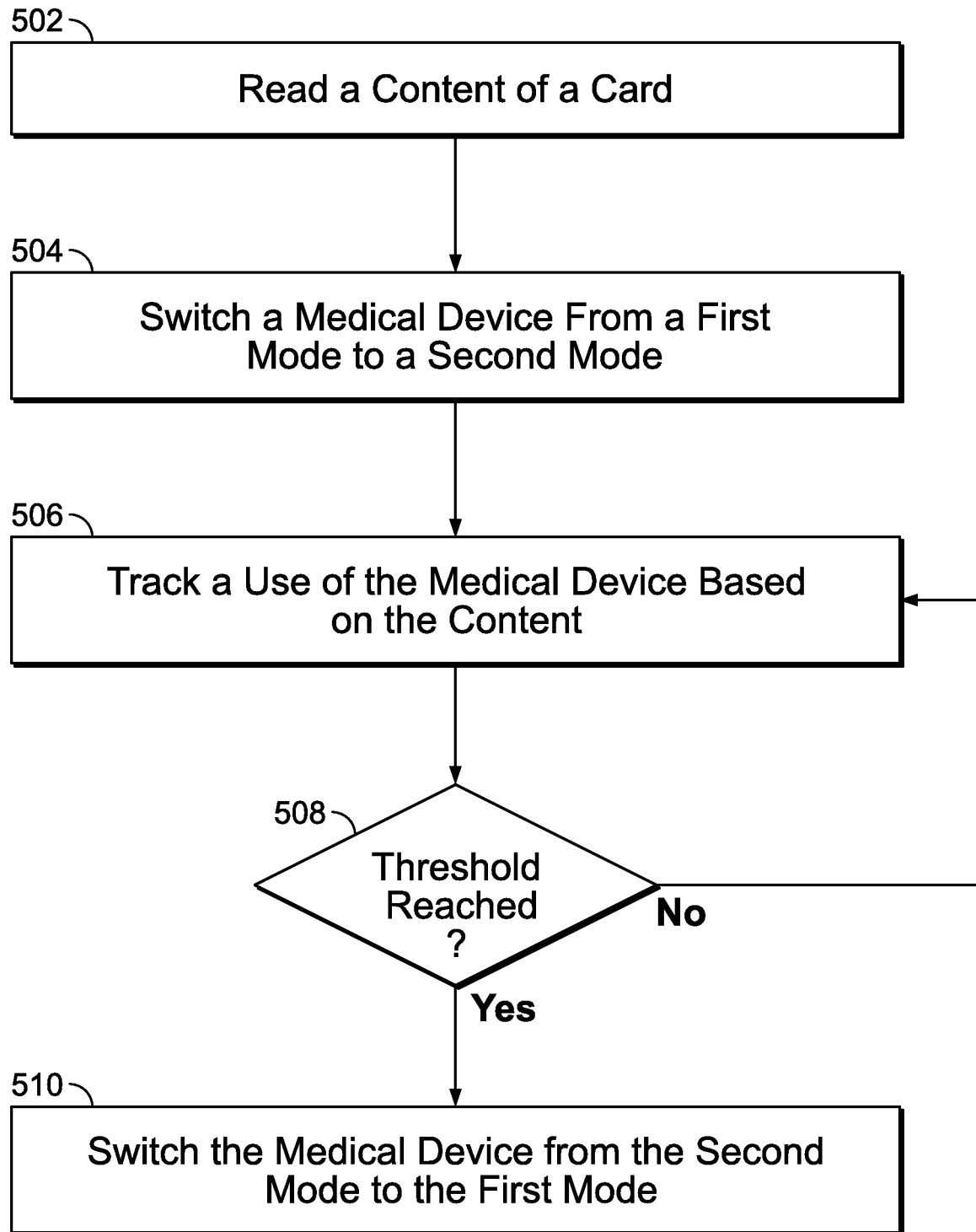
FIG. 16 is a flowchart of an embodiment of a method for using a system containing a medical device according to this disclosure.

FIG. 16 shows a flowchart of an embodiment of a method for using a system containing a medical device according to this disclosure. In particular, as per block 502, a storage medium 112, such as an RFID card or others, is positioned in proximity of the input device 110, such as an RFID reader, such that the input device 110 can read a content of the storage medium. The input device 110 may comprise reader 110D, which can be positioned within housing 102D and/or within medical device 108D. For example, the content can include an activation code and a set of prescription data, such as a therapy dosage or others. For example, such reading can occur at a patient location such as at home, at work, or others, at a pharmacy location, such as at a retail kiosk or others, at a manufacturer location, such as at a warehouse or others, or others. As per block 506, responsive to such reading, the processor 104 switches the medical device 108 from a first mode, such as a deactivated mode, to a second mode, such as an activated mode.

In some embodiments, the processor 104 instructs the output device of the system 100A to communicate with the storage medium in order to deactivate the storage medium 112, as disclosed herein, such as via deleting or scrambling the content from the storage medium 112, reformatting the card, or others. In these embodiments, storage medium 112 can be used only one-time. However, storage medium 112 can be used with any number of medical devices 108 that are capable of reading the first content on storage medium 112. By deleting the content from storage medium 112, this ensures that the card cannot be used more than once (i.e., used by one medical device 108 and then used by another).

As per block 508, the processor 104 tracks usage of the medical device 108 in order to be compliant with the content of the storage medium as read by the input device 110 or reader 110D. For example, if the content mandates 1 use during 24 hours for 1 week, then the processor 104 track time, days, and usage per day or another time period (e.g., minutes, hours). As per block 508, if the processor 104 determines that the usage of the medical device has reached a predetermined threshold, as per the content read from the storage medium, then the processor 104 switches the medical device 108 from the second mode (the activated mode) to the first mode (the deactivated mode), otherwise the processor 104 allows the usage of the medical device 108. For example, if the content mandates 1 use during 24 hours for 1 week, then the processor 104 switches the medical device 108 from the second mode to the first mode when 1 week from first use of the medical device 108 passed.

Figure 17B:
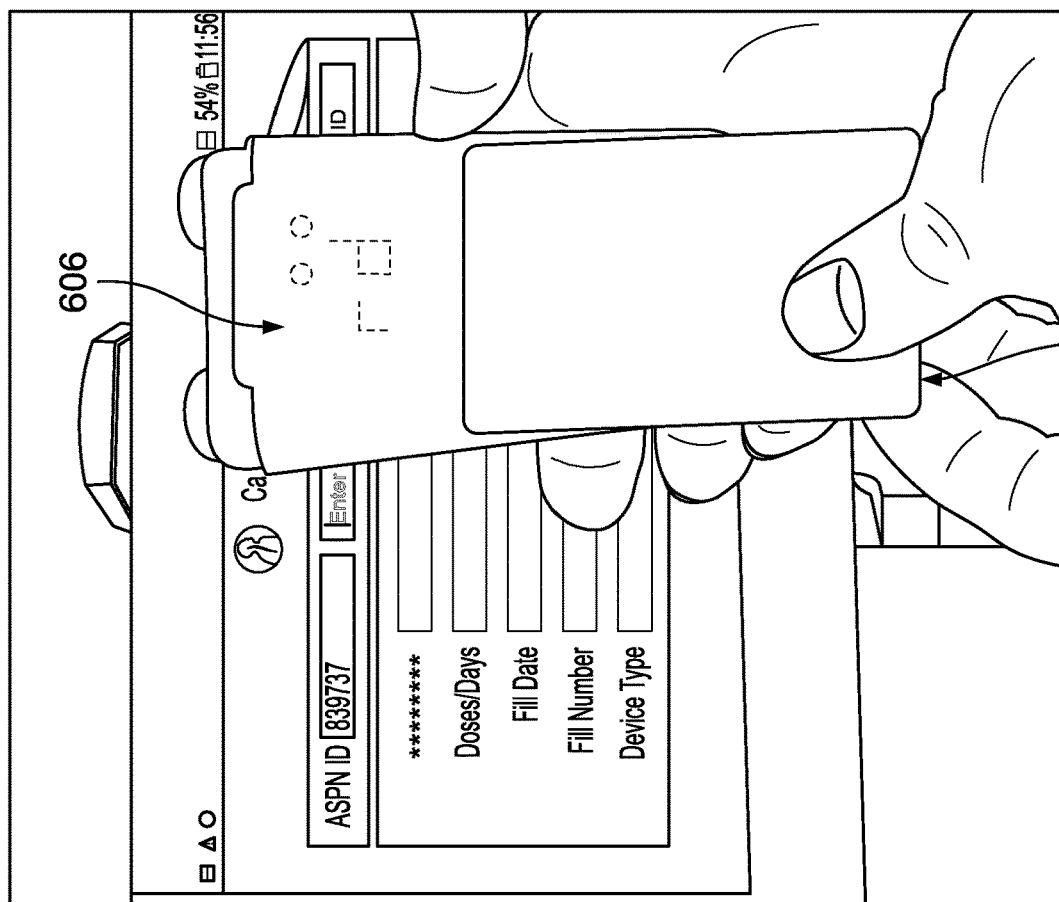
FIGS. 17A-17B illustrate an embodiment of a technique for pairing a patient/card and a medical device thereby establishing a master patient/card to device mapping according to this disclosure.
Figure 17A:
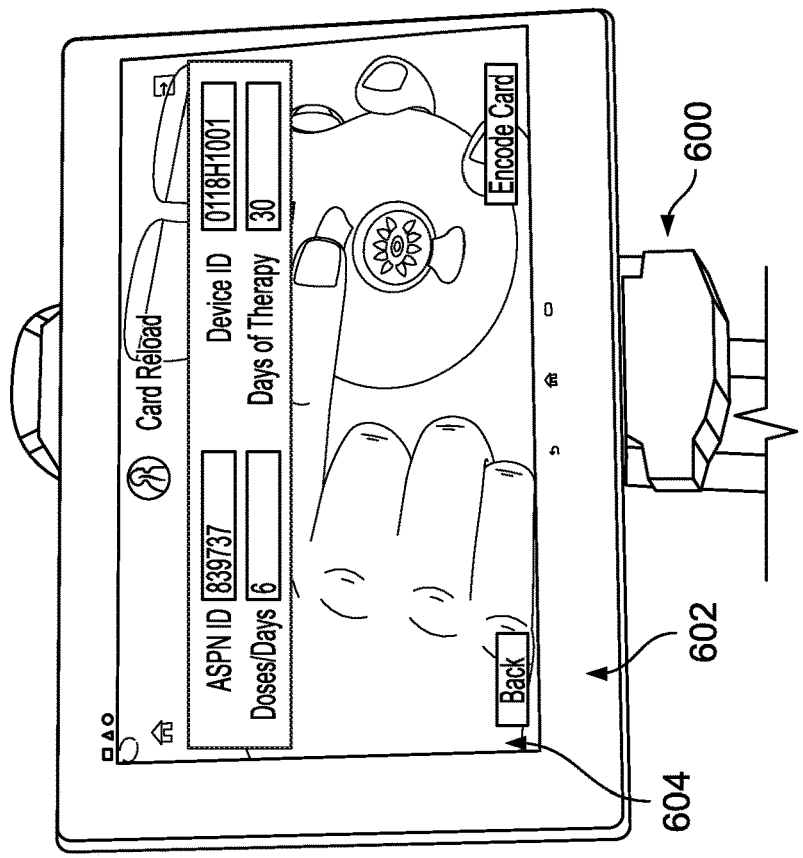
Figure 17C:
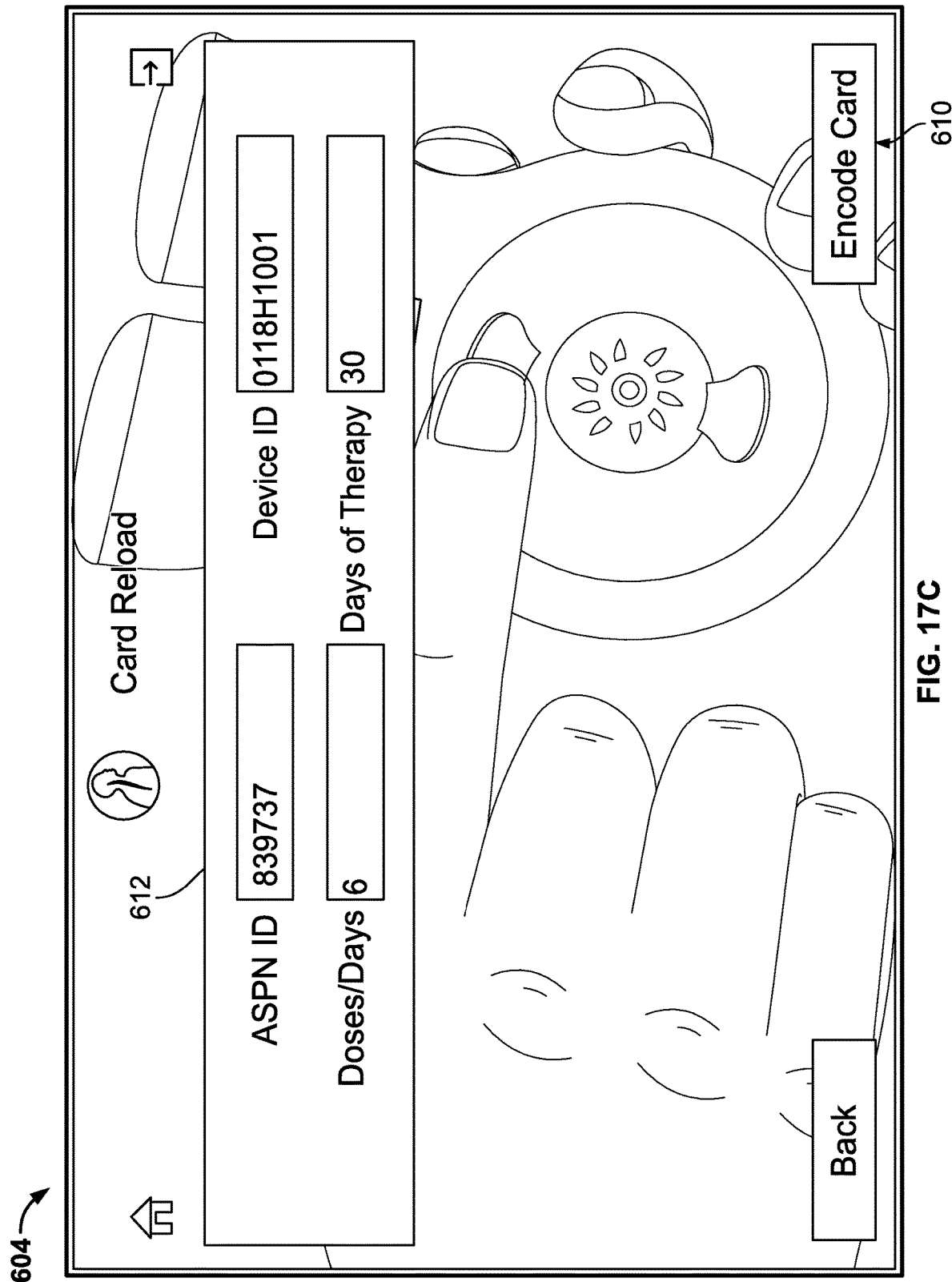
FIG. 17C illustrates an embodiment of a graphical user interface (GUI) for programming a storage medium according to this disclosure.

FIGS. 17A, 17B show an embodiment of a technique for pairing a patient/card and a medical device thereby establishing a master patient/card to device mapping according to this disclosure. FIG. 17C shows an embodiment of a GUI for programming a storage medium according to this disclosure. As shown in FIG. 17A, a POS terminal 600 includes a touch-enabled display 602 that displays a wizard 604. The POS terminal 600 also includes a camera, whether front or back, and can include a flash illumination device, whether front or back. The POS terminal 600 runs the wizard 604, whether as a local process or over a network connection from a remote data source, such as via browsing or streaming. Alternatively, display 602 may be located on the neurostimulator 606. In this embodiment, the same general method is used except that there is no requirement for POS terminal 600.

As shown in FIG. 17B, a neurostimulator 606 is positioned adjacent to a card 608, which may include a physical contact therebetween or be contactless therebetween, such within about 12 inches or less therebetween, although greater distances are possible, such as over a personal area network (PAN), a LAN, or a WAN. As shown in FIG. 17C, the wizard 604 (or the display on the neurostimulator 606) contains a plurality of pages and at least one of the pages presents a plurality of display fields 612 and a plurality input elements 610. In an alternative embodiment, wizard 604 or something similar thereto, may be contained within the neurostimulator 606.

As such, in order to initially provision or refill the neurostimulator 606 for a neurostimulation (or another medical modality) session, as shown in FIGS. 17A and 17C, a user of the POS terminal 600 or the neurostimulator 606 touch-interacts with the wizard 604 on the display 602 via the input elements 610. In response, the POS terminal 600 or the neurostimulator 606 communicates with a remote data source, such as over the network 202 with the server 210 of FIG. 13, and receives a set of initial provisioning or refill data from the remote data source for a patient, whether identical to or different from the user. The POS terminal 600 or the neurostimulator 606 then displays the set of initial provisioning or refill data via the display fields 612. For example, the display fields 612 display a patient identifier, such as an alphanumeric string, a device identifier, such as an alphanumeric string, a dosage amount, such as a numeric string, and a days of therapy amount, such as a numeric string. For example, there can be about 10, 31, or 93 (or less or more) days or uses of therapy as prescribed by a medical service provider, such as a physician. For example, the dosage amount can be about 2 minutes as prescribed by a medical service provider, such as a physician. Resultantly, the user positions the card 608 adjacent to the POS terminal 600 or the neurostimulator 606 and then further touch-interacts with the wizard 604 such that the POS terminal 600 or the neurostimulator 606 programs the card 608 in accordance with the set of initial provisioning or refill data, as presented via the display fields 612. Note that the POS terminal 600 or the neurostimulator 606 can program the card 608 in a wired manner, such as via a card reader of the POS terminal 600 or neurostimulator 606, or in a wireless or waveguide manner, such as via a transceiver of the POS terminal 600 or neurostimulator 606.

Accordingly, as shown in FIG. 17B, the card 608, as pre-programmed via the POS terminal 600 or the neurostimulator 606, is positioned adjacent (e.g., within about 10 feet or less) to the neurostimulator 606 such that the neurostimulator 606 switches from a first mode, such as a deactivated mode, to a second mode, such as an activated mode, as disclosed herein. In some embodiments, the POS terminal 600 or the neurostimulator 606 can include a cash register that communicates with a tablet, whether in wired, wireless, or waveguide manner, such that the POS terminal 600 or neurostimulator 606 and the table are distinct physical devices, with the tablet being used to programmatically initially provision or refill the card 608, which can include via communication with the POS terminal 600 or neurostimulator 606. Note that the tablet is illustrative and other computing devices can be used, whether additionally or alternatively, such as smartphone, laptop, desktop, eyewear unit, wearable, or others.

In another embodiment, the card 608 is pre-programmed with a first content at the manufacturing or distribution site. As such the card 608, as pre-programmed, is positioned adjacent (e.g., within about 10 feet or less) to the neurostimulator 606 such that the neurostimulator 606 switches from a first mode, such as a deactivated mode, to a second mode, such as an activated mode, as disclosed herein. After the neurostimulator has switched to the second mode, the first content of the card 608 is erased or scrambled so that it is no longer usable to activate the neurostimulator 606.

Figure 18:
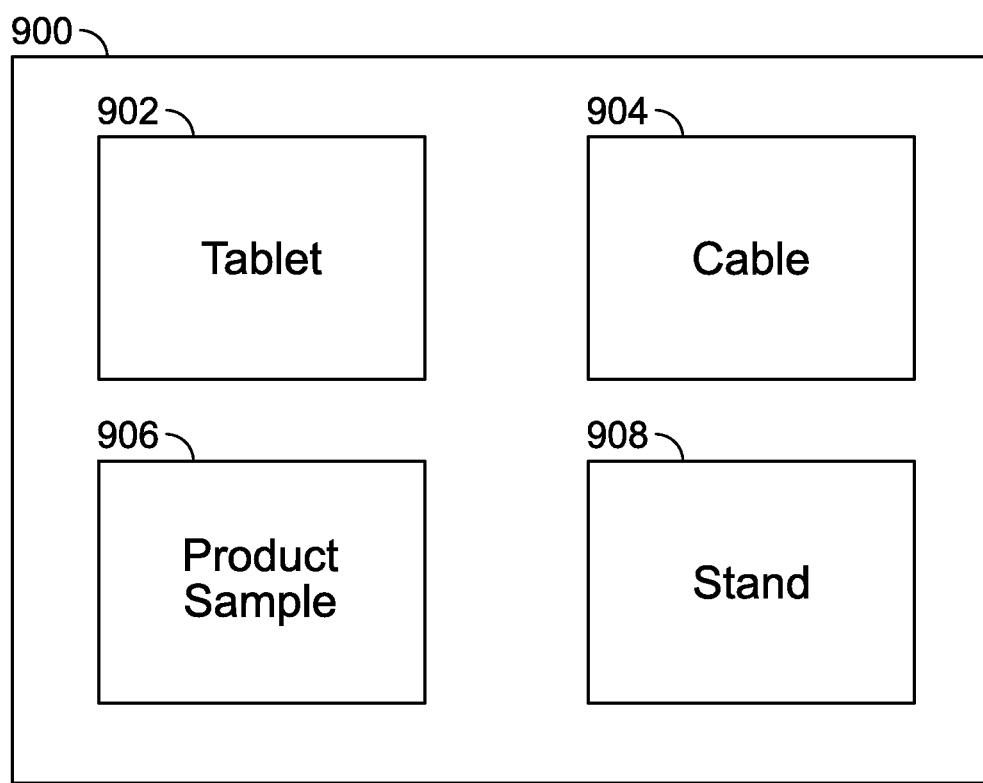
FIG. 18 illustrates an embodiment of a kit according to this disclosure.

FIG. 18 shows an embodiment of a kit according to this disclosure. A kit 900 includes a tablet 902, a cable 904, a product sample 906, and a stand 908. For example, the tablet 902, the cable 904, the product sample 906, and the stand 908 can be hosted within a package, whether snugly or non-snugly, such as a cardboard box, a plastic pack, a fabric container, an intermodal container, or others. The tablet 902 can be used as a POS terminal, as disclosed herein. The cable 904 can charge the tablet 902 from a wall socket or from a computing device. The cable 904 can also be used for transferring data to or from the tablet 902. For example, the cable 904 can be a USB cable, a Firewire cable, or others. The product sample 906 can include a product label, which can include a barcode, such as a QR code. The stand 908 can support the tablet 902 when the tablet 902 is used as a POS terminal, as disclosed herein. Note that the tablet 902 can also be used without the stand 908.

The tablet 902 hosts a plurality of apps and is configured to operate in a plurality of modes, including a pharmacy admin mode and a pharmacy agent mode. The apps include initial provisioning and refilling (IPAR) app, which can interface with a remote or local data source when running on the tablet 902, whether the tablet 902 is in wired, wireless, or waveguide communication with the remote data source. The tablet 902 can receive the IPAR app from a network-based data source, such as a server (e.g., physical, virtual, web, application, database), or from a memory load, such as via a memory stick, or others. The tablet 902 controls access to the modes based on a user login, which may be via passwords, two factor authentication, biometrics (e.g., fingerprints, retina scans), or others. In some embodiments, the tablet 902 controls access to the modes based on the user login into the IPAR app. The pharmacy admin mode grants an administrator level access to functionality of the tablet 902 and the apps hosted thereon, including the IPAR app. The pharmacy agent mode grants a limited user level access to functionality of the tablet 902 such that the tablet 902 is operated in a kiosk mode involving the IPAR app. For example, in the pharmacy agent mode, a user may be prevented from accessing any, some, most, or all apps other than the IPAR app. Note that the modes may display various visually distinct indicia notifying of what mode the tablet 902 is operating in. For example, the visual indicia can include icons, alphanumeric labels, graphics, images, watermarks, backgrounds, fonts, or any other visual elements, where the visual indicia differ between the modes.

Alternatively, kit 900 may include only the product sample 906 and a storage medium 112, such as an RFID card discussed above. In this embodiment, the plurality of apps may reside within the product sample 906 or the storage medium 112. The storage medium 112 and the product sample 906 may be connected wirelessly, or through a wired connection, such as cable 904 or another type of connection.

Figure 19A:
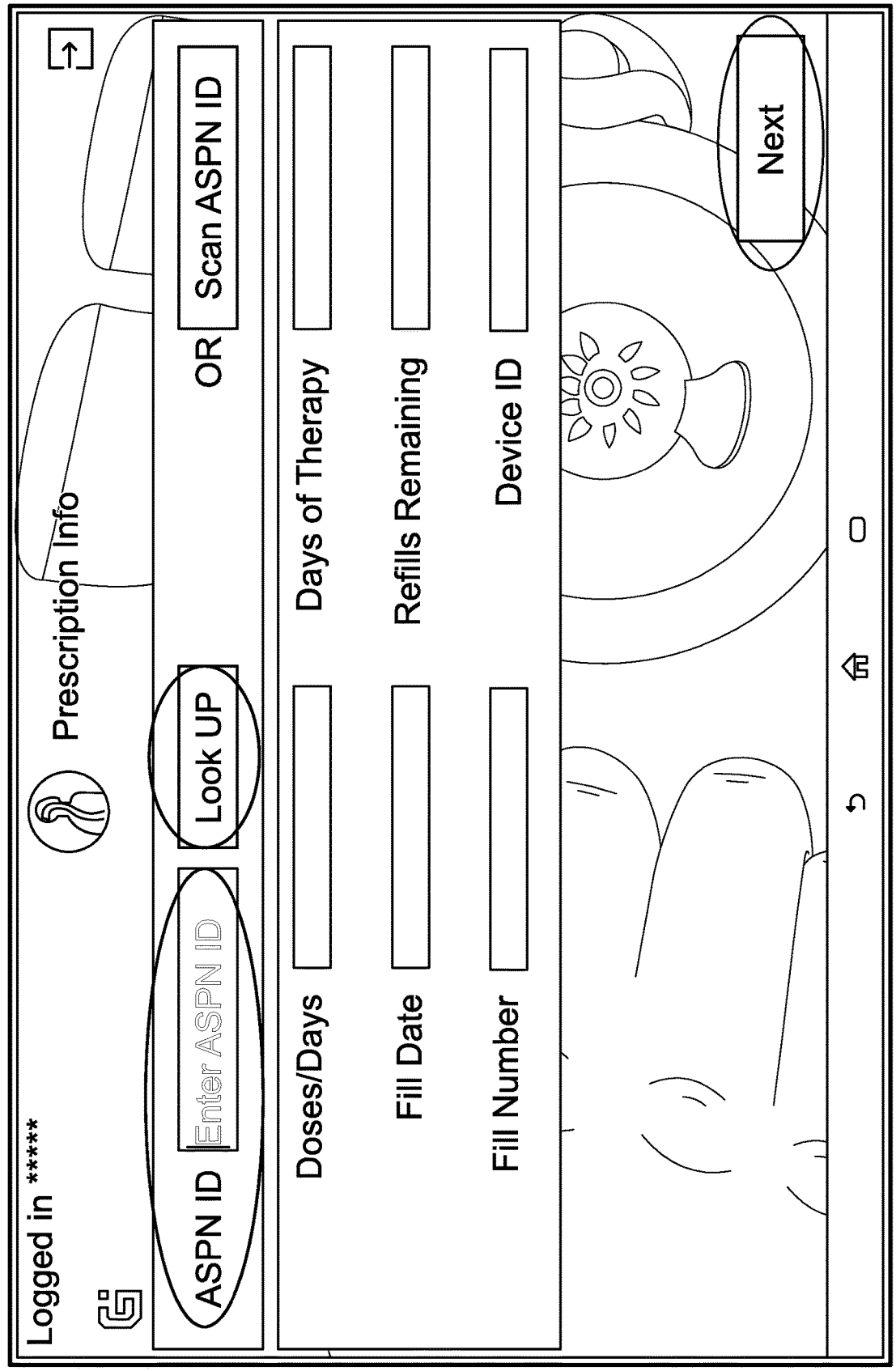
Figure 19C:
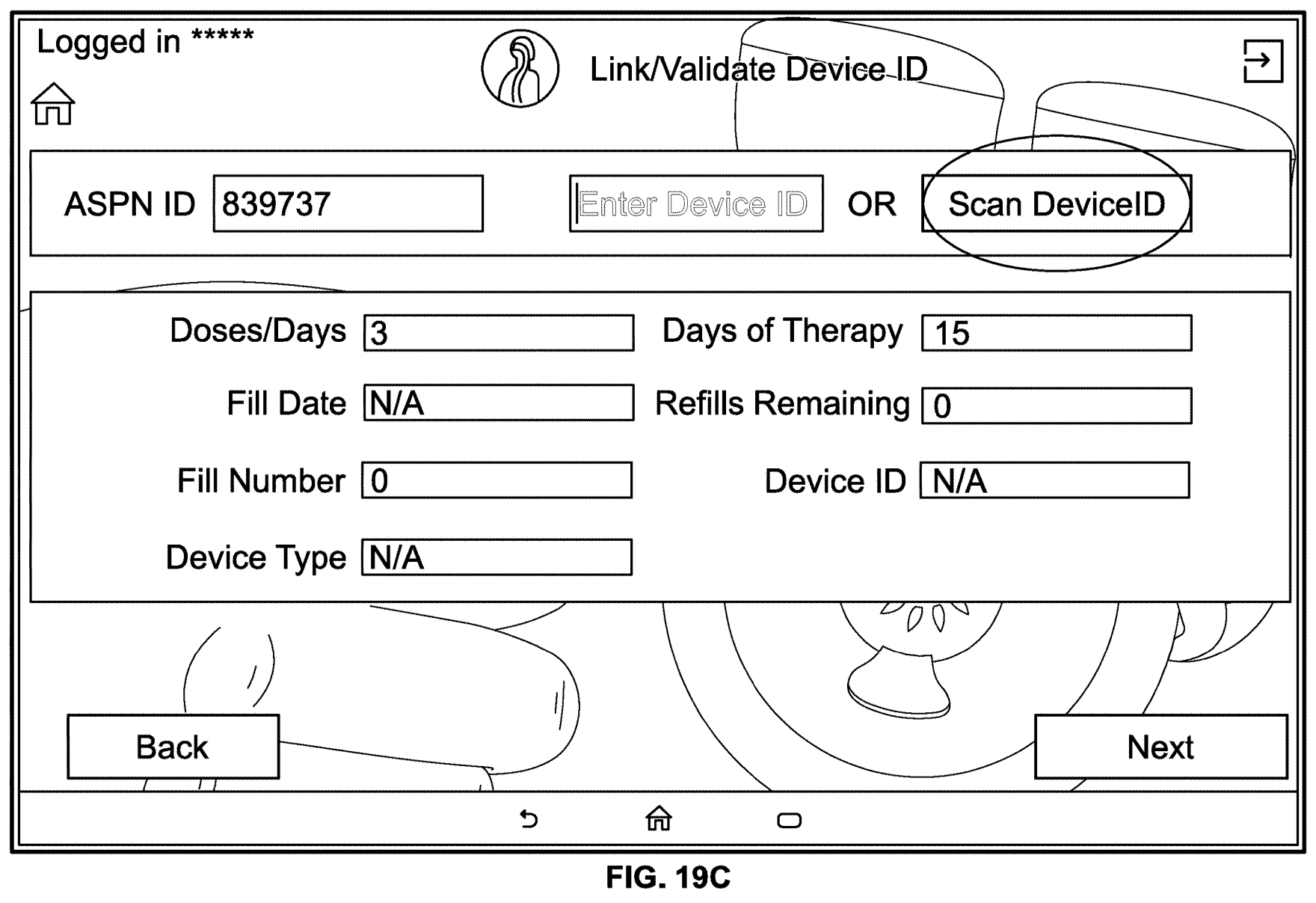

FIGS. 19A-19G show an embodiment of a process of pairing a patient/card and a medical device thereby establishing a master patient/card to device mapping according to this disclosure. The wizard 604 may be used in this process and, as shown in FIG. 19A, the user operates the POS terminal 600 to input a referral identifier, such as an alphanumeric string, into one of the display fields 612 and interacts with one of the input elements 610 to submit the referral identifier to the remote data source for retrieving the set of initial provisioning or refill data. As in previous embodiments, the functions of wizard 204 and POS terminal 600 may be provided directly by neurostimulator 606.

As shown in FIG. 19B, the remote source retrieves the set of initial provisioning or refill data and sends the set of initial provisioning or refill data to the POS terminal 600 such that the POS terminal 600 populates some, most, or all remaining display fields 612 with corresponding information extracted or copied from the set of initial provisioning or refill data. Note that if such remaining display fields 612 do not populate or do not fully populate, then such error may be due to the referral identifier being incorrectly entered or being invalid. Further, note that upon such lack of population or lack of full population, the POS terminal 600 may display a warning message via the wizard 604, with the warning message requesting re-entry of the referral identifier or suggesting a call to a predetermined phone number, which may be remotely updatable.

As shown in FIG. 19C, the user again operates the POS terminal 600 to have the POS terminal 600 optically read the neurostimulator 606 (or another medical device) via the camera, such as via barcode scanning.

Figure 19E:
Figure 19D:
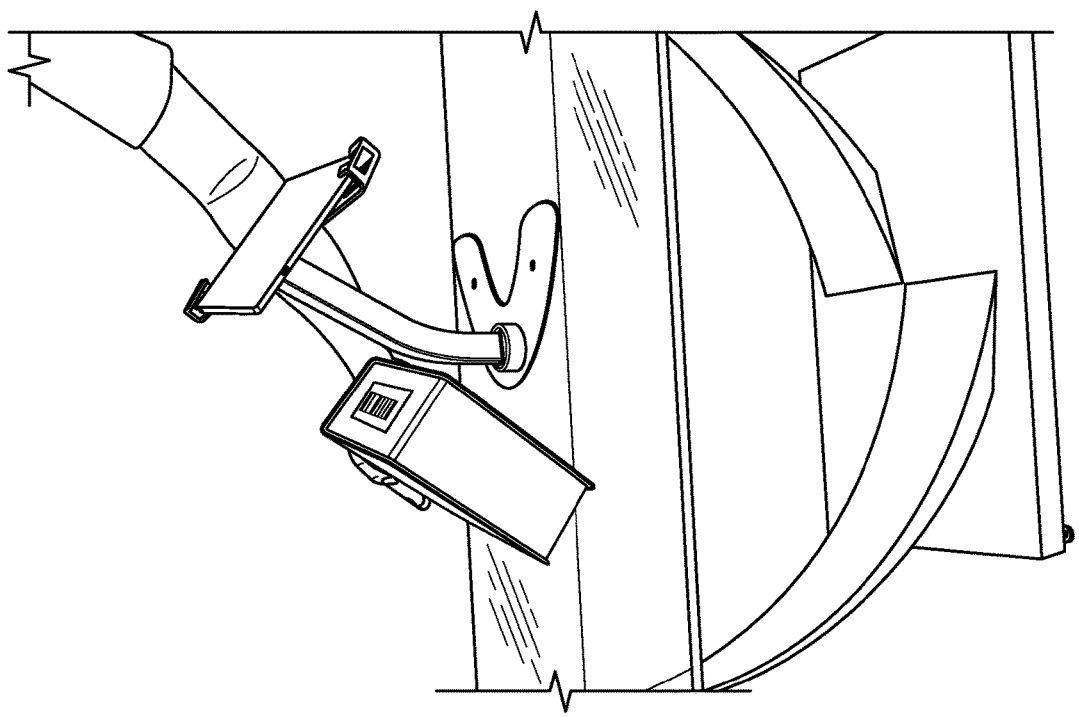

As shown in FIG. 19D, the user selects the neurostimulator 606 from an inventory and holds the neurostimulator device 606 with a label having a barcode facing up behind POS terminal 600 such that the camera of the POS terminal 600 can read the barcode. Note that the neurostimulator 606 can be packaged within a package, such as a cardboard box or others, as explained herein, where the package or the neurostimulator 606 hosting the label, or be outside of the package, with the package or the neurostimulator 606 hosting the label. As such, the POS terminal 600 captures an image of the barcode.

As shown in FIG. 19E, as the POS terminal 600 focuses on capturing the barcode, the POS terminal 600 displays a bounding box (e.g., square, rectangle, oval, circle, triangle, pentagon, octagon, hexagon, polygon) or another closed (e.g., O-shape, D-shape) or open shape (e.g., U-shape, C-shape) extending around or about the barcode within the display 602. Further, note the POS terminal 600 can display multiple bounding boxes, which are visually distinct from each other, such as via color, shape, background, foreground, line style, or others. Moreover, note that the barcode is scanned by aligning the bounding box over the barcode such that the barcode is positioned within the bounding box and activating, such as via touching the display 602, the bounding box to capture the image of the barcode. Additionally, note that in poor illumination conditions, the POS terminal 600 can activate the flash illumination device to assist in capturing the image of the barcode. Furthermore, if the POS terminal 600 is unable to capture the barcode, then the wizard 604 presented on the POS terminal 600 enables a manual entry of a device identifier, which may be validated against a set of device identifiers, whether stored locally on the POS terminal 600 or stored or accessible via the remote data source.

Figure 19F:
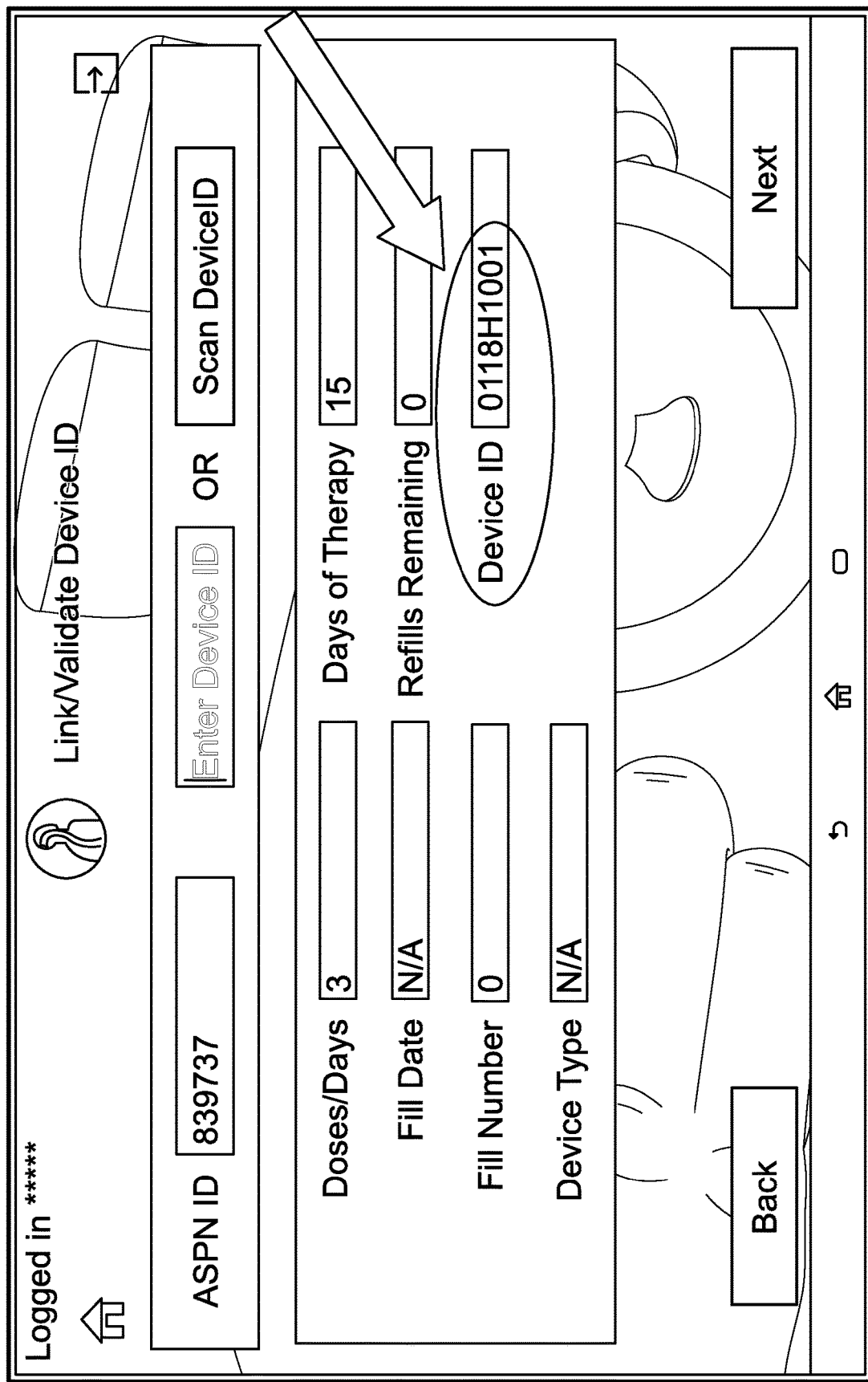

As shown in FIG. 19F, after the POS terminal 600 captures the image that depicts the barcode, the POS terminal 600 processes the image to extract, which may include format or value conversion, a device identifier, such as an alphanumeric string, from the image, such as via various optical character recognition and other computer vision techniques, and populates the device identifier into one of the display fields 612.

Figure 19G:
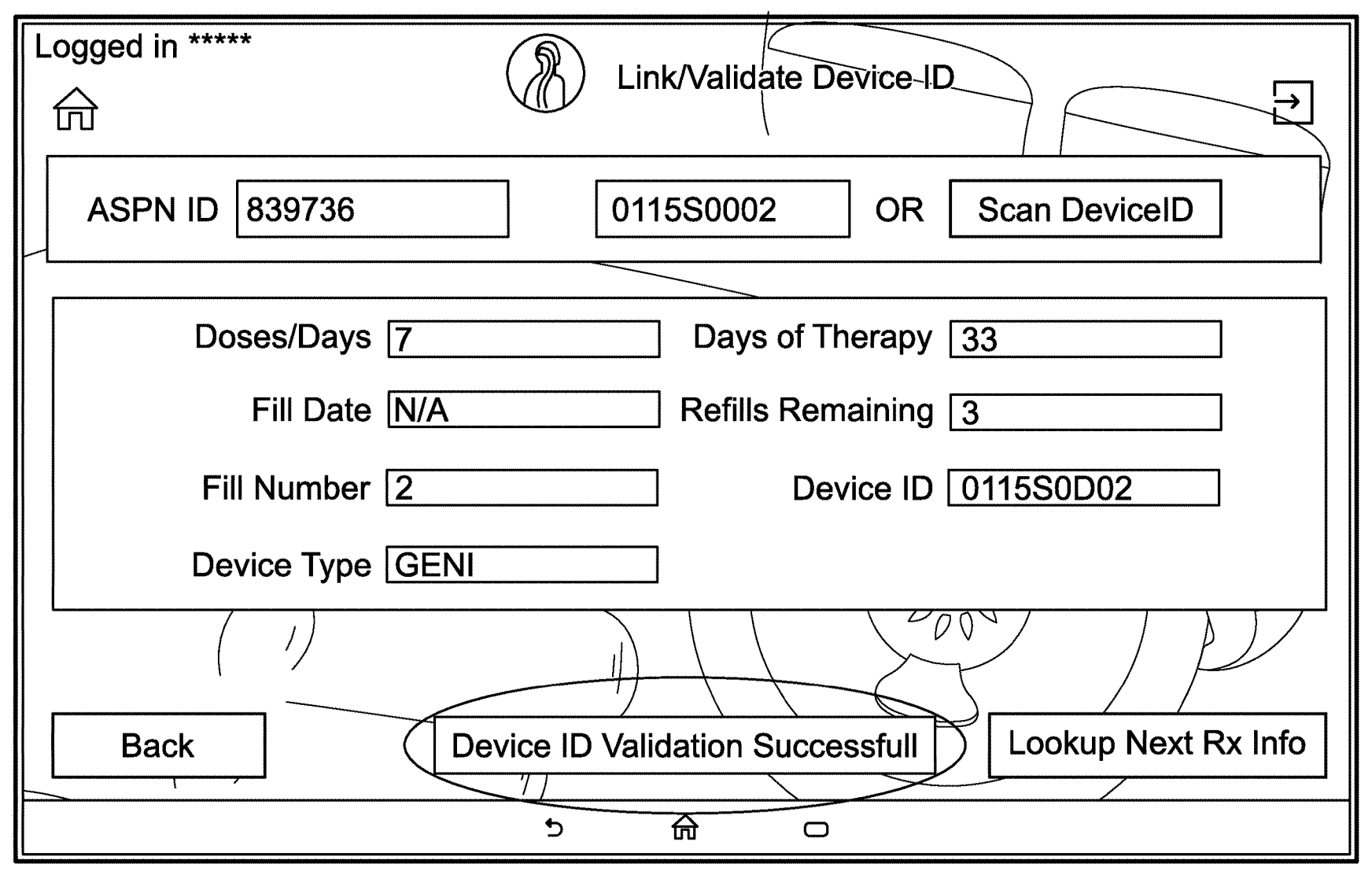

As shown in FIG. 19G, the POS terminal 600 displays a message when the device identifier is successfully validated and mapped, in a one-to-one correspondence, to the referral identifier, e.g. the NPI number or ASPN ID associated with a prescription. As such, the user of the POS terminal 600 can iteratively proceed with mapping another referral identifier with another device identifier. In this manner, a prescription from a healthcare provider (e.g., doctor, therapist) may be associated with a specific device by linking, in one-to-one correspondence, a patient card to a device identifier. For example, the one-to-one correspondence can mean that the patient card, whether an initial card or a refill, will only be recognized by and usable to activate/refill the specific device which bears the unique device identifier associated with the patient card at the time the patient card was filled or authorized. In a case of an initial satisfaction of a prescription, in which a patient receives a device for a first time, the unique identifier of the device is retrieved and matched with a prescription and patient card by scanning the device (e.g., by scanning a barcode or interrogating an RFID chip associated with the device), scanning the patient card (e.g., by scanning a barcode or interrogating an RFID chip associated with the patient card), and activating the patient card to contain prescription information, such as doses or a designated time period of use or others. Thereafter, when the patient card is held up to the device, then the device identifier programmed into the patient card will be recognized by the device and/or card, and the prescription information will be transferred (e.g., wired, wirelessly, waveguide) to the device. If the device identifier programmed into the patient card does not match the device identifier of the device, then at least some, most, or all prescription authorization information will not be transferred to the device. When a patient requires a prescription refill, then a new prescription is obtained (e.g., electronically) from the healthcare provider and submitted (e.g., electronically) to the pharmacy. The pharmacy will program (e.g., keying) the patient card with prescription information, and with the unique patient device identifier associated with the patient's device. The patient's device need not be present during the refill process because a system database contains the device identifier associated with the device previously issued to the patient, so the pharmacy can program the patient card with the appropriate dosage information contained in the prescription, and associate the patient card to be uniquely associated with the device identifier of the patient's device, and only that device. Such a system has a technical advantage or benefit of assuring that the prescribed treatment information may only be transferred from the patient card to the device possessed and previously assigned to the intended patient, and not any other patient or device.

Note that all aspects, characteristics, or components of initial provisioning or refilling of a medical device, as described herein, or all uses (e.g., prevention, diagnosis, monitoring, amelioration, or therapy related mechanical, thermal, acoustic, optical, vibratory, digital, data, or electronic acts) of the medical device, as described herein, or all uses of a storage medium (e.g., access, read, write, modify, copy, delete, format, encrypt, decrypt, load, unload, send, receive) can be written or uploaded to a block of a blockchain local to or remote from the medical device or the storage medium. For example, the system 100A can include or communicate with a node of a blockchain of a blockchain network. The node can enable writing, reading, modifying, copying, or deleting operations relative to a block of the blockchain. These operations can track initial provisioning, refilling, or all usages of the medical device or the storage medium for at least medical device or storage medium recordkeeping purposes (e.g., EMR, prescription, billing, device maintenance, device updates, system security).

FIGS. 20A-20J show an embodiment of a neurostimulator according to this disclosure. As shown in FIGS. 20A and 20G, a neurostimulator 700 can be used to provide non-invasive stimulation of a nerve. For example, the stimulation may be via an electrical energy, a mechanical energy, a thermal energy, an acoustic energy, a vibratory energy, or others. For example, the stimulation may be at a side of a neck of a patient. For example, the nerve can be a vagus nerve, a cranial nerve, a trigeminal nerve, a spinal nerve, or others.

The neurostimulator 700 includes a housing 702, a display 704, a plurality of stimulation surfaces 706, a power button 708, a cap 712, and a control button 714 and may include all or some of the features described above in this application. In some embodiments, the neurostimulator 700 includes a speaker housed via the housing 702 and powered via the battery. In some embodiments, the neurostimulator 700 includes a microphone housed via the housing 702 and powered via the battery. The housing 702 houses a signal generator and a battery. The housing 702 is opaque, but can be transparent. The battery powers the signal generator and the display. The power button 708 turns the neurostimulator 700 on and off. The button 708 can be a mechanical button or a touch-enabled surface, which can be haptic or configured to receive a touch input, a slide input, a gesture input, or others. The stimulation surfaces 706 contact a skin of a patient and conduct a stimulation energy, such as an electrical current, an electrical impulse, an actuation, or others, from the signal generator to the skin of the patient.

The display 704, which can present in monochrome, grayscale, or color, indicates a status of the neurostimulator 700, such as on, off, charging, dosage amount total, dosage amount remaining, stimulation time total, stimulation time remaining, or others. The display 704 can be of any type, such as a segment display, a liquid crystal display (LCD), an electrophoretic display, a field emission display (FED), or others, whether rigid, elastic, resilient, bendable, or flexible. The display 704 can be configured to receive a touch-input, including a gesture, a slide, or others. The cap 712 is mounted to the housing 702, such as via snug fit, friction, fastening, mating, adhering, or others. The cap 712 is transparent, but can be opaque. The cap 712 covers and protects the stimulation surfaces 706 from mechanical damage, interference, moisture, or others. The control button 714 is operably coupled to the signal generator and is thereby configured to increase or decrease an intensity of the stimulation by controlling the signal generator. The control button 714 can be a mechanical button or a touch-enabled surface, which can be haptic or configured to receive a touch input, a slide input, a gesture input, or others. The neurostimulator 700 can be charged via a charging station 716, whether in a wired, wireless, or waveguide manner.

For example, the neurostimulator 700 can be a multi-use, handheld, rechargeable, portable device comprising of a rechargeable battery, a set of signal-generating and amplifying electronics, and a control button for operator control of a signal amplitude. The device provides visible (display) and audible (beep) feedback on the device and stimulation status. A pair of stainless steel surfaces, which are a set of skin contact surfaces, allows a delivery of an electrical signal. The patient applies an electrode gel to the contact surfaces to maintain an uninterrupted conductive path from the contact surfaces to the skin on the neck of the patient. The stimulation surfaces are capped when not in use. The neurostimulator 700 can produce a low voltage electric signal including about five 5,000 Hz electric pulses (or less or more) that are repeated at a rate of 25 Hz (or less or more). A waveform of the electric pulses is approximately a sine wave with a peak voltage limited to about 24 volts (or less or more) when placed on the skin of the neck of the patient and a maximum output current of 60 mA (or less or more). The signal is transmitted through the skin of the neck to the vagus nerve. The neurostimulator 700 allows the patient to appropriately position and adjust a stimulation intensity as instructed a healthcare provider. Further details of appropriate waveforms and electrical signals and how to generate and transmit such signals to a desired nerve can be found in U.S. Pat. Nos. 8,874,205; 9,333,347; 9,174,066; 8,914,122 and 9,566,426, which are incorporated herein in their entireties by reference for at least these purposes as if copied and pasted herein, as disclosed herein, and for all purposes as if copied and pasted herein, such as all structures, all functions, and all methods of manufacture and use, as disclosed therein. Each dose can be applied for two minutes, after which the neurostimulator automatically stops delivering the neurostimulation. The neurostimulator 700 can allow for single or multiple uses or sessions. The neurostimulator can deliver a fixed number of treatments within a 24-hour period (or less or more). Once a maximum daily number of treatments has been reached, the neurostimulator 700 will not deliver any more treatments until a following 24-hour period expires. The neurostimulator can be charged via a charging station. The neurostimulator can allow for a fixed number of treatments within a defined time period, such as thirty one days or ninety three days, or some other period of time.

Each dose can be applied for two minutes, after which the neurostimulator automatically stops delivering the neurostimulation. The neurostimulator 700 can allows for multiple treatments. The neurostimulator can deliver a fixed number of treatments within a 24-hour period. Once a maximum daily number of treatments has been reached, the neurostimulator 700 will not deliver any more treatments until a following 24-hour period expires. The neurostimulator can be charged via a charging station. The neurostimulator can allow for a fixed number of treatments within a defined time period, such as thirty-one days or ninety-three days, or some other period of time.

The display 704 is able to present a plurality of symbols that are informative of various states of the neurostimulator 700. As such, FIGS. 20B-20D show a table of symbols that can be displayed via the display 704 as icons and a set of corresponding explanations of the symbols. In embodiments where the neurostimulator 704 includes the speaker, the table explains various sounds that can be output via the speaker. Note that such symbols and sounds are illustrative and can vary in color, shape, frequency, geometrical perimeter/volume, acoustical parameters, or others.

Figure 20E:
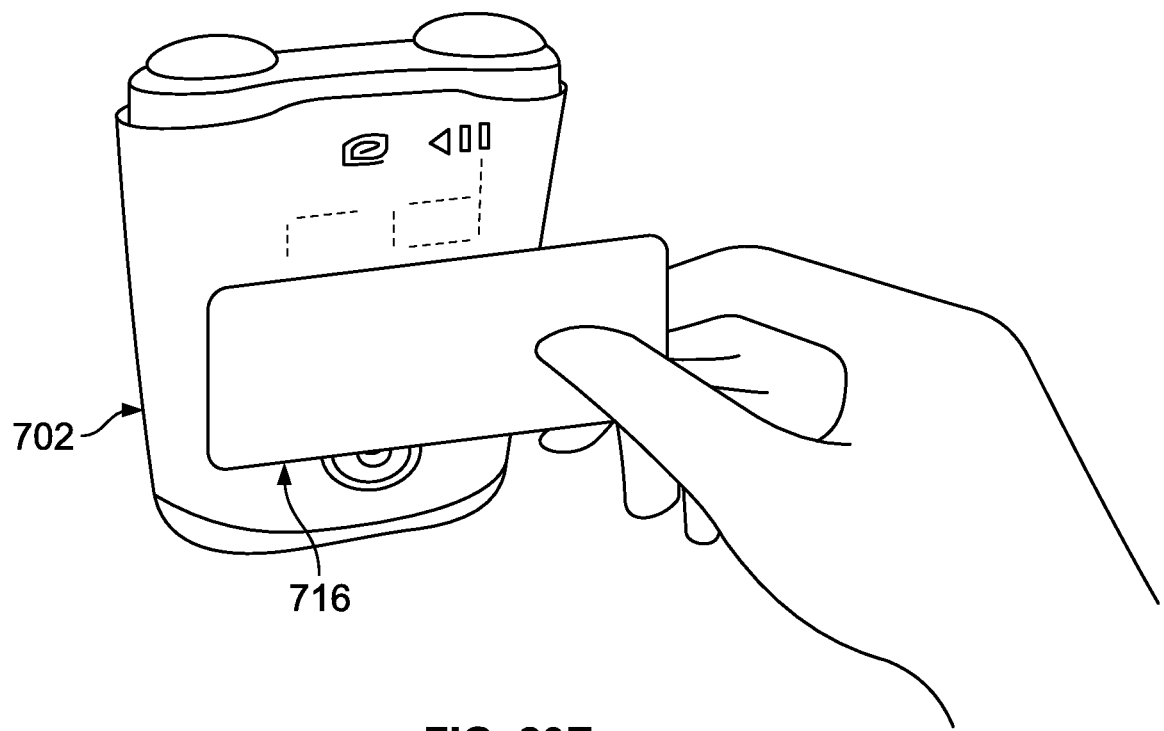

As shown in FIG. 20E, the neurostimulator 700 can be switched between a first mode and a second mode based on a card 716 being positioned in proximity thereof, whether via contact or avoiding contact, whether blocking the display 704 or below the display 704, as explained above. Note that the display 704 displays (1) a symbol informative of the card 716 being read via the neurostimulator 700, (2) a symbol informative of the battery of the neurostimulator 700 being full, and (3) a symbol informative of the neurostimulator 700 being reloaded via the card 716, as explained above. Also, note that the neurostimulator 700 can read the card 716 when the neurostimulator 700 is turned on. Further, note that if the neurostimulator 700 includes the speaker, then the neurostimulator 700 can output the sound alternative or additional to the display 704 displaying an appropriate symbol.

Figure 20F:
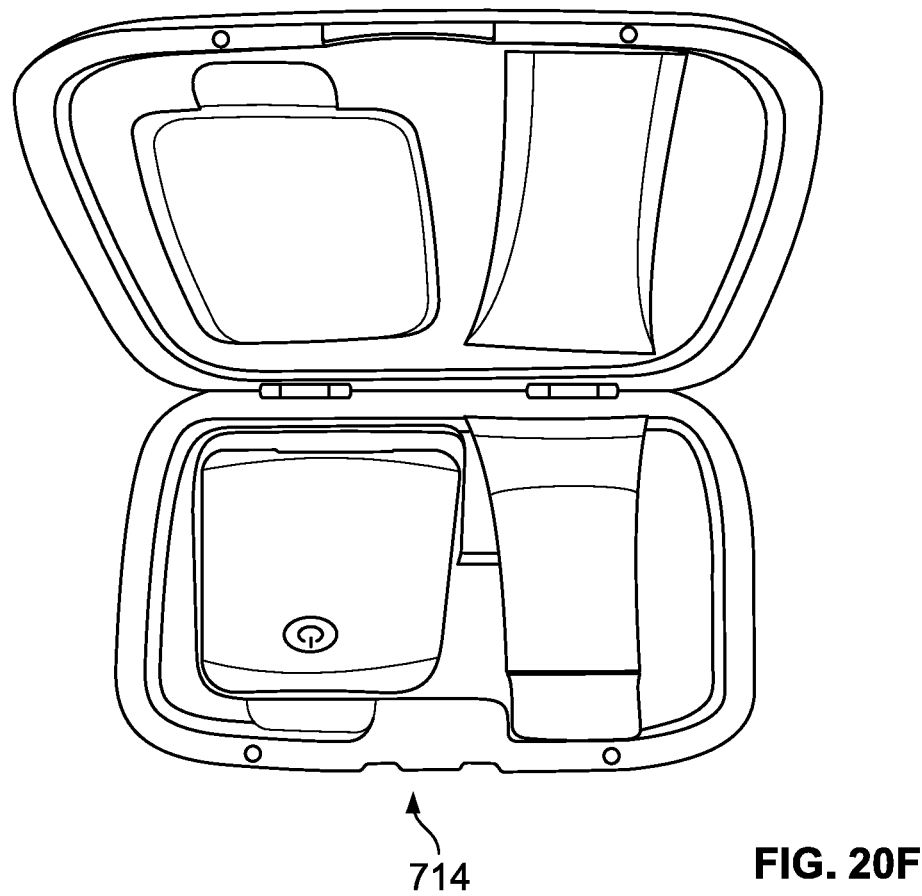

As shown in FIG. 20F, the charging station 716 can be used to recharge the neurostimulator 700. The charging station 716 includes a power adapter. As such, the power adapter can be plugged into a power outlet and with the power button 708 facing up, the housing 702 can be placed into the charging station 716, with the housing 702 snugly fitting into the charging station 716. Next, the display 704 can display a symbol informative of the battery of neurostimulator 700 being charged. For example, such symbol can change dynamically, such as via flashing, growing/increasing in perimeter/volume, or others. When the battery is fully charged, then the display 704 can display a symbol informative of such status. Note that if the battery is not being charged within the charging station 716, then the display 704 can display a symbol informative of such status or a symbol informative of an error status.

Figure 20H:
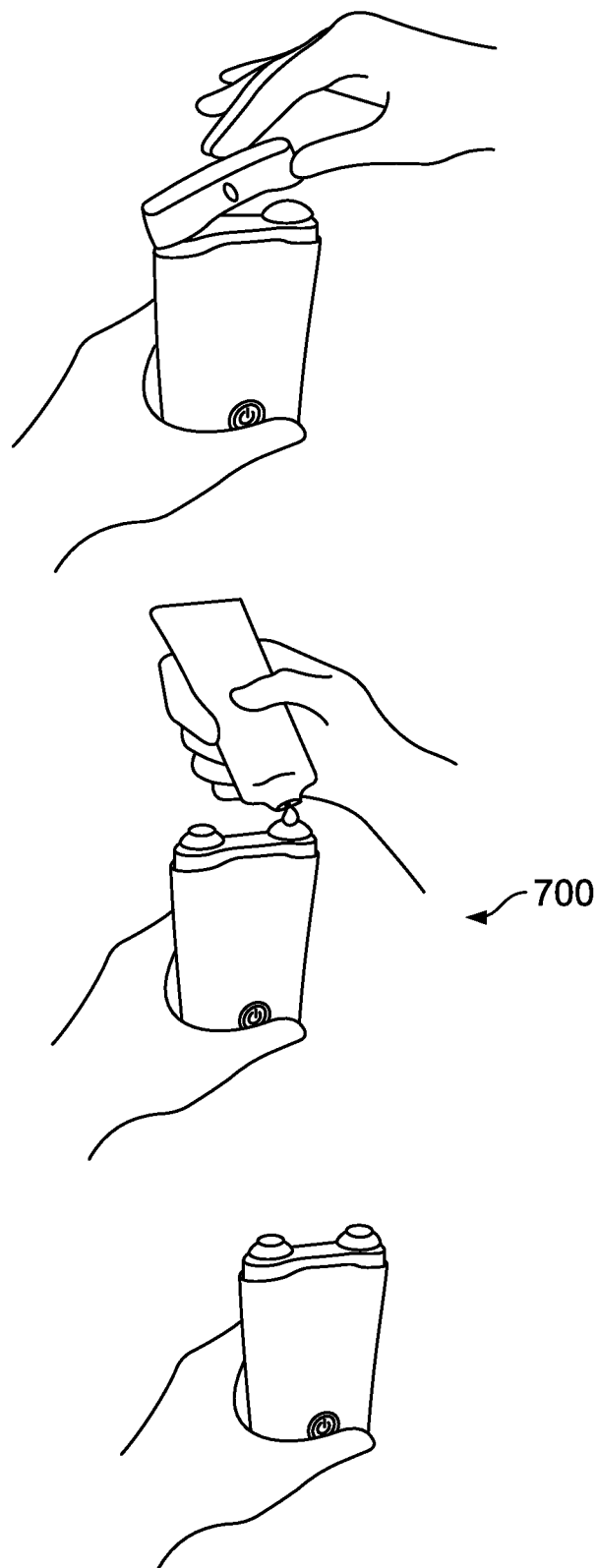
Figure 20I:
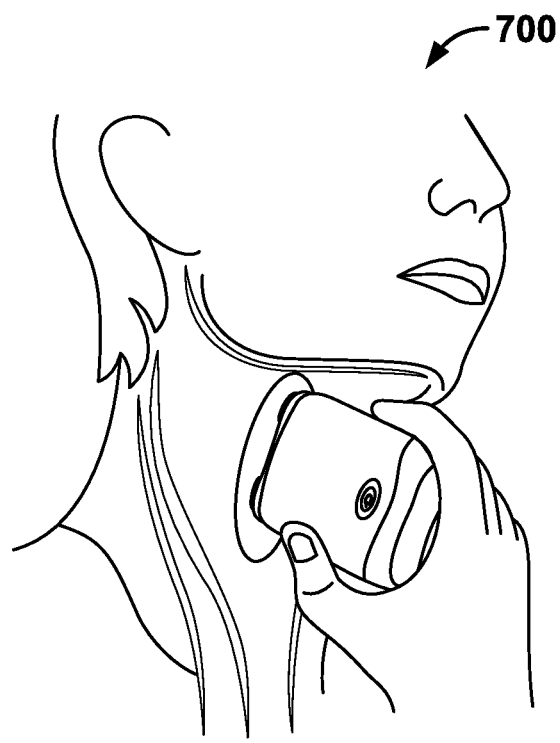

As shown in FIGS. 20H and 20I, the neurostimulator 700 can be used by removing the cap 712 from the housing 702, applying an energy conductive gel to the stimulation surfaces 706, and the positioning the stimulation surfaces 706 adjacent to the skin of the patient. In some embodiments, the energy conductive gel can be applied to the skin of the patient. Then, the power button 708 is turned on and the display 704 can display one or more symbols suitable at that time, as explained above. In embodiments where the housing 702 houses the speaker, then the speaker can output one or more sounds suitable at that time, as explained above. Note that the user can increase the intensity of stimulation by repeatedly pressing a top area of the control button 714 to a maximum level the user can tolerate. In embodiments where the neurostimulator 700 includes the speaker, the neurostimulator 700 can output a sound every time the control button 714 is pushed and the display 704 can indicate a numerical value between 1 and 40, although other information systems are possible, such as iconic or alphabetic, which signifies a level of stimulation.

Figure 20J:
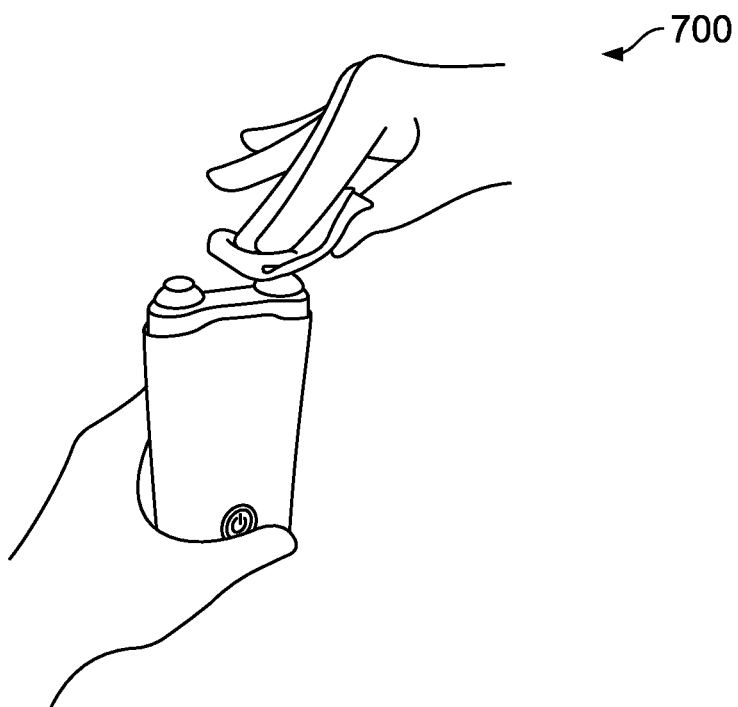

As shown in FIG. 20J, after the patient completes a session of neurostimulation, the display 704 will display a number of doses and days remaining and a last stimulation level before automatically turning off. In embodiments where the neurostimulator 700 includes the speaker, the neurostimulator 700 can stop automatically after two minutes (or less or more) and the speaker can output a sound informative of such action and automatically stop stimulation. Note that a number of days and doses remaining can be viewed by turning the neurostimulator 700 on. Similarly, the stimulation surfaces 706 can be cleaned by wiping any leftover gel off the stimulation surfaces 706 with a soft dry cloth. Moreover, the cap 712 can be placed back onto the housing 702.

Various terminology used herein can imply direct or indirect, full or partial, temporary or permanent, action or inaction. For example, when an element is referred to as being "on," "connected" or "coupled" to another element, then the element can be directly on, connected or coupled to the other element and/or intervening elements can be present, including indirect and/or direct variants. In contrast, when an element is referred to as being "directly connected" or "directly coupled" to another element, there are no intervening elements present.

Although the terms first, second, etc. can be used herein to describe various elements, components, regions, layers and/or sections, these elements, components, regions, layers and/or sections should not necessarily be limited by such terms. These terms are used to distinguish one element, component, region, layer or section from another element, component, region, layer or section. Thus, a first element, component, region, layer, or section discussed below could be termed a second element, component, region, layer, or section without departing from various teachings of this disclosure.

Various terminology used herein is for describing particular example embodiments and is not intended to be necessarily limiting of this disclosure. As used herein, various singular forms "a," "an" and "the" are intended to include various plural forms as well, unless a context clearly indicates otherwise. Various terms "comprises," "includes" and/or "comprising," "including" when used in this specification, specify a presence of stated features, integers, steps, operations, elements, and/or components, but do not preclude the presence and/or addition of one or more other features, integers, steps, operations, elements, components, and/or groups thereof.

As used herein, a term "or" is intended to mean an inclusive "or" rather than an exclusive "or." That is, unless specified otherwise, or clear from context, "X employs A or B" is intended to mean any of a set of natural inclusive permutations. That is, if X employs A; X employs B; or X employs both A and B, then "X employs A or B" is satisfied under any of the foregoing instances.

Features described with respect to certain example embodiments can be combined and sub-combined in and/or with various other example embodiments. Also, different aspects and/or elements of example embodiments, as disclosed herein, can be combined and sub-combined in a similar manner as well. Further, some example embodiments, whether individually and/or collectively, can be components of a larger system, wherein other procedures can take precedence over and/or otherwise modify their application. Additionally, a number of steps can be required before, after, and/or concurrently with example embodiments, as disclosed herein. Note that any and/or all methods and/or processes, at least as disclosed herein, can be at least partially performed via at least one entity in any manner.

Example embodiments of this disclosure are described herein with reference to illustrations of idealized embodiments (and intermediate structures) of this disclosure. As such, variations from various illustrated shapes as a result, for example, of manufacturing techniques and/or tolerances, are to be expected. Thus, various example embodiments of this disclosure should not be construed as necessarily limited to various particular shapes of regions illustrated herein, but are to include deviations in shapes that result, for example, from manufacturing.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing, and/or other any other types of manufacturing. For example, some manufacturing processes include three dimensional (3D) printing, laser cutting, computer numerical control routing, milling, pressing, stamping, vacuum forming, hydroforming, injection molding, lithography, and so forth.

Any and/or all elements, as disclosed herein, can be and/or include, whether partially and/or fully, a solid, including a metal, a mineral, an amorphous material, a ceramic, a glass ceramic, an organic solid, such as wood and/or a polymer, such as rubber, a composite material, a semiconductor, a nanomaterial, a biomaterial and/or any combinations thereof. Any and/or all elements, as disclosed herein, can be and/or include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, opaqueness, luminescence, reflection, phosphorescence, anti-reflection and/or holography, a photo-sensitive coating, an electronic and/or thermal property coating, such as for passivity, insulation, resistance or conduction, a magnetic coating, a water-resistant and/or waterproof coating, a scent coating and/or any combinations thereof. Any and/or all elements, as disclosed herein, can be rigid, flexible, and/or any other combinations thereof. Any and/or all elements, as disclosed herein, can be identical and/or different from each other in material, shape, size, color and/or any measurable dimension, such as length, width, height, depth, area, orientation, perimeter, volume, breadth, density, temperature, resistance, and so forth.

Unless otherwise defined, all terms (including technical and scientific terms) used herein have the same meaning as commonly understood by one of ordinary skill in an art to which this disclosure belongs. Various terms, such as those defined in commonly used dictionaries, should be interpreted as having a meaning that is consistent with a meaning in a context of a relevant art and should not be interpreted in an idealized and/or overly formal sense unless expressly so defined herein.

Furthermore, relative terms such as "below," "lower," "above," and "upper" can be used herein to describe one element's relationship to another element as illustrated in the set of accompanying illustrative drawings. Such relative terms are intended to encompass different orientations of illustrated technologies in addition to an orientation depicted in the set of accompanying illustrative drawings. For example, if a device in the set of accompanying illustrative drawings were turned over, then various elements described as being on a "lower" side of other elements would then be oriented on "upper" sides of other elements. Similarly, if a device in one of illustrative figures were turned over, then various elements described as "below" or "beneath" other elements would then be oriented "above" other elements. Therefore, various example terms "below" and "lower" can encompass both an orientation of above and below.

As used herein, a term "about" and/or "substantially" refers to a +/−10% variation from a nominal value/term. Such variation is always included in any given value/term provided herein, whether or not such variation is specifically referred thereto.

If any disclosures are incorporated herein by reference and such disclosures conflict in part and/or in whole with this disclosure, then to an extent of a conflict, if any, and/or a broader disclosure, and/or broader definition of terms, this disclosure controls. If such disclosures conflict in part and/or in whole with one another, then to an extent of a conflict, if any, a later-dated disclosure controls.

In some embodiments, various functions or acts can take place at a given location and/or in connection with the operation of one or more apparatuses or systems. In some embodiments, a portion of a given function or act can be performed at a first device or location, and a remainder of the function or act can be performed at one or more additional devices or locations.

Various corresponding structures, materials, acts, and equivalents of all means or step plus function elements in various claims below are intended to include any structure, material, or act for performing the function in combination with other claimed elements as specifically claimed. Various embodiments were chosen and described in order to best explain various principles of this disclosure and various practical applications thereof, and to enable others of ordinary skill in a pertinent art to understand this disclosure for various embodiments with various modifications as are suited to a particular use contemplated.

Various diagrams depicted herein are illustrative. There can be many variations to such diagrams or steps (or operations) described therein without departing from various spirits of this disclosure. For instance, various steps can be performed in a differing order or steps can be added, deleted or modified. All of these variations are considered a part of this disclosure. People skilled in an art to which this disclosure relates, both now and in future, can make various improvements and enhancements which fall within various scopes of various claims which follow.

The invention claimed is:

1. A system comprising:
a medical device comprising: a power supply, a signal generator and an electrode, wherein the signal generator is configured to apply one or more electrical impulses to the electrode for a period of time, the period of time being defined as a single dose; and
a processor coupled to the medical device, wherein the processor is configured to switch the medical device from an activated mode to a deactivated mode after a specific number of single doses have been applied by the signal generator; and
a storage medium that includes a content, wherein the processor is configured to interface with the storage medium based on the processor switching the medical device from the activated mode to the deactivated mode such that the content of the storage medium is deleted or scrambled.

2. The system of claim 1, wherein the medical device comprises a housing and the processor is disposed within the housing.

3. The system of claim 1, wherein the processor is wirelessly coupled to the medical device.

4. The system of claim 1, wherein the content includes a defined time period for the activated mode.

5. The system of claim 1, wherein the content includes a defined number of doses for the activated mode.

6. The system of claim 1, wherein the storage medium is card shaped.

7. The system of claim 1, further comprising a reader configured to read the content from the storage medium.

8. The system of claim 7, wherein the content includes a first content and a second content, wherein the reader is configured to read the first content from the storage medium such that the processor erases or scrambles the first content and does not erase or scramble the second content.

9. The system of claim 8, wherein the first content includes a single dose.

10. The system of claim 1, wherein the processor is configured to switch the medical device from an activated mode to a deactivated mode after a specific time period.

11. The system of claim 1, wherein the signal generator transmits the electrical impulse from the electrode transcutaneously and non-invasively through an outer skin surface of a patient such that the electrical impulse modulates a nerve within the patient.

12. The system of claim 11, wherein the electrical impulse modulates a vagus nerve and causes the vagus nerve to generate an action potential to treat a medical condition within the patient.

13. A method comprising:
generating an electrical impulse with an energy source coupled to a medical device;
transmitting the one or more electrical impulses to a target nerve within a patient for a period of time defined as a single dose;
causing, via a processor, the medical device to switch from a deactivated to an activated mode for a specific number of single doses;
causing, via a processor, a reader to read the content from a storage medium; and
erasing or scrambling the content in the storage medium after the content has been read by the reader.

14. The method of claim 13, further comprising causing the medical device, via the processor, to switch the from the activated mode to the deactivated mode after a defined time period.

15. The method of claim 14, wherein the content includes a first content and a second content, the method further comprising erasing or scrambling the first content after the reader has read the first content, without erasing or scrambling the second content.

16. The method of claim 14, further comprising transmitting the electrical impulse transcutaneously and non-invasively through an outer skin surface of a patient such that the electrical impulse modulates a nerve within the patient.

17. The method of claim 16, wherein the electrical impulse modulates a vagus nerve within the patient to generate an action potential to treat a medical condition within the patient.

* * * * *